(12) United States Patent
Ziv

(10) Patent No.: US 9,993,563 B2
(45) Date of Patent: *Jun. 12, 2018

(54) COMPOUNDS AND METHODS FOR TRANS-MEMBRANE DELIVERY OF MOLECULES

(71) Applicant: Aposense LTD., Petach-Tikva (IL)

(72) Inventor: Ilan Ziv, Kfar Saba (IL)

(73) Assignee: Aposense LTD., Petach-Tikva (IL)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/222,559

(22) Filed: Jul. 28, 2016

(65) Prior Publication Data

US 2017/0100486 A1    Apr. 13, 2017

Related U.S. Application Data

(63) Continuation-in-part of application No. 15/164,344, filed on May 25, 2016, which is a continuation-in-part of application No. 15/057,813, filed on Mar. 1, 2016, which is a continuation-in-part of application No. 14/985,526, filed on Dec. 31, 2015, which is a continuation-in-part of application No. 14/872,179, filed on Oct. 1, 2015, which is a continuation-in-part of application No. 14/870,406, filed on Sep. 30, 2015, now abandoned, which is a continuation-in-part of application No. 14/830,799, filed on Aug. 20, 2015, which is a continuation-in-part of application No. PCT/IL2015/000019, filed on Mar. 29, 2015.

(60) Provisional application No. 61/971,548, filed on Mar. 28, 2014, provisional application No. 61/978,903, filed on Apr. 13, 2014, provisional application No. 62/002,870, filed on May 25, 2014, provisional application No. 62/008,509, filed on Jun. 6, 2014, provisional application No. 62/091,551, filed on Dec. 14, 2014.

(51) Int. Cl.

| | | |
|---|---|---|
| *A61K 47/48* | (2006.01) | |
| *A61K 48/00* | (2006.01) | |
| *A61K 31/713* | (2006.01) | |
| *A61K 47/28* | (2006.01) | |
| *C12N 15/113* | (2010.01) | |
| *A61K 38/00* | (2006.01) | |
| *C07J 41/00* | (2006.01) | |
| *C07J 43/00* | (2006.01) | |
| *A61K 38/46* | (2006.01) | |

(52) U.S. Cl.
CPC ...... *A61K 47/48123* (2013.01); *A61K 31/713* (2013.01); *A61K 38/465* (2013.01); *A61K 47/48023* (2013.01); *C07J 41/00* (2013.01); *C07J 43/00* (2013.01); *C12N 15/113* (2013.01); *C12N 2310/14* (2013.01); *C12N 2310/3145* (2013.01); *C12N 2310/3231* (2013.01); *C12N 2310/351* (2013.01)

(58) Field of Classification Search
None
See application file for complete search history.

(56) References Cited

U.S. PATENT DOCUMENTS

| | | |
|---|---|---|
| 6,028,066 A | 2/2000 | Unger |
| 8,809,514 B2 | 8/2014 | Yamada et al. |
| 2011/0123457 A1 | 5/2011 | Yu |
| 2015/0141678 A1 | 5/2015 | Payne et al. |

FOREIGN PATENT DOCUMENTS

| | | |
|---|---|---|
| FR | 2846969 | 5/2004 |
| WO | WO 97/40679 | 11/1997 |
| WO | WO98/50041 | 11/1998 |
| WO | WO2005/077968 | 8/2005 |

OTHER PUBLICATIONS

Shengguo Sun; Adejare, Adeboye "Fluorinated Molecules as Drugs and Imaging Agents in the CNS" Current Topics in Medicinal Chemistry, Jul. 2006, vol. 6 Issue 14, pp. 1457-1464.
International Search Report for Application No. PCT/IL2015/000019, dated Jul. 28, 2015.
Krafft, "Fluorocarbons and fluorinated amphiphiles in drug delivery and biomedical research" Advanced Drug Delivery Reviews, Apr. 25, 2001, vol. 47, No. 2-3, pp. 209-228.
Vierling et al. "Highly fluorinated amphiphiles as drug and gene carrier and delivery systems" Journal of Fluorine Chem. Feb. 2001, vol. 107 No. 2, pp. 337-354.
Reiss, "Fluorous micro- and nanophases with a biomedical perspective" Tetrahedron, May 2002, vol. 58, No. 20, pp. 4113-4131.
Alconcel et al. "FDA-approved poly(ethylene glycol)-protein conjugate drugs", Polymer Chemistry, Jun. 2011, vol. 2, No. 14, pp. 1442-1448.
Office Action of U.S. Appl. No. 14/872,179 dated Apr. 25, 2016.
Andersen, Olaf Sparre, et al. "Effect of phloretin on the permeability of thin lipid membranes." The Journal of general physiology 67.6 (1976): pp. 749-771.

(Continued)

*Primary Examiner* — Bong-Sook Baek
(74) *Attorney, Agent, or Firm* — Pearl Cohen Zedek Latzer Baratz LLP

(57) ABSTRACT

A novel delivery system for drugs, and especially macromolecules such as proteins or oligonucleotides through biological membranes is provided, and specifically delivery of siRNA. The delivery system comprises conjugation of the macromolecule drug to a moiety that enables effective passage through the membranes. Respectively, novel compounds and pharmaceutical compositions are provided, utilizing said delivery system. In one aspect of the invention, the compounds may be utilized in medical practice, for example, in delivery of siRNA or antisense oligonucleotides across biological membranes for the treatment of medical disorders.

21 Claims, 30 Drawing Sheets
(17 of 30 Drawing Sheet(s) Filed in Color)

(56) References Cited

OTHER PUBLICATIONS

Ikumi, Yusuke, et al. "Polymer-phloridzin conjugates as an antidiabetic drug that Inhibits glucose absorption through the Na+/glucose cotransporter (SGLT1) in the small intestine." Journal of controlled release 125.1 (2008): pp. 42-49.

Üllen, Andreas, et al. "Covalent adduct formation between the plasmalogen-derived modification product 2-chlorohexadecanal and phloretin." Biochemical pharmacology 93.4 (2015): pp. 470-481.

International Search Report for PCT Application No. PCT/IL2016/50893 dated Dec. 28, 2016.

Bellucci, Maria Cristina, and Alessandro Volonterio. "Multicomponent Synthesis of Peptide-Sugar Conjugates Incorporating Hexafluorovaline." Advanced Synthesis & Catalysis 352.16 (2010): pp. 2791-2798.

Janout, Vaclav, et al. "Molecular umbrella conjugate for the ocular delivery of siRNA." Bioconjugate chemistry 25.2 (2014): pp. 197-201.

Grijalvo, Santiago, et al. "Synthesis of oligonucleotides carrying amino lipid groups at the 3'-end for RNA interference studies." The Journal of organic chemistry 75.20 (2010): pp. 6806-6813.

Yue, Xuyi, Yue Feng, and Y. Bruce Yu. "Synthesis and characterization of fluorinated conjugates of albumin." Journal of Fluorine Chemistry 152 (2013): pp. 173-181.

Jiang, Zhong-Xing, and Y. Bruce Yu. "The design and synthesis of highly branched and spherically symmetric fluorinated macrocyclic chelators." Synthesis Feb. 2008 (2008): pp. 215-220.

Blazejewski., et al. "Synthesis, characterization and biological evaluation of 7α- perfluoroalkylestradiol derivatives." Bioorganic & medicinal chemistry 11.3 (2003): pp. 335-345.

Schiller, R., A. P. Funke, and C. Günther. "DSC measurements on full thickness mice skin." Journal of Thermal Analysis and Calorimetry 77.2 (2004): 497-510.

Extended European Search Report for EP Application No. 15770224 dated Sep. 22, 2017.

```
SEQUENCE LISTING

<160> NUMBER OF SEQ ID NOS: 8

<210> SEQ ID NO 1
<211> LENGTH: 27
<212> TYPE: DNA
<213> ORGANISM: Artificial Sequence
<220> FEATURE:
<223> OTHER INFORMATION: Single strand DNA oligonucleotide
<220> FEATURE:
<221> NAME/KEY: misc_feature
<222> LOCATION: (1)..(1)
<223> OTHER INFORMATION: C is attached to MNM-TT-iCy3

<400> SEQUENCE: 1
cggtggtgca gatgaacttc agggtca                                          27

<210> SEQ ID NO 2
<211> LENGTH: 29
<212> TYPE: DNA
<213> ORGANISM: Artificial Sequence
<220> FEATURE:
<223> OTHER INFORMATION: Single strand DNA oligonucleotide
<220> FEATURE:
<221> NAME/KEY: misc_feature
<222> LOCATION: (1)..(1)
<223> OTHER INFORMATION: T is attached to MNM

<400> SEQUENCE: 2
tgaccctgaa gttcatctgc accaccgaa                                        29

<210> SEQ ID NO 3
<211> LENGTH: 27
<212> TYPE: DNA
<213> ORGANISM: Artificial Sequence
<220> FEATURE:
<223> OTHER INFORMATION: Single strand DNA oligonucleotide
<220> FEATURE:
<221> NAME/KEY: misc_feature
<222> LOCATION: (1)..(1)
<223> OTHER INFORMATION: C is attached to Apo-si-11-TT-iCy3

<400> SEQUENCE: 3
cggtggtgca gatgaacttc agggtca                                          27

<210> SEQ ID NO 4
<211> LENGTH: 29
<212> TYPE: DNA
<213> ORGANISM: Artificial Sequence
<220> FEATURE:
<223> OTHER INFORMATION: Single strand DNA oligonucleotide
<220> FEATURE:
<221> NAME/KEY: misc_feature
<222> LOCATION: (1)..(1)
<223> OTHER INFORMATION: T is attached to Apo-si-11

<400> SEQUENCE: 4
tgaccctgaa gttcatctgc accaccgaa                                        29
```

```
<210> SEQ ID NO 5
<211> LENGTH: 25
<212> TYPE: RNA
<213> ORGANISM: Artificial Sequence
<220> FEATURE:
<223> OTHER INFORMATION: Artificial short sequence

<400> SEQUENCE: 5
acccugaagu ucaucugcac caccg                                             25

<210> SEQ ID NO 6
<211> LENGTH: 27
<212> TYPE: RNA
<213> ORGANISM: Artificial Sequence
<220> FEATURE:
<223> OTHER INFORMATION: Artificial short sequence

<400> SEQUENCE: 6
cgguggugca gaugaacuuc aggguca                                           27

<210> SEQ ID NO 7
<211> LENGTH: 27
<212> TYPE: RNA
<213> ORGANISM: Artificial Sequence
<220> FEATURE:
<223> OTHER INFORMATION: Artificial short sequence
<220> FEATURE:
<221> NAME/KEY: misc_feature
<222> LOCATION: (1)..(1)
<223> OTHER INFORMATION: C is attached to Apo-Si-S-S

<400> SEQUENCE: 7
cgguggugca gaugaacuuc aggguca                                           27

<210> SEQ ID NO 8
<211> LENGTH: 25
<212> TYPE: RNA
<213> ORGANISM: Artificial Sequence
<220> FEATURE:
<223> OTHER INFORMATION: Artificial short sequence
<220> FEATURE:
<221> NAME/KEY: misc_feature
<222> LOCATION: (1)..(1)
<223> OTHER INFORMATION: A is attached to Apo-Si-S-S

<400> SEQUENCE: 8
acccugaagu ucaucugcac caccg                                             25
```

COMPOUNDS AND METHODS FOR TRANS-MEMBRANE DELIVERY OF MOLECULES

CROSS-REFERENCE TO RELATED APPLICATIONS

This application is a continuation-in-part of U.S. patent application Ser. No. 15/164,344 filed on May 25, 2016, which is a continuation-in-part of U.S. patent application Ser. No. 15/057,813 filed on Mar. 1, 2016, which is a continuation-in-part of U.S. patent application Ser. No. 14/985,526 filed on Dec. 31, 2015, which is a continuation-in-part of U.S. patent application Ser. No. 14/872,179, filed on Oct. 1, 2015, which is a continuation-in-part of U.S. patent application Ser. No. 14/870,406, filed on Sep. 30, 2015, which is a continuation-in-part of U.S. patent application Ser. No. 14/830,799, filed on Aug. 20, 2015, which is a continuation-in-part of PCT International Application No. PCT/IL2015/000019, International Filing Date Mar. 29, 2015, claiming the benefit of U.S. Provisional Patent Applications Nos. 61/971,548, fled Mar. 28, 2014, 61/978,903, filed Apr. 13, 2014, 62/002,870, filed May 25, 2014, 62/008,509 filed Jun. 6, 2014, and 62/091,551, filed Dec. 14, 2014, which are hereby incorporated by reference.

FIELD OF THE INVENTION

The invention relates to a novel delivery system and methods for delivery of molecules and macromolecules across biological membranes into cells, optionally with subsequent intracellular entrapment.

BACKGROUND

Protein pathology is a common denominator in the etiology or pathogenesis of many medical disorders, ranging from malfunction of a mutated protein, to pathological gain of function, where a specific protein acquires a novel property which renders it toxic. Conceptually, inhibition of the synthesis of these proteins by gene therapy may hold promise for patients having such protein anomaly.

One of the major advances of recent years is the concept of silencing a specific gene by RNA interference, using small interfering RNA (siRNA) RNA interference is based on short ($\approx$19-27 base pairs), double-stranded RNA sequences (designated siRNA), capable of acting, in concert with cellular biological systems [among others, the Dicer protein complex, which cleaves double-stranded RNA to produce siRNA, and the RNA-induced silencing complex (RISC)], to inhibit translation, and mark for degradation specific mRNA sequences, thus inhibiting gene expression at the translational stage. The use of antisense oligonucleotide (ASO), being a short sequence (usually 13-25 nucleotides) of unmodified or chemically modified DNA molecules, complementary to a specific messenger RNA (mRNA), has also been used to inhibit the expression and block the production of a specific target protein. However, albeit the tremendous potential benefits of such approaches for medical care, delivery of such macromolecules into cells remains a substantial challenge, due to the relatively large and highly-charged structures of oligonucleotides (for example, siRNA has an average molecular weight of 13 kDa, and it carries about 40 negatively-charged phosphate groups). Therefore, trans-membrane delivery of oligonucleotides requires overcoming a very large energetic barrier.

The membrane dipole potential is an electric potential that exists within any phospholipid membrane, between the water/membrane interface and the membrane center (positive inside). It is assumed to be generated by the highly ordered carbonyl groups of the phospholipid glyceryl esteric bonds, and its amplitude is about 220-280 mV. Since the membrane dipole potential resides in a highly hydrophobic environment of dielectric constant of 2-4, it translates into a very strong electric field of $10^8$-$10^9$ V/m. Conceivably, the membrane dipole potential and related intra-membrane electric field are highly important for the function of membrane proteins, determining their conformation and activity. However, to the best of our knowledge, to date, the dipole potential has not been recruited for drug delivery.

Various methods have been developed for delivery of macromolecules such as oligonucleotides or proteins across biological membranes. These methods include viral vectors, as well as non-viral delivery systems, such as cationic lipids or liposomes. However to date, use of these methods has been largely limited to applications in vitro, or to focal administration in vivo, e.g., by direct injection into the eye or direct administration into the lung. Efficient delivery has also been achieved to the liver. Among these methods, electroporation is known to be an effective and widely-used method for delivery of macromolecules in vitro. According to this method, an external electric field is applied to a cell suspension, leading to collision of charged target molecules with the cell membranes, subsequent temporary and focal membrane destabilization, and consequent passage of the macromolecules into the cells. However, as described above, electroporation is mainly used in vitro, and attempts to extend its use to applications in vivo encountered limited success, and was attempted only to specific organs (e.g., muscle, lung), to which external electrodes could be inserted.

In conclusion, delivery of macromolecules such as oligonucleotides or proteins through cell membranes, or through other biological barriers, such as the Blood-Brain-Barrier, Blood-Ocular-Barrier, or the Blood-Fetal-barrier, still presents a substantial unmet need, and systemic delivery of therapeutic macromolecules, still remains a huge, unaddressed challenge.

SUMMARY OF THE INVENTION

Embodiments of the present invention provide a delivery system, based on conjugation of drugs to be delivered to novel, rationally-designed "Molecular NanoMotors (MNMs)". The MNMs according to embodiments of the invention comprise a structure of moiety E, E' or E", as set forth in Formula (II) below. The drugs to be delivered by the MNMs may be either small-molecule drugs, or macromolecules, such as, peptides, proteins or oligonucleotides (e.g., single-stranded or double-stranded, RNA or DNA). In an embodiment of the invention, the macromolecules to be delivered include RNA strands for gene silencing, i.e., siRNA (small interfering RNA), or DNA sequences designed to serve as antisense oligonucleotides (ASO).

Conjugates of drugs (e.g., small molecule drugs or macromolecules) with MNMs according to embodiments of the invention may be utilized in basic research or clinical medical practice. Among others, they can be used for treatment of medical disorders, where aberrant proteins or protein dysfunction play a role, and where silencing of the expression of genes encoding for these proteins can be beneficial. Such applications can be, for example, treatment of degenerative disorders, cancer, toxic or ischemic insults, infections, or immune-mediated disorders.

In an embodiment of the invention, there is provided a method for delivery of a drug across biological membranes, the method comprising utilization of a Conjugate, having the structure as set forth in Formula (I):

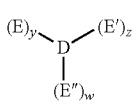

Formula (I)

or pharmaceutically acceptable salts, hydrates, solvates and metal chelates of the compound represented by the structure as set forth in Formula (I), and solvates and hydrates of the salts, wherein:

D is the drug to be delivered across biological membranes, selected from a group consisting of a small-molecule drug, a peptide, a protein, and a native or modified, single-stranded or double-stranded DNA or RNA, siRNA or ASO; y, z and w are each an integer, independently selected from 0, 1, 2, 3, 4, 5 or 6, wherein whenever the integer is 0, it means that the respective E moiety is null; at least one of y, z or w is different from 0;

E, E', or E" can be the same or different, each having the structure as set forth in general Formula (II):

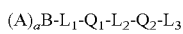

Formula (II)

wherein each A moiety is independently selected from structures set forth in Formulae (III), (IV), (V) and (VI):

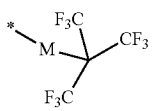

Formula (III)

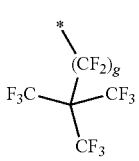

Formula (IV)

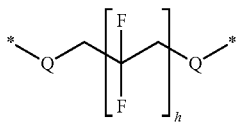

Formula (V)

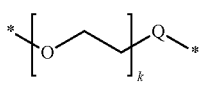

Formula (VI)

M is selected from —O— or —CH$_2$—; and g, h and k are each individually an integer selected from the group consisting of 0, 1, 2, 3, 4, 5, 6, 7, 8, 9, 10, 11, 12, 13, 14, 15 and 16; * is —H, or a point or linkage to B, or to another A group; a is an integer, selected from 1, 2, 3 or 4; Q is oxygen or amine.

wherein B is selected from one or more groups consisting of:
a linear, cyclic or branched $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, alkyl or hetero-alkyl, wherein each is optionally substituted by one or more halogen, hydroxyl, methoxy, fluorocarbon, amine or thiol; or optionally linked to an ether, an ester, or a amide group;

a linear, cyclic or branched $C_2$, $C_3$, $C_4$, $C_5$, $C_6$, $C_7$, $C_8$, $C_9$, $C_{10}$, $C_{11}$, $C_{12}$, $C_{13}$, $C_{14}$ alkylene or heteroalkylene, wherein each is optionally substituted by one or more halogen, hydroxyl, methoxy, fluorocarbon, amine or thiol; or optionally linked to an ether, an ester, or an amide group;

$C_5$, $C_6$, $C_7$, $C_8$, $C_9$, $C_{10}$, $C_{11}$, $C_{12}$, $C_{13}$, $C_{14}$ or heteroaryl, wherein each is optionally substituted by one or more halogen, hydroxyl, methoxy, fluorocarbon, amine thiol; or optionally linked to an ether, an ester, or an amide group;

one or more steroid moiety, wherein the steroid moiety ischolesterol, bile acid, estrogen, estradiol, estriol, lithocholic acid or any analog thereof or at nucleoside or nucleotide; or any combination thereof, wherein each is optionally substituted by one or more halogen, hydroxyl, methoxy, fluorocarbon, amine or thiol; or each is optionally linked to an ether, an ester, an amine, or an amide group;

and any combination thereof;

$Q_1$ and $Q_2$ are each a cleavable group, independently selected from null, ester, thio-ester, amide [e.g., —C(=O)—NH— or —NH—C(=O)—], carbamate [e.g., —O—C(=O)—NH— or —NH—C(=O)—O—], urea [—NH—C(=O)—NH—], disulfide [—(S—S)—], ether [—O—], amine, imidazole, triazole, dilactone; a metal chelator selected from BAPTA and EGTA, including its chelated metal ion; and any combinations thereof;

$L_1$, $L_2$ and $L_3$ are each independently selected from null and the group consisting of:
linear, cyclic or branched $C_1$, $C_2$, $C_3$, $C_4$, $C_5$, $C_6$, $C_7$, $C_8$, $C_9$, $C_{10}$, $C_{11}$, $C_{12}$, $C_{13}$ or $C_{14}$, alkyl or hetero-alkyl, wherein each is optionally substituted by one or more halogen, hydroxyl, methoxy, fluorocarbon, amine, or thiol; or linked to an ether group;

linear, cyclic or branched $C_2$, $C_3$, $C_4$, $C_5$, $C_6$, $C_7$, $C_8$, $C_9$, $C_{10}$, $C_{11}$, $C_{12}$, $C_{13}$ or $C_{14}$ alkylene or heteroalkylene, wherein each is optionally substituted by one or more halogen, hydroxyl, methoxy, fluorocarbon, amine, thiol; or linked to an ether group;

$C_5$, $C_6$, $C_7$, $C_8$, $C_9$, $C_{10}$, $C_{11}$, $C_{12}$, $C_{13}$ or $C_{14}$ aryl or heteroaryl, wherein each is optionally substituted by one or more halogen, hydroxyl, methoxy, fluorocarbon, amine, thiol; or linked to an ether group;

—(O—CH$_2$—CH$_2$)$_u$—, wherein each is optionally substituted by one or more halogen, hydroxyl, methoxy, fluorocarbon, amine, or thiol;

nucleoside, nucleotide; imidazole, azide, acetylene; and any combinations thereof, wherein each is optionally substituted by one or more halogen, hydroxyl, methoxy, fluorocarbon, amine, thiol; or linked to an ether group; and wherein u is an integer of 1, 2, 3, 4 or 5; and any combinations thereof;

wherein at least one of $Q_1$, $Q_2$, $L_1$, $L_2$ and $L_3$ is not null, and wherein each of $Q_1$, $Q_2$, $L_1$, $L_2$ and $L_3$ optionally comprises a T moiety; wherein T is an initiator group, selected from $C_4$, $C_5$, $C_6$—1,2-dithiocycloalkyl (1,2-dithiocyclobutane; 1,2-dithiocyclo-pentane; 1,2-dithiocyclohexane; 1,2-dithiocycloheptane); γ-Lactam (5 atoms amide ring), δ-Lactam (6 atoms amide ring) or ε-Lactam (7 atoms amide ring); γ-butyrolactone (5 atoms ester ring), δ-valerolactone (6 atoms ester ring) or ε-caprolactone (7 atoms ester ring); wherein each is optionally substituted by one or more halogen, hydroxyl, methoxy, fluorocarbon, amine, or thiol;

wherein at least one of B, $Q_1$, $Q_2$, $L_1$, $L_2$ and $L_3$ is conjugated to a drug as defined in Formula (I).

In some embodiments of the invention, y=1, z=o and w=0; or y=1, z=1 and w=0.

The Conjugates according to embodiments of the invention have the general Formula (I) and can be delivered across biological membranes into the cell:

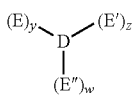

Formula (I)

including pharmaceutically acceptable, salts, hydrates, solvates and metal chelates of the compound represented by the structure as set forth in Formula (I), and solvates and hydrates of the salts, wherein:

D is a drug to be delivered across biological membranes. D may be a small-molecule drug, a peptide, a protein, or a native or modified, single-stranded or double-stranded DNA or RNA, such as, antisense oligonucleotide (ASO) or siRNA;

y, z and w are each an integer, independently selected from 0, 1, 2, 3, 4, 5, 6, wherein whenever the integer is 0, it means that the respective E moiety is null; at least one of y, z, or w is different from 0. In one embodiment, y=1, z=o, and w=0; in another embodiment y=1, z=1 and w=0.

E, E' or E" can be the same or different, each having the structure as set forth in general Formula (II):

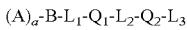

Formula (II)

wherein each A moiety is independently selected from the structures as set forth in Formulae (III), (IV), (V) and (VI):

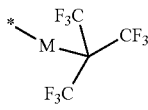

Formula (III)

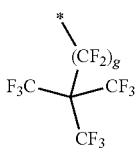

Formula (IV)

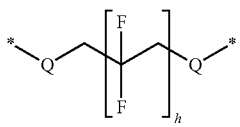

Formula (V)

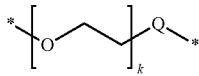

Formula (VI)

M is selected from —O— or —$CH_2$—; and g, h and k are each individually an integer selected from the group consisting of 0, 1, 2, 3, 4, 5, 6, 7, 8, 9, 10, 11, 12, 13, 14, 15 and 16; * is —H, or a point of linkage to B, or to another A group; a is an integer, selected from 1, 2, 3 or 4; Q is oxygen or amine.

B is selected from one or more of the groups consisting of:
linear, cyclic or branched $C_1$, $C_2$, $C_3$, $C_4$, $C_5$, $C_6$, $C_7$, $C_8$, $C_9$, $C_{10}$, $C_{11}$, $C_{12}$, $C_{13}$ or $C_{14}$, alkyl or hetero-alkyl, wherein each is optionally substituted by one or more halogen, hydroxyl, methoxy, fluorocarbon, amine or thiol; or optionally linked to an ether, an ester, or an amide group;

linear, cyclic or branched $C_2$, $C_3$, $C_4$, $C_5$, $C_6$, $C_7$, $C_8$, $C_9$, $C_{10}$, $C_{11}$, $C_{12}$, $C_{13}$ or $C_{14}$ alkylene or heteroalkylene, wherein each in optionally substituted by one or more halogen, hydroxyl, methoxy, fluorocarbon, amine or thiol; or optionally linked to an ether, an ester, or an amide group;

$C_5$, $C_6$, $C_7$, $C_8$, $C_9$, $C_{10}$, $C_{11}$, $C_{12}$, $C_{13}$ or $C_{14}$ aryl or heteroaryl, wherein each is optionally substituted by one or more halogen, hydroxyl, methoxy, fluorocarbon, amine or thiol; or optionally linked to an ether, an ester, or an amide group;

one or more steroid moiety (such as cholesterol, bile acid, estradiol, estriol), estrogen, nucleoside, nucleotide; and any combination thereof, wherein each is optionally substituted by one or more halogen, hydroxyl, methoxy, fluorocarbon, amine or thiol; or each is optionally linked to an ether, an ester, an amine, or an amide group;

or any combination thereof;

$Q_1$ and $Q_2$ are each a cleavable group, independently selected from null, ester, thio-ester, amide [e.g., —C(=O)—NH— or —NH—C(=O)—], carbamate [e.g., —O—C(=O)—NH— or —NH—C(=O)—O—], urea [—NH—C(=O)—NH—], disulfide [—(S—S)—], ether [—O—], amine, imidazole, triazole, dilactone, a pH-sensitive moiety, a redox-sensitive moiety; a metal chelator, including its chelated metal ion; and any combinations thereof;

$L_1$, $L_2$ and $L_3$ are each independently selected from null and the group consisting of linear, cyclic or branched $C_1$, $C_2$, $C_3$, $C_4$, $C_5$, $C_6$, $C_7$, $C_8$, $C_9$, $C_{10}$, $C_{11}$, $C_{12}$, $C_{13}$, or $C_{14}$, alkyl or hetero-alkyl, wherein each is optionally substituted by one or more halogen, hydroxyl, methoxy, fluorocarbon, amine, or thiol; or linked to an ether group;

linear, cyclic or branched $C_2$, $C_3$, $C_4$, $C_5$, $C_6$, $C_7$, $C_8$, $C_9$, $C_{10}$, $C_{11}$, $C_{12}$, $C_{13}$ or $C_{14}$ alkylene or heteroalkylene, wherein each is optionally substituted by one or more halogen, hydroxyl, methoxy, fluorocarbon, amine, thiol, or linked to an ether group;

$C_5$, $C_6$, $C_7$, $C_8$, $C_9$, $C_{10}$, $C_{11}$, $C_{12}$, $C_{13}$ or $C_{14}$ aryl or heteroaryl, wherein each is optionally substituted by one or more halogen, hydroxyl, methoxy, fluorocarbon, amine, thiol; or linked to an ether group;

—(O—$CH_2$—$CH_2$)$_u$—, wherein each is optionally substituted by one or more halogen, hydroxyl, methoxy, fluorocarbon, amine, or thiol;

nucleoside, nucleotide; imidazole, azide, acetylene; and any combinations thereof, wherein each is optionally substituted by one or more halogen, hydroxyl, methoxy, fluorocarbon, amine, thiol; or linked to an ether group; and wherein u is an integer of 1, 2, 3, 4 or 5; and any combinations thereof;

wherein at least one of $Q_1$, $Q_2$, $L_1$, $L_2$ and $L_3$ is not null; and wherein each of $Q_1$, $Q_2$, $L_1$, $L_2$ and $L_3$ is optionally substituted by T; wherein T is an initiator group, selected from $C_5$, $C_6$, $C_7$—1,2-dithiocycloalkyl (1,2-dithiocyclo-pentane, 1,2-dithiocyclohexane, 1,2-dithiocyclo-heptane); γ-Lactam (5 atoms amide ring), δ-Lactam (6 atoms amide ring) or ε-Lactam (7 atoms amide ring); γ-butyrolactone (5 atoms ester ring), δ-valerolactone (6 atoms ester ring) or ε-caprolactone (7 atoms ester ring); wherein each of the initiator group is optionally substituted by one or more halogen, hydroxyl, methoxy, fluorocarbon, amine, or thiol; wherein at least one of B, $Q_1$, $Q_2$, $L_1$, $L_2$ and $L_3$ is conjugated to a drug as defined in Formula (I).

In an embodiment of the invention, it provides that at least two of $Q_1$, $Q_2$, $L_1$, $L_2$ and $L_3$ are not null;

In an embodiment of the invention, it provides that at least three of $Q_1$, $Q_2$, $L_1$, $L_2$ and $L_3$ are not null;

In an embodiment of the invention, it provides a Conjugate according to General Formula (I), where at least one of E, E' or E" has the structure as set forth in Formula (VIIIg), or Formula (XId):

Another embodiment, relates to method for treating a medical disorder in a patient in need; the method comprises administration to the patient therapeutically efficient amounts of a pharmaceutical composition that comprises a Conjugate as described herein.

In some embodiments of the invention, the medical disorder is cancer.

BRIEF DESCRIPTION OF THE FIGURES

The patent or application file contains a least one drawing executed in color. Copies of this patent or patent application publication with color drawings will be provided by the Office upon request and payment of the necessary fee.

The invention will now be described in connection to certain Examples and embodiments, in a non-limiting man-

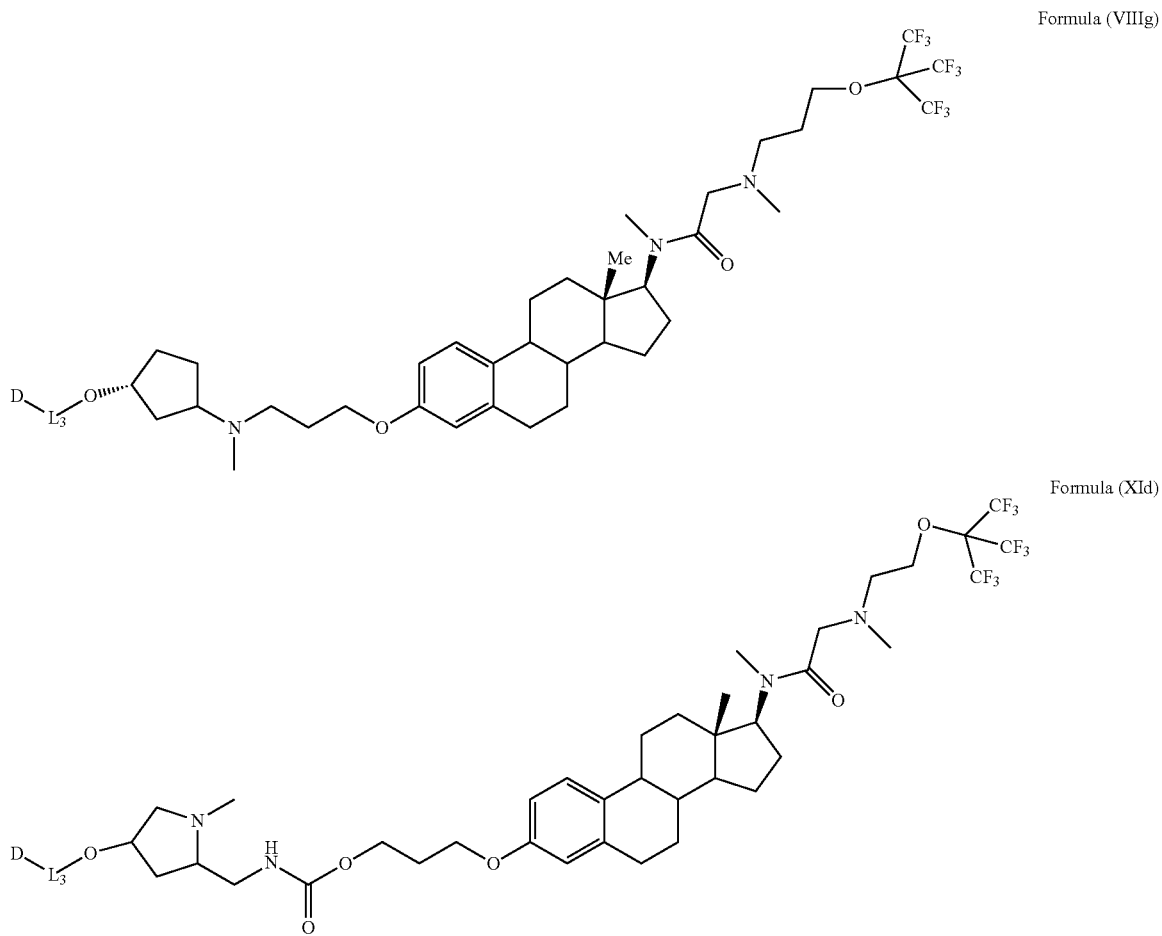

Formula (VIIIg)

Formula (XId)

Figure 1A:
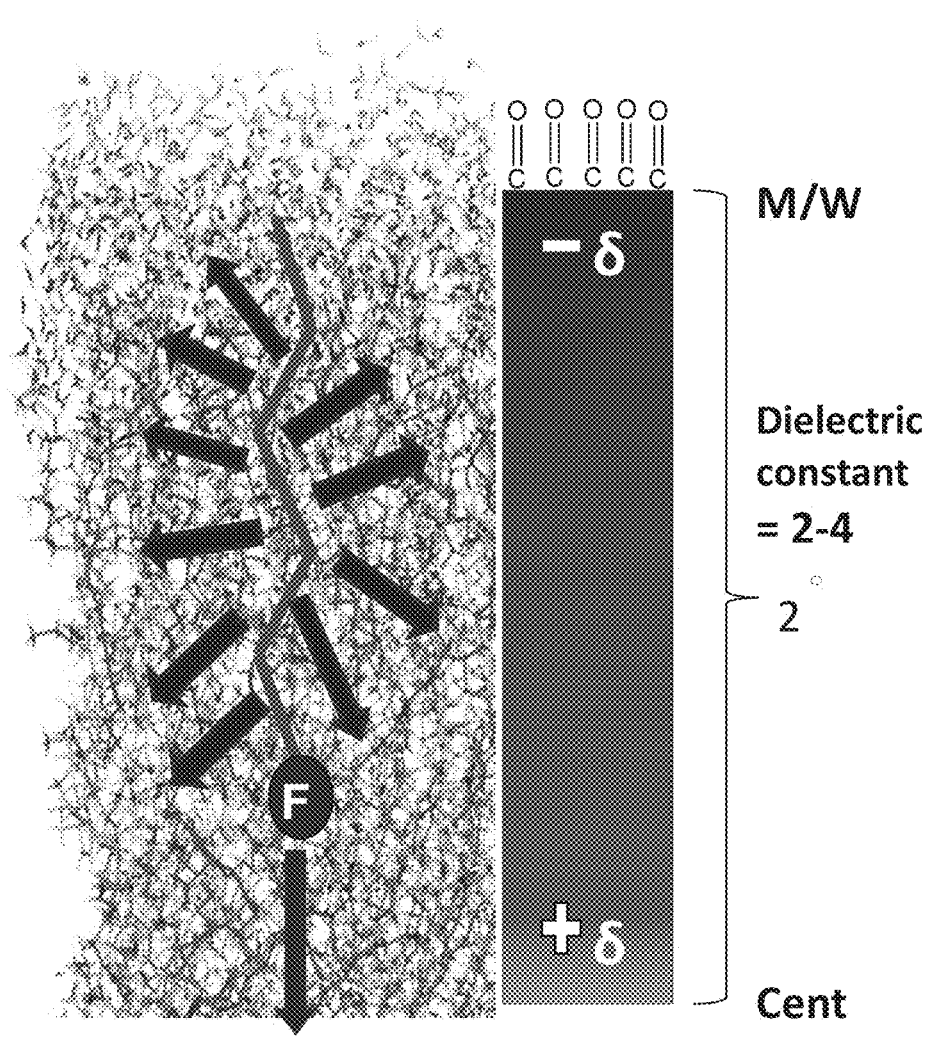

including pharmaceutically acceptable salts, hydrates, solvates and metal chelates of the compound represented by the structure as set forth in Formula (VIIIg) or Formula (XId), and solvates and hydrates of the salts; wherein D is a drug, as defined in Formula (I); and $L_3$ is selected from null and $C_1$, $C_2$, $C_3$, $C_4$, $C_5$, or $C_6$ alkylene.

Some embodiments of the invention relate to a method for delivery of a drug across biological membrane into cells, either in vitro or in vivo, the method comprising contacting the cells with a Conjugate as described herein.

ner, with reference to the following illustrative figures, so that it can be more fully understood. In the drawings:

FIG. 1A is a schematic presentation of the principle of asymmetrical polarity, underlying the putative Mechanism of Action (MOA) compounds according to embodiments of the invention; The molecule has a negative pole, with electronegative atom(s), e.g., fluorine atom(s), and a positive pole, comprising hydrocarbon chains, interacting via hydrophobic interactions with the adjacent chains of the phospholipid molecules. Consequently, the molecule, while being in overall hydrophobic and uncharged, has a focused, discrete partial negative charge, while by contrast, the partial positive charge is dispersed and masked. This leads to movement of the molecule, from the membrane surface to the membrane center.

Figure 1B:
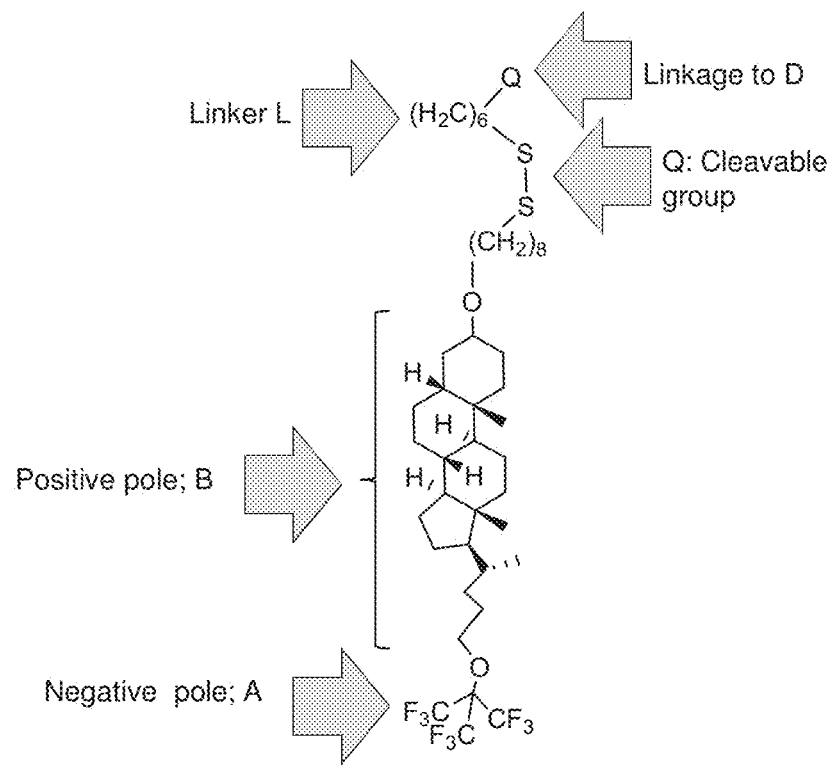

FIG. 1B schematically depicts structural motifs of the molecules of the invention, as exemplified by a compound according to Formula (IXb), wherein $Q_1$ is —S—S—; and $Q_2$ is null; a=6; b=8; and the steroid moiety is a residue of a lithocholic acid.

Figure 2A:
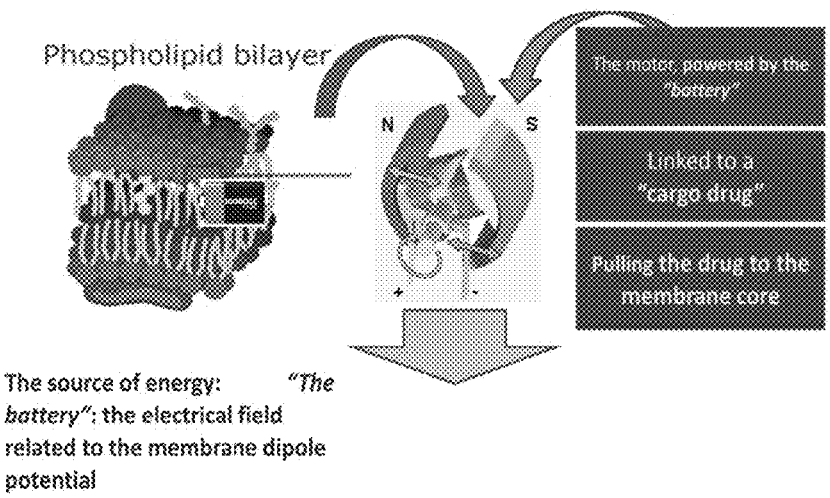
Figure 2B:
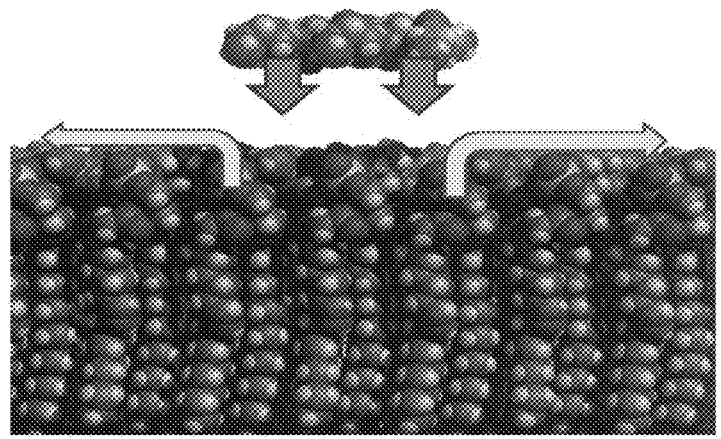
Figure 2C:
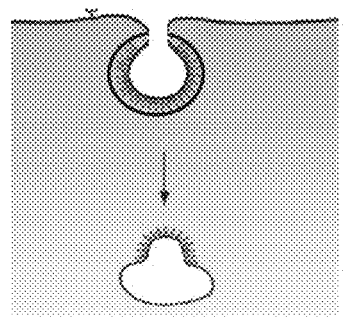

FIGS. 2A-2C schematically illustrates a putative MOA of a conjugate according to embodiments of the invention: FIGS. 2A-2C shows a "Molecular NanoMotor (MNM)", energized by the internal membrane electric field, which relates to the membrane dipole potential; FIG. 2B shows the forced adduction of the macromolecule to the membrane surface, induced by the MNM, thereby perturbing the phospholipid hydration shells, and forcing lateral movement of phospholipid head-groups; FIG. 2C demonstrates consequent induction of flip-flop of the Conjugate and endocytosis, with movement of the conjugate into endosomes; eventually, there is flip-flop of the conjugate between the leaflets of the endosomal membrane, to generate inter-leaflet concentration equilibration; Subsequently, there is movement of the Conjugate from the endosomal membrane into the cytoplasm, driven by concentration gradient, and by performance enhancing moieties (PEM) as described herein.

Figure 3A:
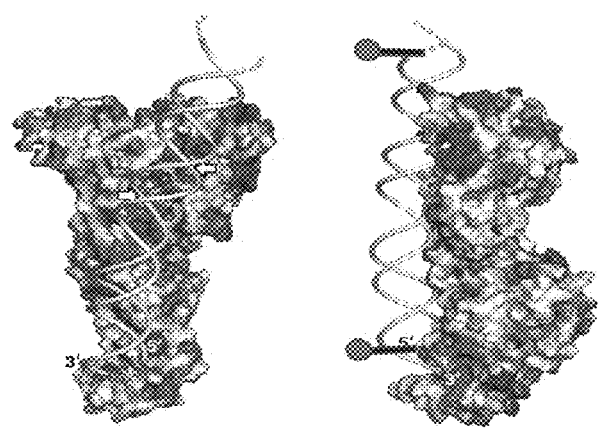
Figure 3B:
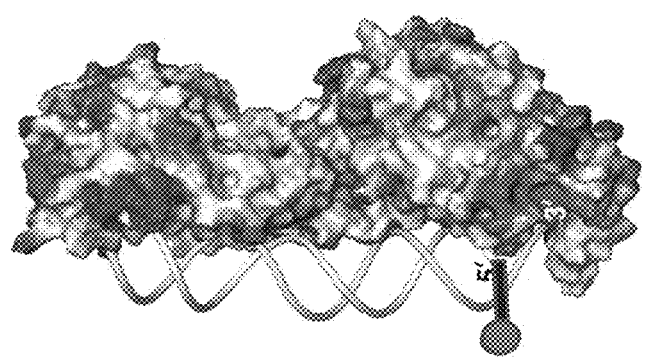

FIGS. 3A-3B schematically illustrates a mechanism for entrapment of siRNA within the cytoplasm, utilizing the Dicer enzyme, to cleave and remove the MNM; FIG. 3A demonstrates docking of siRNA, linked to two Apo-Si MNMs on the Dicer protein; FIG. 3B show the removal of one motor by enzyme-mediated RNA cleavage. Subsequently. Hellicase/Agronaute acts to separate the RNA strands, releasing the Guide/Sense strand to interact with RNA-inducible silencing complex (RISC), in order to exert gene silencing, while the passenger strand, to which the second MNM is still attached, is destined to degradation.

Figure 4:
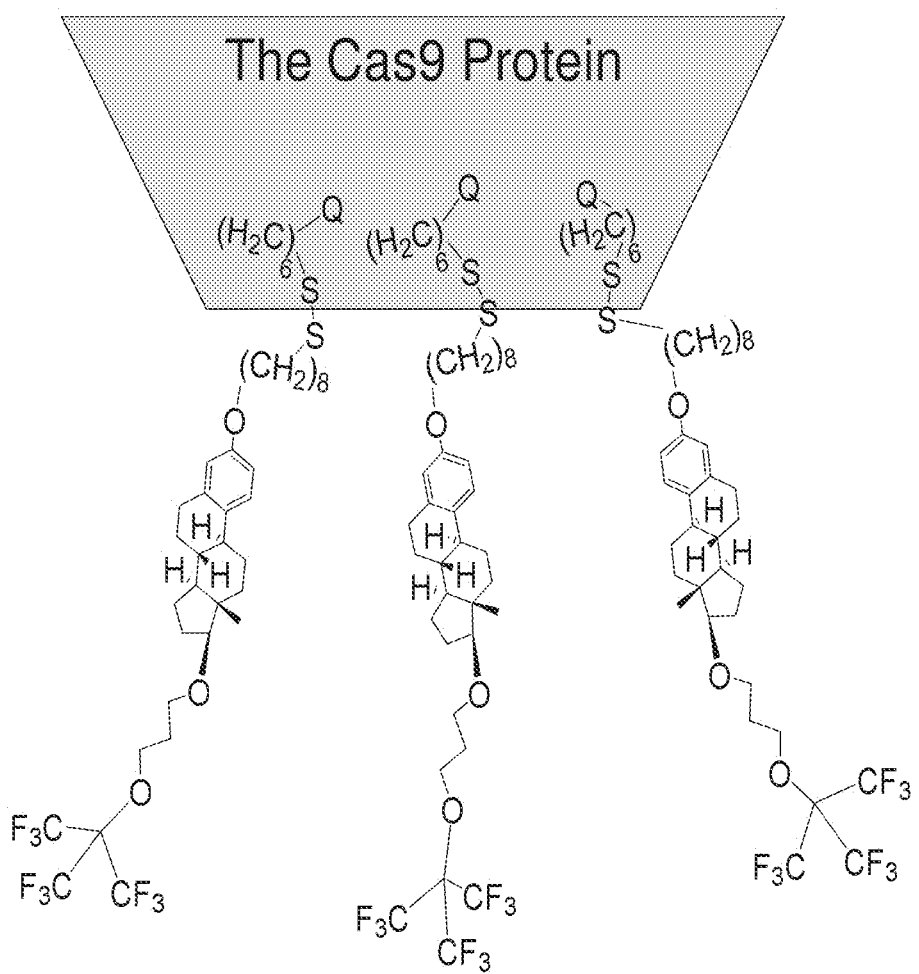

FIG. 4 shows an exemplary structure of a Conjugate of the invention, comprising a protein (for example without limitation Cas9) and E, E', E" moieties, as set forth Formula I;

FIGS. 5A-5F, 6A-6C, and 7-9A-9D exemplify the biological performance in vitro of conjugates, according to embodiments of the invention, comprising MNMs of the invention, having the structure as set forth in either Formula (VII) or Formula (VIIa); Apo-Si-11 or Apo-Si-C4, respectively.

Figure 5A:
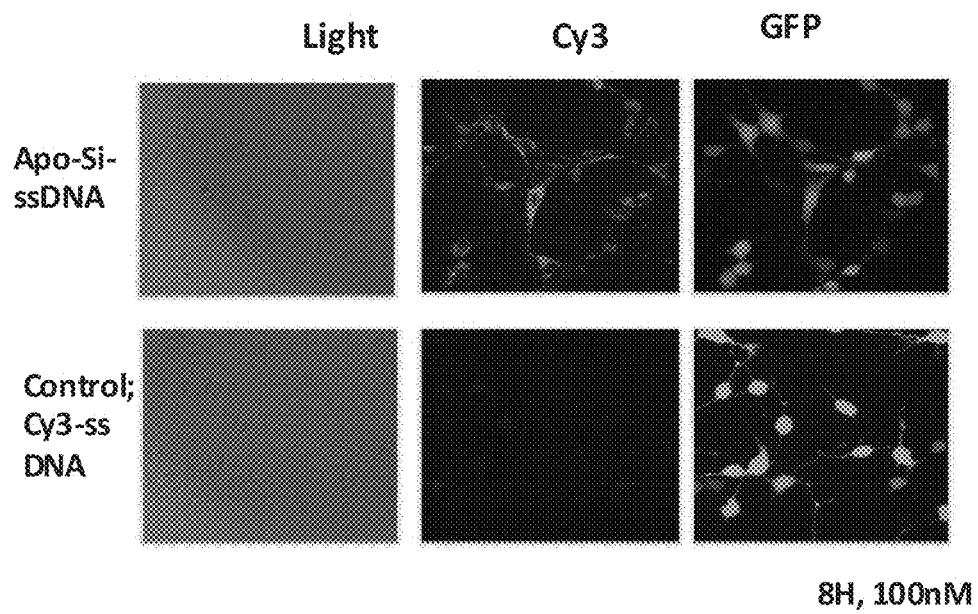
Figure 5B:
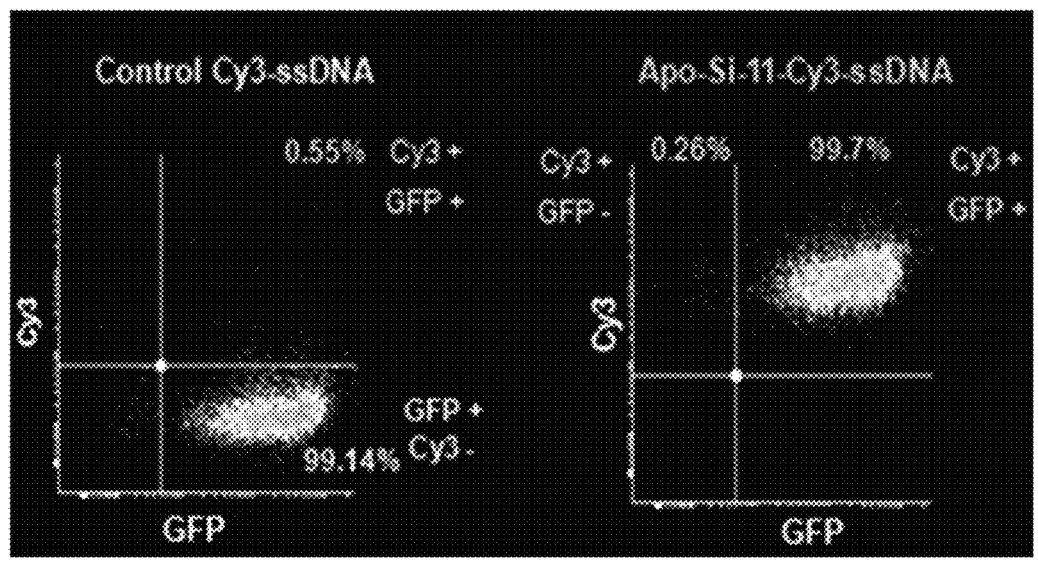
Figure 5C:
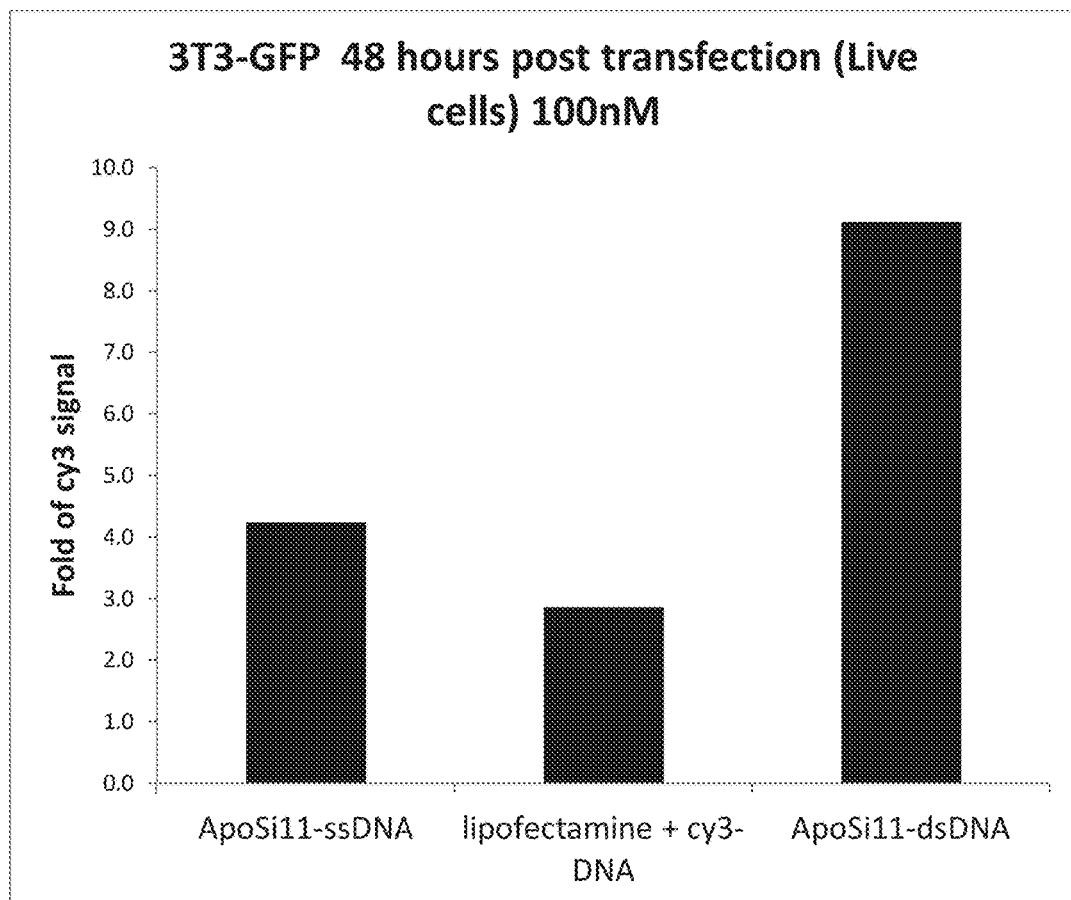
Figure 5D:
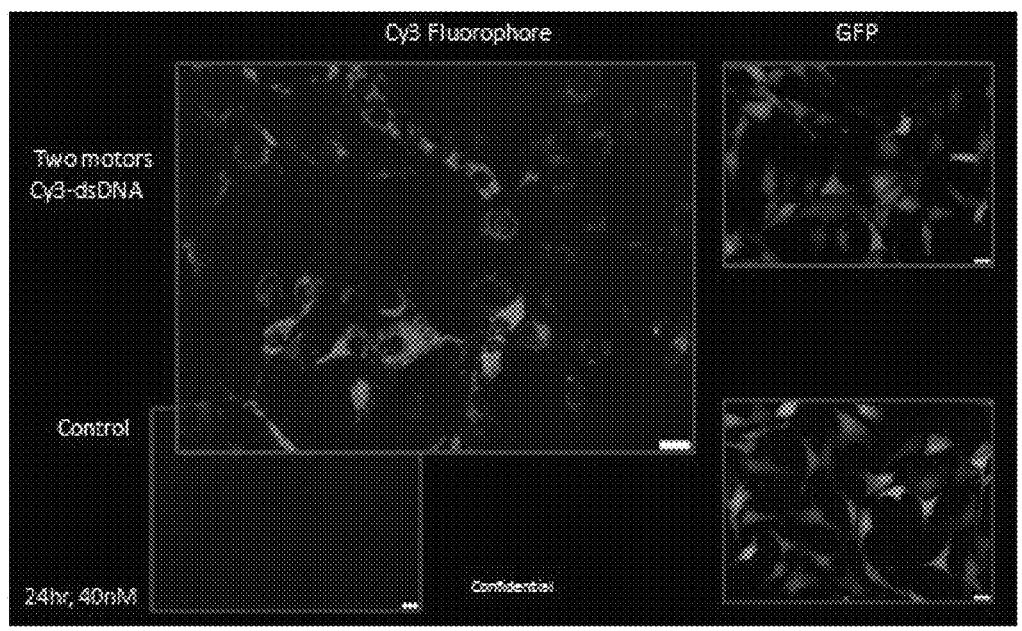
Figure 5E:
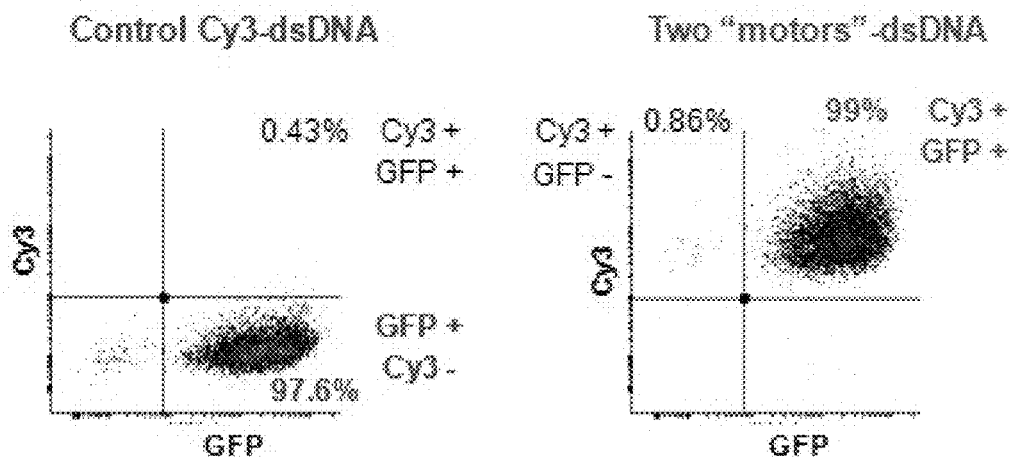
Figure 5F:
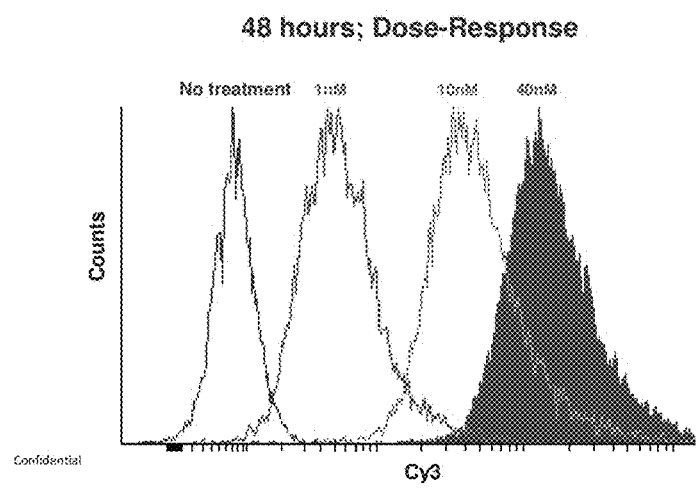
Figure 5G:
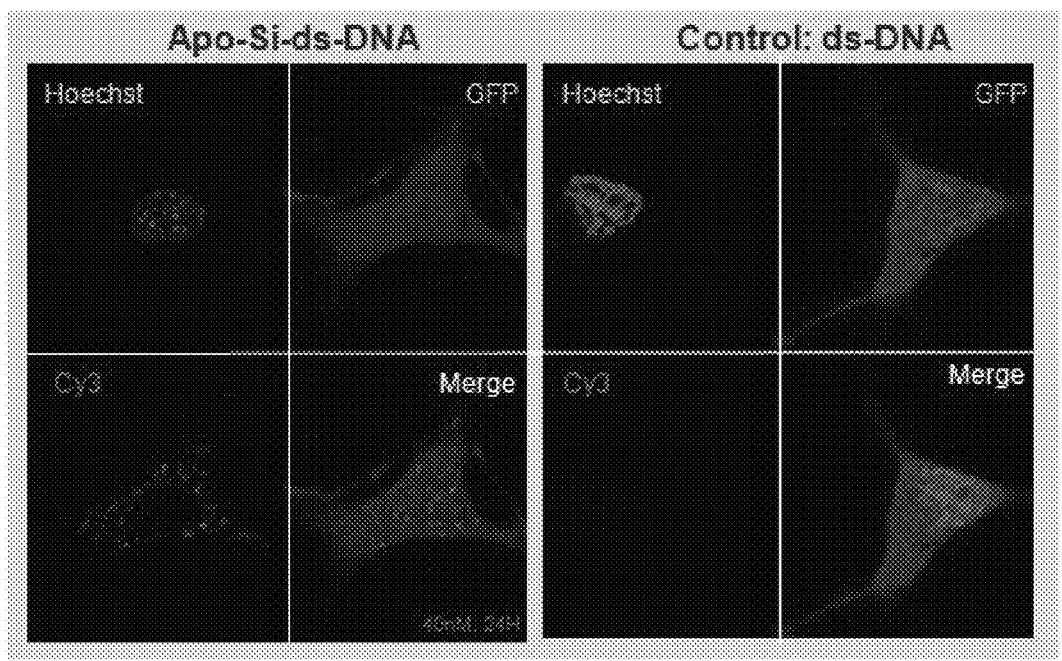

FIG. 5A-5: 3T3-cells:

FIG. 5A shows fluorescent microscopy of delivery of a Conjugate, comprising, a 29-mer, single-stranded DNA (ss-DNA) across biological membranes of 3T3 cells, expressing the EGFP Protein (3T3-EGFP cells) in vitro;

FIG. 5B shows quantification of the delivery as described in FIG. 5A by flow cytometric analysis (FACS), presented as a dot plot;

FIG. 5C shows quantification using ELISA reader, of the delivery as described in FIG. 5A, at 24 hours of incubation;

FIG. 5D shows fluorescent microscopy of delivery of a conjugate, comprising a 58-mer double-strand DNA (ds-DNA) across biological membranes of 3T3 cells, expressing the EGFP Protein (3T3-EGFP cells) in vitro;

FIG. 5E shows quantification of the delivery, as described in FIG. 5D, by flow cytometric analysis (FACS): FIG. 5E (left and tight) Dot plot; FIG. 5F represents The histogram;

FIG. 5G presents confocal microscopy, showing delivery as described in FIG. 5D into the endosomal compartment, as per the Mechanism of Action of the Invention.

Figure 6A:
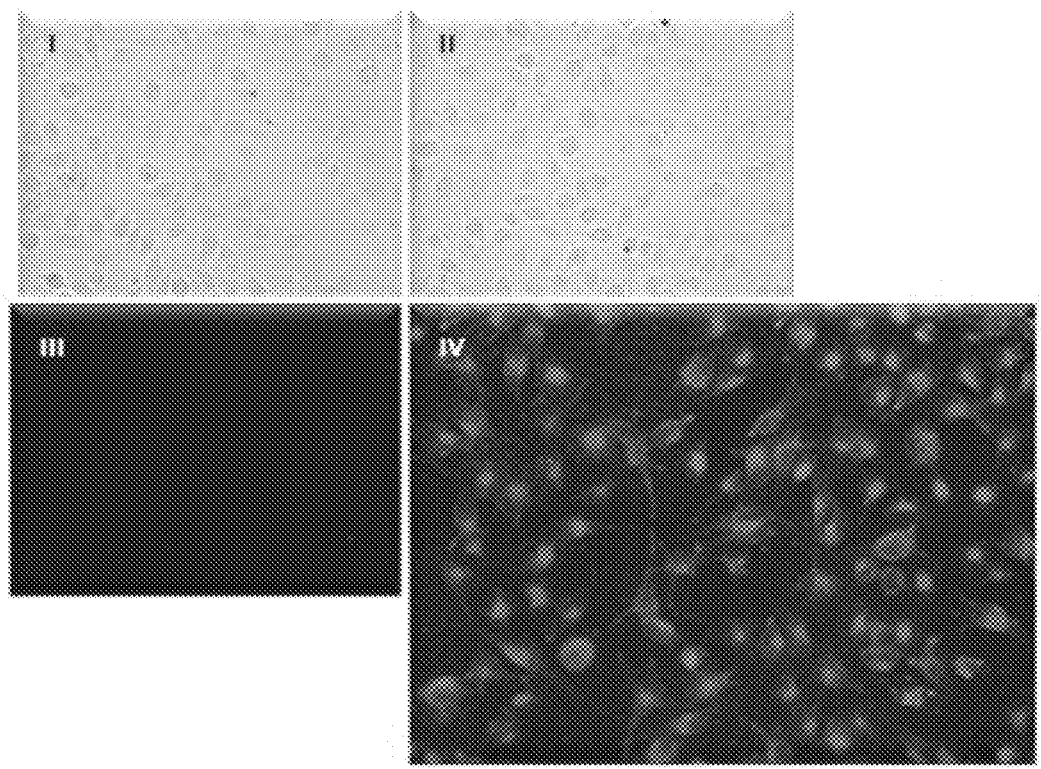
Figure 6B:
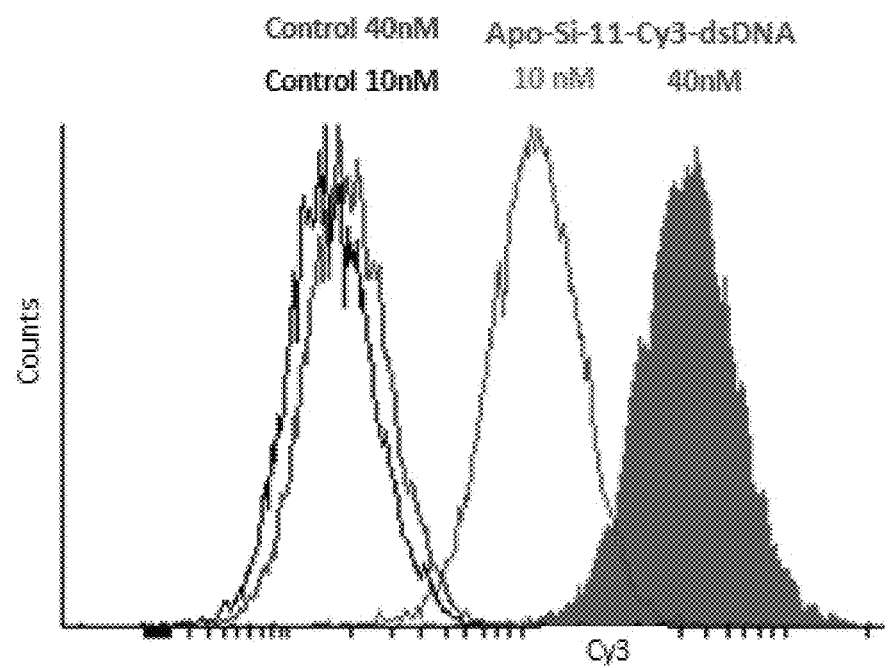
Figure 6C:
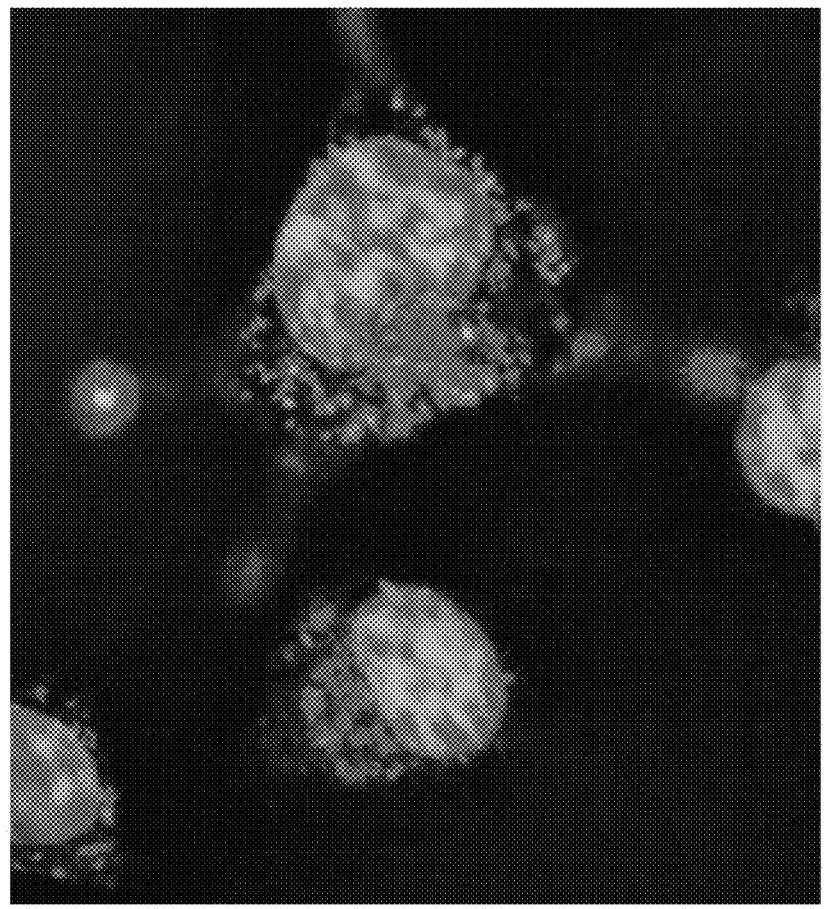

FIG. 6A-6C: Marine melanoma B16 cells:

FIG. 6A presents fluorescent microscopy, of the delivery of a Conjugate of the invention, comprising a 58-mer double-stranded DNA, labeled with the Cy3 fluorophore (red) across biological membranes of B16 melanoma cells in vitro: (I), (II). Bright field, delineating cell contour; (III). Fluorescent signal from DNA without the MNMs; (IV). Fluorescent signal from a Conjugate comprising MNMs;

FIG. 6B shows quantification of the delivery as described in FIG. 6A by flow cytometric analysis (dose/response);

FIG. 6C shows delivery as described in FIG. 6A, detected by confocal microscopy, demonstrating the delivery of the conjugate, comprising a 58-mer double-strand DNA, is into the endosomal compartment of the B16 cells.

Figure 7:
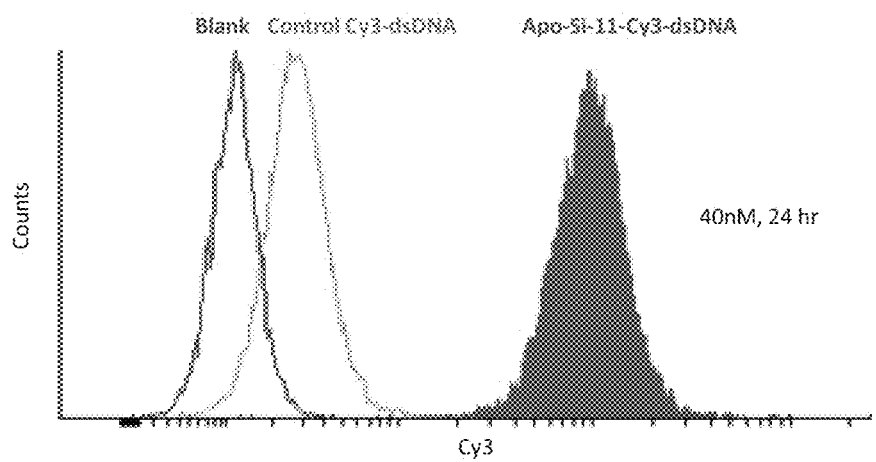

FIG. 7: Murine C26 colon carcinoma cells:

Flow cytometric analysis of the delivery of a Conjugate of the Invention, comprising a 58-mer double-stranded DNA, across the biological membranes of C26 cells in vitro.

Figure 8:
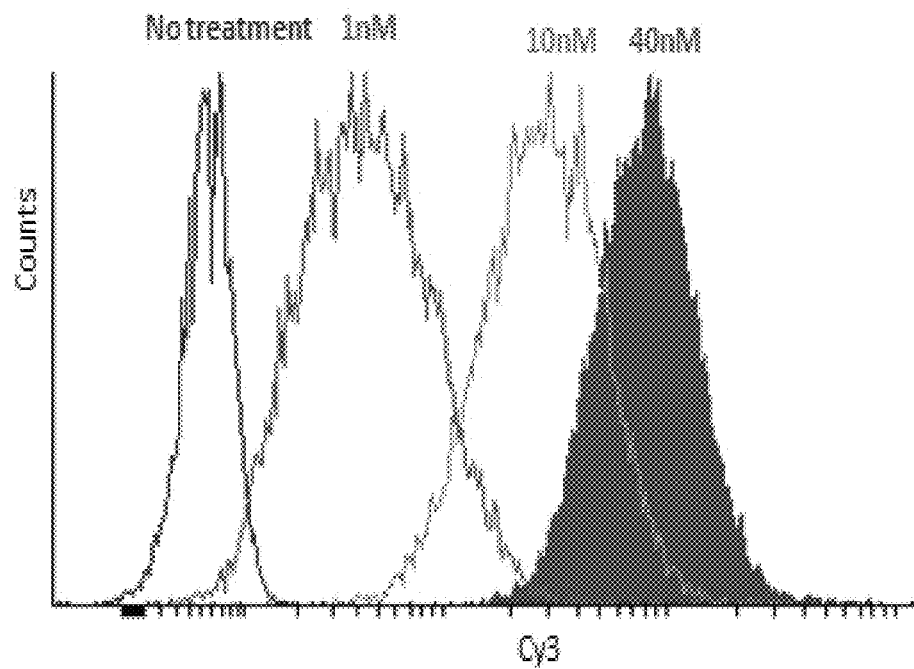

FIG. 8: HeLa cells:

Flow cytometric analysis, of the delivery of a Conjugate of the Invention, comprising a 58-mer double-stranded DNA across the biological membranes of HeLa cells in vitro; dose/response.

FIGS. 9A-9D describes gene silencing (EGFP gene), exerted in human HeLA cells in vitro, by a Conjugate of the invention, being a respective siRNA, specifically-designed to silence the EGFP gene linked to two MNMs, each having the structure as set forth in Formula (VIIIb); i.e., Apo-Si-W (mean±SEM).

Figure 10A:
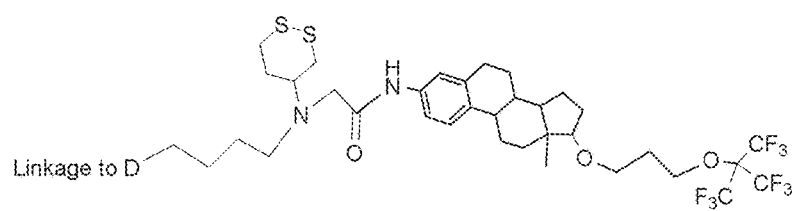
Figure 10B:
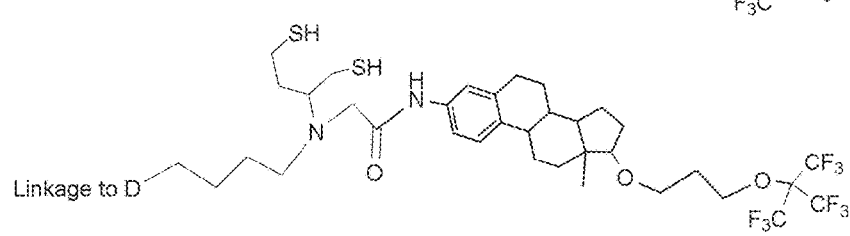
Figure 10C:
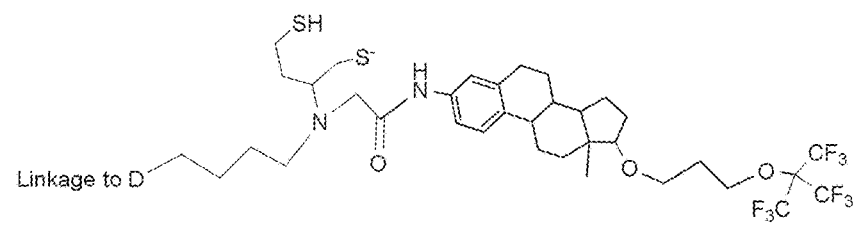
Figure 10D:
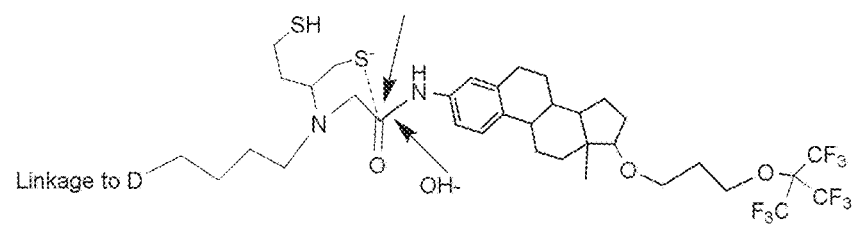
Figure 10E:
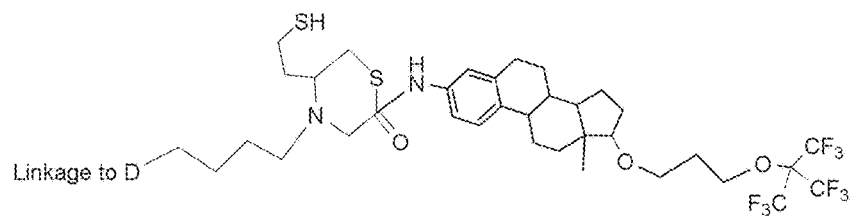
Figure 10F:
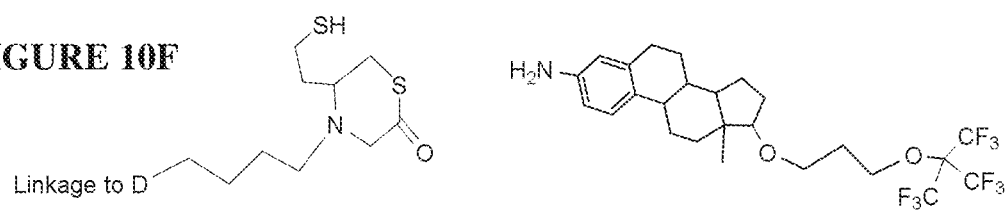
Figure 10G:
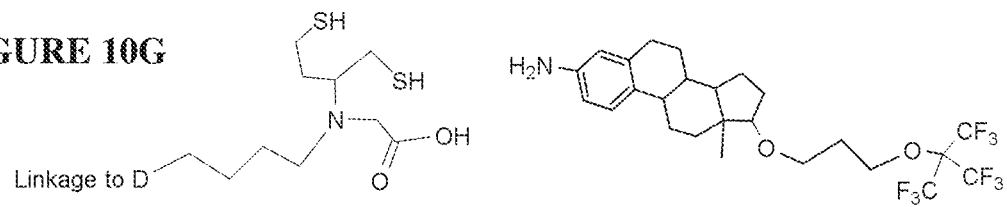
Figure 10H:
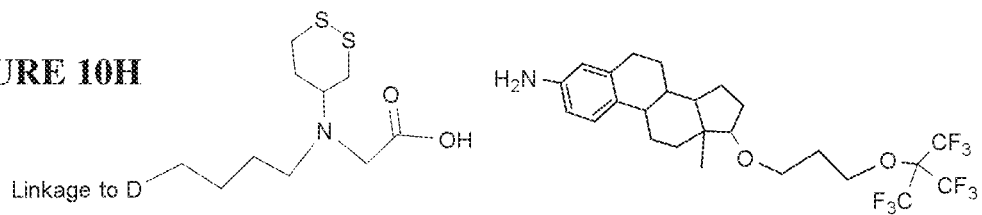

FIGS. 10A-10H exemplifies the Mechanism Of Action (MOA) of a compound according, to Formula (XVI) wherein FIG. 10A represents the intact Conjugate in the extracellular space; FIG. 10B represents the cleavage of the disulfide bond in the reductive cytoplasmatic milieu; FIG. 10C represents de-protonation of the thiol to thiolate, in a pKa-dependent process; FIG. 10D represents nucleophilic attack of the thiolate on the carbonyl moiety of the amide group; FIG. 10E represents generation of a tetrahedral intermediate; FIG. 10F represents the consequent cleavage of the Conjugate, with generation of a thioester; FIG. 10G represents subsequent hydrolysis; FIG. 10H represents ring closure and disulfide formation in the oxidative environment at the extracellular space during excretion form the body.

Figure 11A:
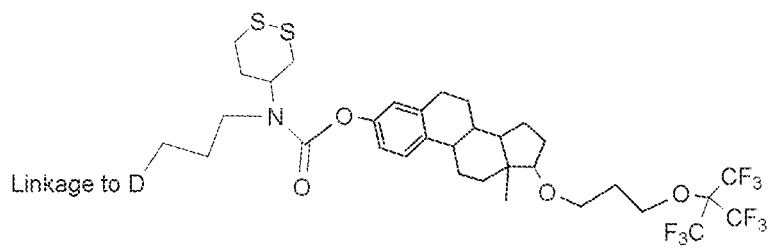
Figure 11B:
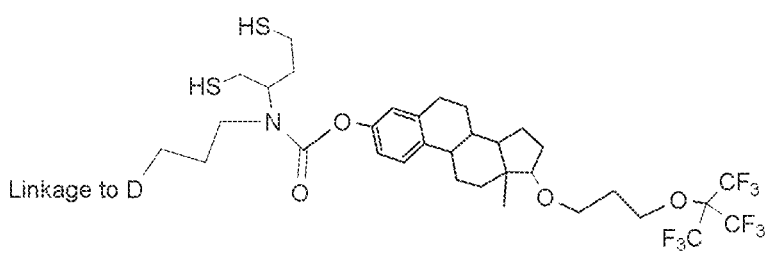
Figure 11C:
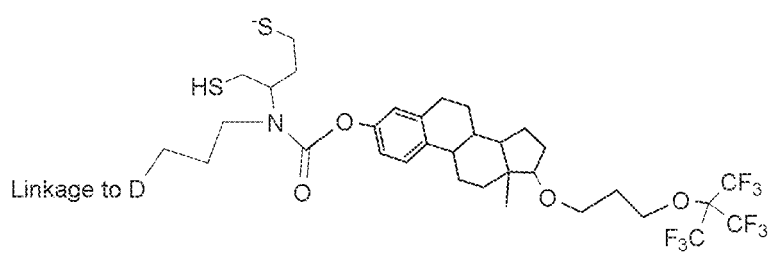
Figure 11D:
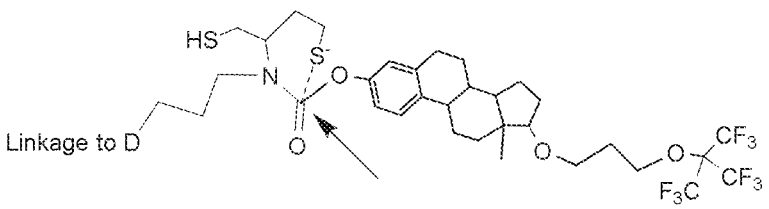
Figure 11E:
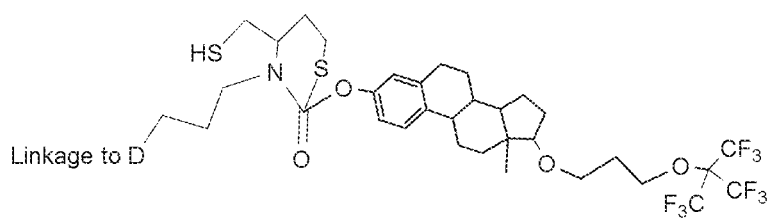
Figure 11F:
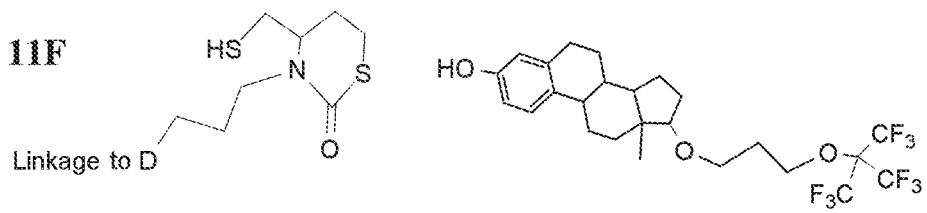
Figure 11G:
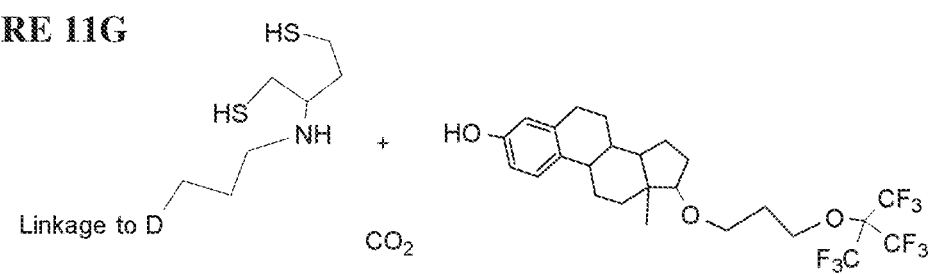
Figure 11H:
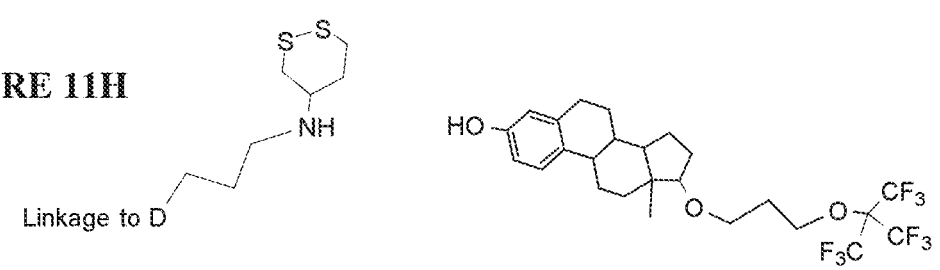

FIGS. 11A-11H exemplifies the Mechanism Of Action (MOA) of a compound according to Formula XVI where: FIG. 11A represents the intact Conjugate n the extracellular space; FIG. 11B represents the cleavage of the disulfide bond in the reductive cytoplasmatic milieu; FIG. 11C represents deprotonation of the thiol into thiolate, in a pka-dependent process; FIG. 11D represents nucleophilic attack of the thiolate on the carbonyl moiety of the amide group; FIG. 11E represents generation of a tetrahedral intermediate; FIG. 11F represents the consequent cleavage of the Conjugate, with generation of a thio-ester; FIG. 11G represents subsequent hydrolysis; FIG. 11H represents ring closure and disulfide formation in the oxidative environment at the extracellular space during excretion form the body.

Figure 12:
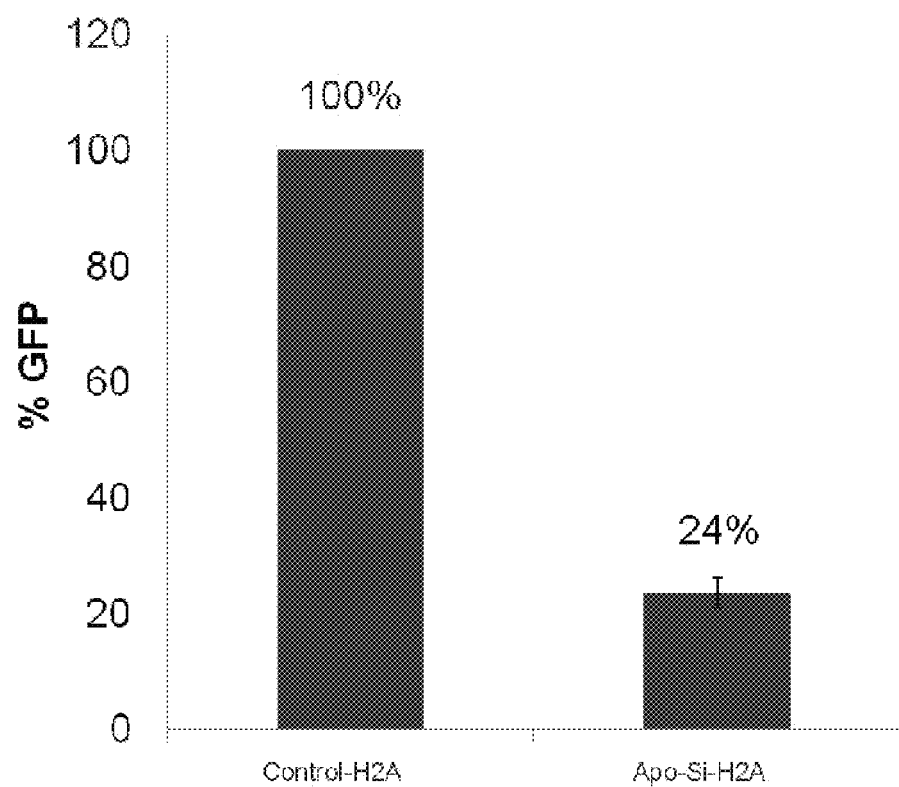

FIG. 12 describes gene silencing, exerted in a primary culture of hepatocytes of transgenic mouse expressing the EGFP gene, by a Conjugate of the invention, being a respective siRNA, specifically-designed to silence the EGFP gene, linked to two Apo-Si-C4 MNMs (mean±SEM).

Figure 13A:
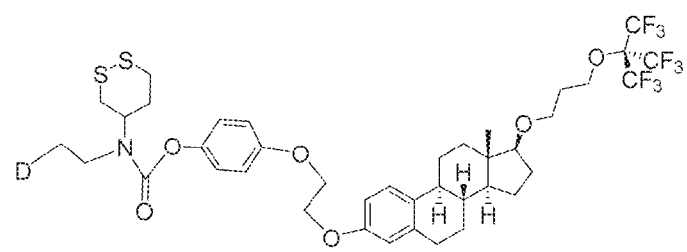
Figure 13B:
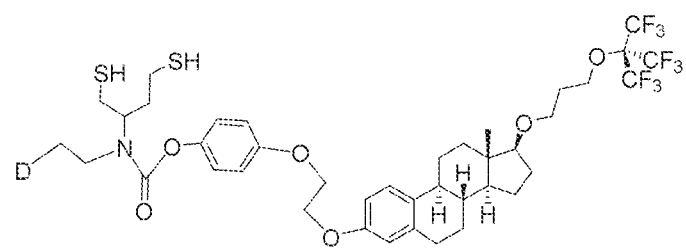
Figure 13C:
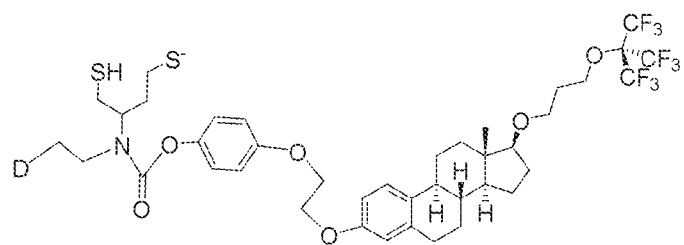
Figure 13D:
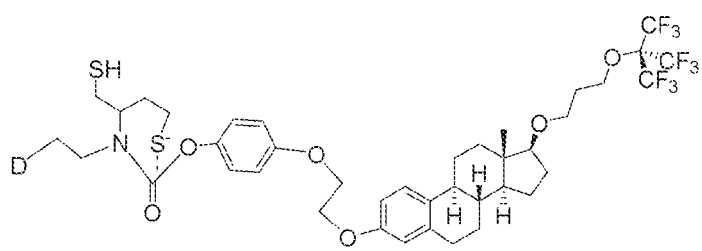
Figure 13E:
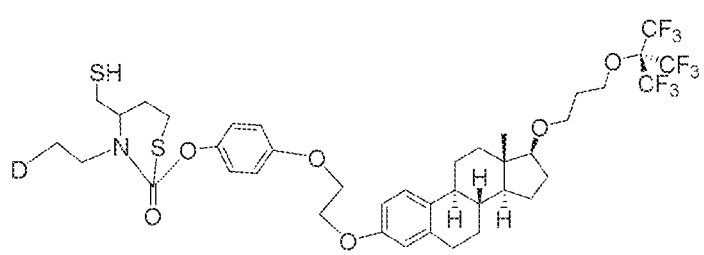
Figure 13F:
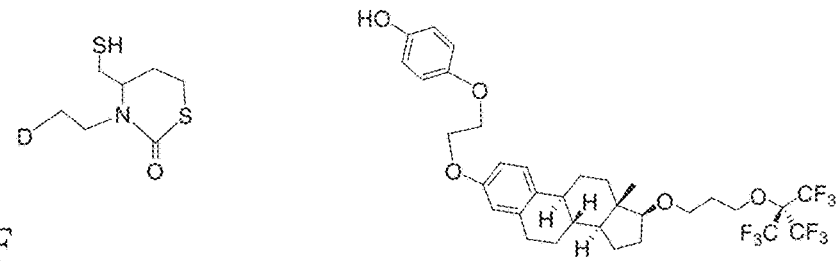
Figure 13G:
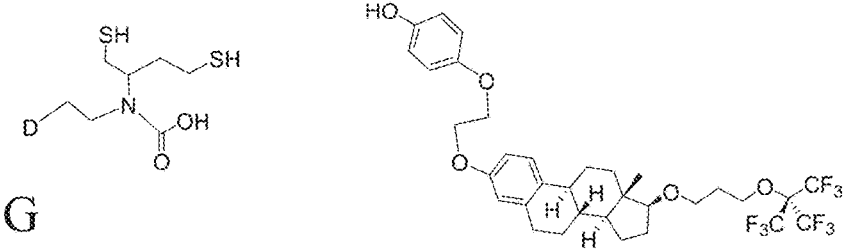
Figure 13H:
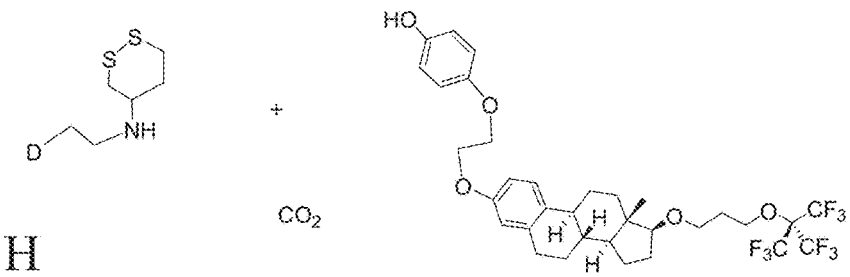

FIGS. 13A-13H exemplifies the Mechanism Of Action (MOA) of a compound according to Formula (VII), designated Apo-Si-X-1; where: FIG. 13A represents the intact Conjugate in the extracellular space; FIG. 13B represents the cleavage of the disulfide bond in the reductive cytoplasmatic milieu; FIG. 13C represents de-protonation of the thiol into thiolate, in a pKa-dependent process; FIG. 13D represents nucleophilic attack of the thiolate on the carbonyl moiety of the amide group; FIG. 13E represents generation of a tetrahedral intermediate; FIG. 13F represents the consequent cleavage of the Conjugate, with generation of a thio-ester; FIG. 13G represents subsequent hydrolysis, also with release of $CO_2$; and FIG. 13H represents ring closure with formation of a disulfide group, encountered in the oxidative environment at the extracellular space, during excretion of the MNM from the body.

Figure 14A:
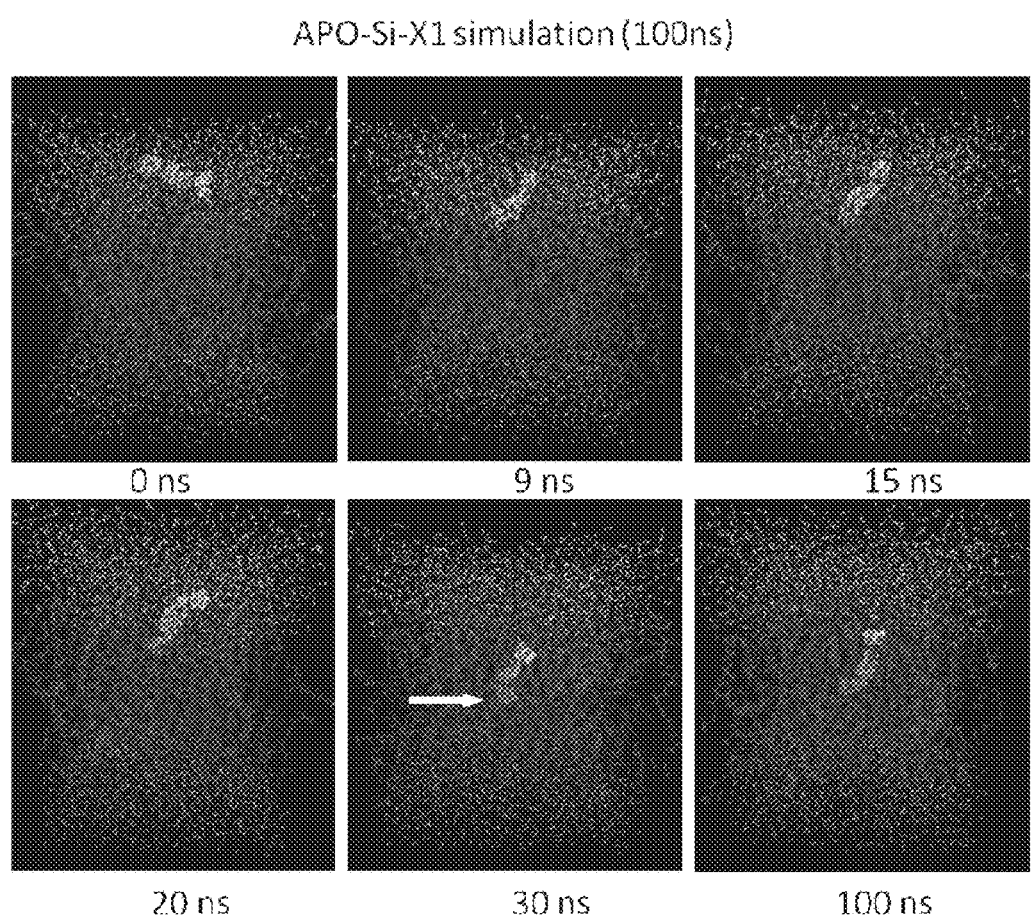
Figure 14B:
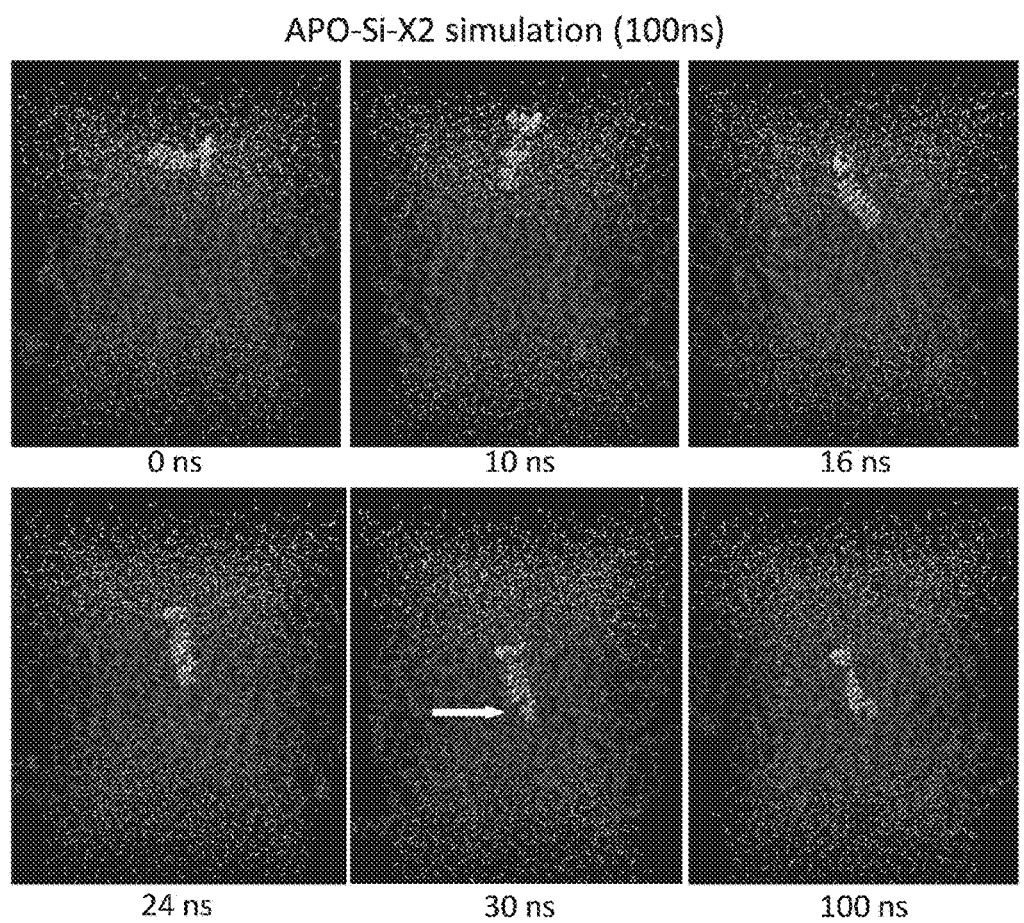
Figure 14C:
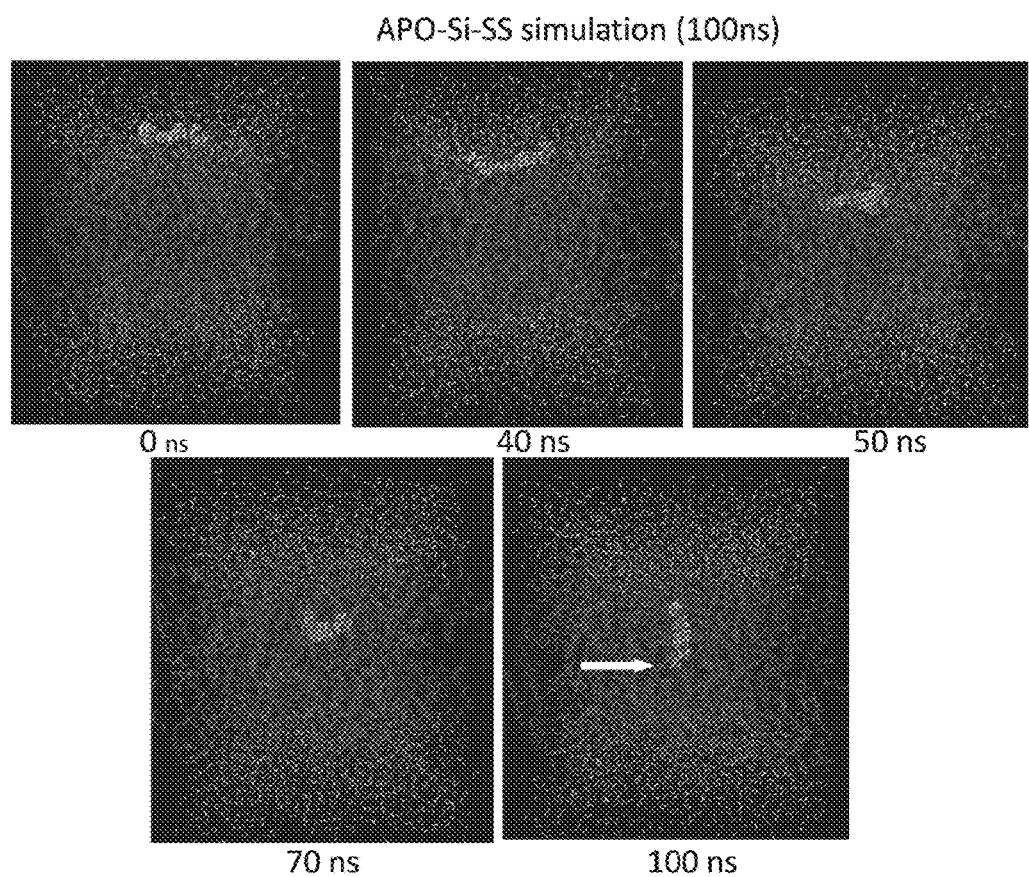
Figure 15A:
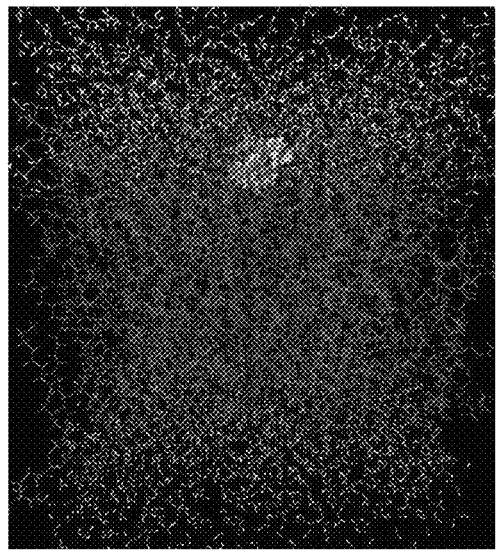
Figure 15B:
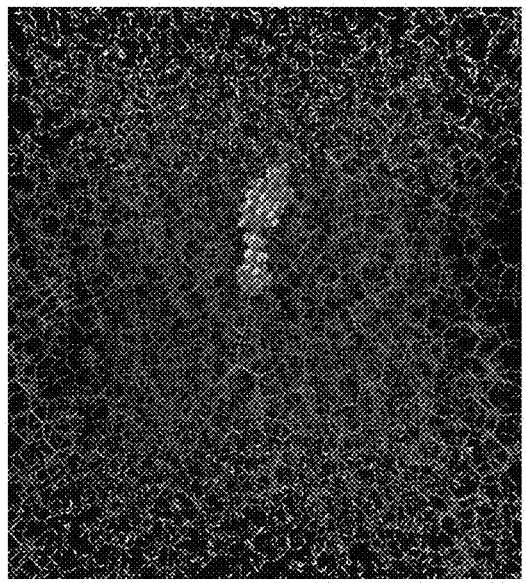

FIGS. 14A-14C demonstrates the interactions of E moieties of the Invention with phospholipid membranes in a Molecular Dynamics (MD) study; FIG. 14A a compound according to Formula (VII), designated Apo-Si-X-1; FIG. 14B a compound according to Formula (VII), designated Apo-Si-X-2; and FIG. 14C shows a compound according to Formula IXb designated Apo-Si-S-S:

FIGS. 15A-15B illustrates, via computerized molecular simulation studies, the principle of dynamic protonation. Pending on the protonation state of the tertiary amine of the MNM, are provided both a water-soluble form of the molecule, wherein the tertiary nitrogen is protonated (positively charged), and consequently is capable of moving within the blood plasma or cytoplasm; and a water-insoluble form, wherein the nitrogen is at an uncharged state, thus being capable of moving within the cell membrane milieu. The concerted distribution of these two forms in vivo, may lead to an integral large volume of distribution of the Conjugate within the body. FIG. 15A shows a protonated, positively-charged form of the molecule of the invention, excluded from the membrane; FIG. 15B shows A hydrophobic, unprotonated form of the molecule, that partitions and moves into the core of the phospholipid membrane.

Figure 16:
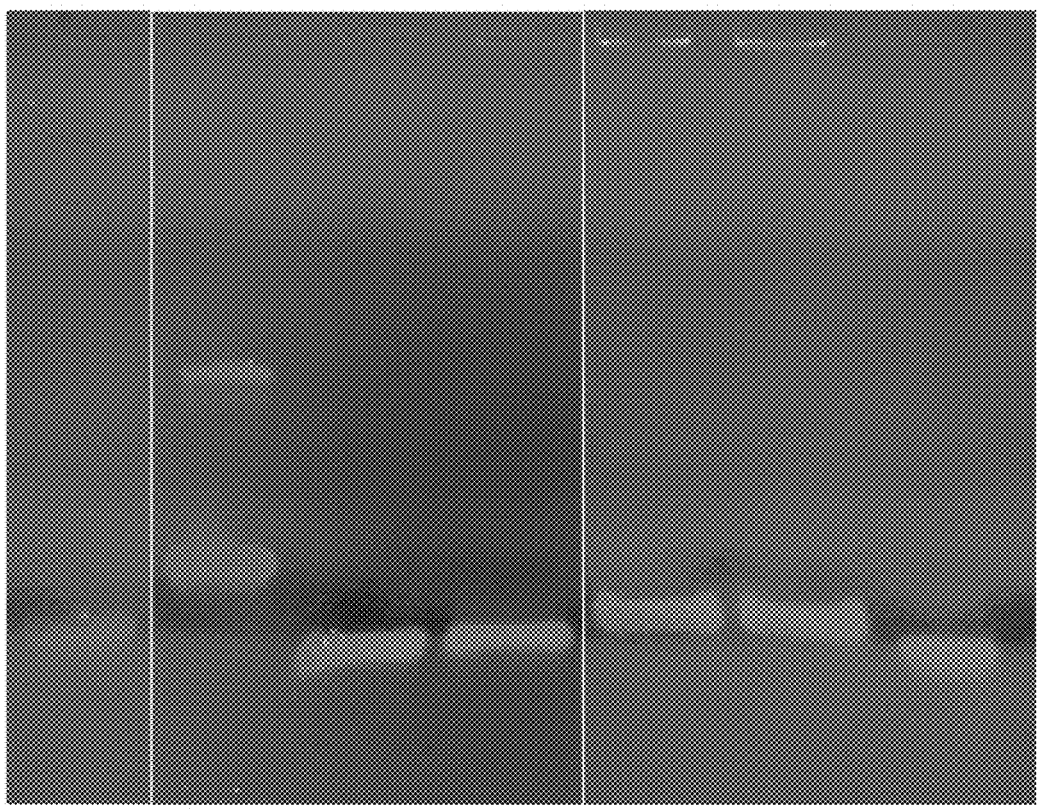

FIG. 16 presents gel electrophoresis, providing evidence for cleavage of a Conjugate of the Invention according to Formula (VIIIb, Apo-Si-W) in vitro, performed by the Dicer enzyme, with removal of one of the MNMs.

DETAILED DESCRIPTION OF THE INVENTION

Embodiments of the present invention relate to novel Conjugates, comprising a delivery system for drugs across biological membranes into the cytoplasm, or through biological barriers, such as, the blood-brain-barrier (BBB), the blood-ocular barrier (BOB), or the blood-fetal-barrier (placental-blood-barrier). Compounds according to embodiments of the invention comprise novel, rationally-designed "Molecular NanoMotors (MNMs)", rationally-designed to move within phospholipid membranes, from the membrane/water interface to the membrane center, utilizing the internal membrane electric field, generated by the membrane dipole potential. When attached to a drug, the delivery system moves the drug towards the membrane center, thus assisting in its trans-membrane movement. Among others, this delivery system is designed for the delivery of therapeutic macromolecules: proteins or oligonucleotides, the latter being single or double-stranded DNA or RNA. Among others, the delivery system is designed for the delivery of antisense oligonuclotides (ASO), siRNA or therapeutic proteins, such as, for example without limitation, the Cas9 protein, or antibodies.

Proposed in a non-limiting manner, one of the major principles underlying the structures of MNMs according to embodiments of the invention is the principle of "asymmetrical polarity". This principle was developed by the Inventors of the present invention, as a tool to enable movement of potentially large and charged molecules within the core of phospholipid membranes, from the membrane surface to the membrane center; movement which is being energized by the intra-membrane electric field, in order to overcome the related energetic barrier. The present invention concerns the translation of this principle of "asymmetrical polarity" into specific molecular structures. These molecular structures were therefore designed to convert the electrostatic potential energy related to the membrane dipole potential, into kinetic energy of molecules, moving within the membrane core. Structurally, these molecules were rationally-designed by the Inventors to be hydrophobic and uncharged, that according to their log P are capable of partitioning into biological membranes. [for example without limitation having a log P value >1 (see FIG. 1A)]. Yet, an important component of the principle of "asymmetrical polarity" is that these molecules are polar, and have their partial charges distributed in an uneven manner: the partial negative charge is highly focused and localized, while the partial positive charge is dispersed along hydrocarbon chains within the molecule. Upon interaction with the phospholipid membrane, these partial positive charges are also masked, through London type hydrophobic interactions, that take place between hydrocarbon chains of the molecule, and adjacent hydrocarbon chains of the phospholipid milieu (London dispersion forces). These features of "asymmetrical polarity", according to which the molecule is hydrophobic but polar, having a the partial negative charge that is focal and discrete, while a respective partial positive charge is dispersed and masked, generates movement of the molecule within the hydrophobic membrane milieu, as shown in FIG. 1A. Since the internal membrane electric field has a negative pole at the membrane/water interface, and a positive pole at the membrane center, the molecules of the invention therefore move towards the membrane center, and when attached to a cargo drug (e.g., a drug, such as, siRNA, ASO, a therapeutic protein or another medicament), the cargo drug is moved to the membrane center. Consequently, this movement may facilitate the trans-membrane movement of the cargo molecule in several ways. Among others, it may enforce adduction of a charged macro-molecule to the phospholipid head-groups (PLHG), perturb the hydration shells around the PLHG, and thus force lateral movement of the PLHG. Formation of transient pores within the membrane may then takes place, with passage of the cargo drug through these pores into the cell. Subsequent spontaneous closure of these transient pores may then take place, thus sealing the membrane pore, with membrane healing (FIG. 2).

The Conjugates of the invention may also comprise performance enhancing moieties (PEM). Such moieties are chemical groups or mechanisms that may act to enhance concentration of the drug, or its related active moiety(ies), at its target sites within cells.

One such pea enhancing approaches (PEM) relates to clearable groups, incorporated within the structure of the Conjugates of the invention ($Q_1$ and $Q_2$ moieties, as defined in Formula (I). The term "cleavable group" in the context of the present invention relates to a chemical moiety, capable of undergoing spontaneous or enzyme-mediated cleavage in certain physiological conditions, such as changes in pH, changes in red-ox state, or other conditions within cells. Examples for cleavable groups are disulfide, dilactone, ester, thio-ester, amide, carbamate, to pH-sensitive moiety, or a redox-sensitive moiety. Cleavage of a Conjugate of the Invention at these sites, may act to trap the cargo drug (e.g., highly negatively-charged siRNA or ASO, or other medicament) in the cytoplasm of the target cell. In addition, the continuous consumption of the Conjugate, due to its cleavage, may also assist in maintaining a concentration gradient of the Conjugate across the plasma or endosomal membranes. Among PEMs based on cleavable groups, which tire within the scope of the present Invention, are, without limitation, disulfides, carbamates, and dilactones.

Another performance enhancing moiety (PEM) within the scope of the Invention, relates to the administration of a Conjugate, where D is a double-stranded RNA, which is a substrate for the Dicer enzyme. Such Conjugates typically comprise a 23-30 dsRNA, selected according to the genetic code and suitable for silencing a specific target gene. The Dicer is a unique nuclease, capable of cleaving double-stranded RNA at specific sites, generating 21-23 double-stranded RNA segments, ready to interact with the RISC complex for gene silencing. According to this approach, one or several MNMs can be linked to such oligonucleotide drug, preferably, at the 3'-end and/or the 5'-end of the sense ("passenger") strand, and/or at the 5'-end of the antisense ("guide") strand. Upon administration of the Conjugate, the MNMs will enable the trans-membrane delivery of the macro-molecule drug. Subsequent cleavage of the dsRNA by the Dicer enzyme in the cytoplasm will then remove the MNM(s) at the 5'-end of the guide stand, thus releasing the siRNA from the delivery system. The siRNA, due to its numerous negative charges, is therefore eventually entrapped in the cytoplasm, where it interacts with the RISC complex, resulting in silencing of the target gene. Dicer-mediated mechanism of intracellular entrapment is schematically illustrated in FIG. 3.

Importantly, the Invention also concerns another innovative performance enhancing approach, based on the concept of "dynamic protonation". This concept is based on installment within the molecular structure, of a basic group (e.g., amine), with a pKa value ranging, between 7.0-8.5. This approach utilizes the fact, that for as basic molecule, interfacial pH is known to be about 1 pH unit lower that in the bulk, and in consideration of the Henderson-Hasselbalch equation, this feature generates two populations of molecules: one that is protonated, and consequently, hydrophilic and soluble in aqueous environments, such as the plasma or cytoplasm; and as second molecular population, of hydrophobic unprotonated molecules, leading to interaction of the molecule with cellular and endosomal membranes. Therefore, the dynamic protonation Principle, as employed for the Conjugates of the Invention, enables the Conjugates of the invention to have "amphibic" characteristics, and provide the ability to move through both hydrophilic and hydrophobic milieus, thus ultimately leading to a large volume of distribution of the Conjugate throughout the body, with entry into the cytoplasm through cell membranes, and escape from the endosomal compartment into the cytoplasm, as desired for an effective system for systemic gene delivery (Example 17, FIG. 15). Respectively, the invention includes an E, E' or E", moiety that comprises a "dynamic protonation moiety, that comprises (i). An amine group, positioned between the negative and positive poles of the MNM; and (ii). Electron-withdrawing groups that flank the amine moiety, acting to set its pKa value at the 7.0-8.5 pH unit range. Examples for such flanking electron-withdrawing groups are carbonyl, ether, ester or fluorocarbon groups.

The term "initiator group" in the context of the present invention, relates to a chemical group, that when it undergoes spontaneous or an enzyme-mediated chemical reaction, it initiates cleavage of an adjacent chemical bond. In more specific embodiments of the invention, the initiator group is selected from $C_4$, $C_5$, $C_6$—1,2-dithiocycloalkyl (1,2-dithiocyclobutane; 1,2-dithiocyclopentane; 1,2-dithiocyclohexane; 1,2-dithiocycloheptane) γ-Lactam, (5 atoms amide ring), δ-Lactam (6 atoms amide ring) or ε-Lactam (7 atoms amide ring); γ-butyrolactone (5 atoms ester ring), δ-valerolactone (6 atoms ester ring) or ε-caprolactone (7 atoms ester ring).

The term "activated ester" in the context of the present invention, relates to a derivative of carboxylic acids, harboring a good leaving group, and thus being capable of interacting with amines to form amides. An example for such activating agent for carboxylic acid is N-hydroxysuccinimide (NHS).

The term "metal chelator" in the context of the present invention, relates to a chemical moiety that entraps a metal ion through coordination, wherein the coordinating atom are selected from nitrogen, sulfur or oxygen atoms. In a preferred embodiment, the chelated ion(s) is calcium ($Ca^{+2}$), coordinated by nitrogen and oxygen atoms of a chelating moiety. In another preferred embodiment, the metal chelator is BAPTA [1,2-bis (o-aminophenoxy) ethane-N,N,N',N'-tetraacetic acid], EGTA (ethylene glycol tetraacetic acid) or analogues thereof, manifesting advantageous selectivity for $Ca^{+2}$ over other ions such as $Me^{+2}$. Such chelators may enable utilization of the substantial concentration gradient of $Ca^{+2}$ between the extracellular space and the cystosol, for potential disengagement of the MNM from the cargo drug, and capture and accumulation of the target drug within the cytoplasm.

The term "heteroalkyl, heteroalkylene or heteroaryl" in the context of the invention, relates to the respective hydrocarbon structure, where a least one of the atoms has been replaced by a nitrogen, oxygen, or sulfur atom(s), or any combination thereof.

According to one of the embodiments of the invention, the "cargo" or the "cargo drug" is a siRNA, ASO, a therapeutic protein, or any other medicament to be delivered across cell membranes and into cells. Said cells may be either in cell culture of within the body of a living animal or a human subject, where said delivery may aim at exerting beneficial therapeutic effects.

The term "precursor" in the context of the invention, relates to a chemical moiety, used in the synthesis of conjugates according to embodiments of the invention. The precursor comprises chemical groups, destined to be removed during the synthesis of the Conjugate, in various stages of the synthesis, for example without limitation, during the attachment of a macromolecule, such as an oligonucleotide to MNMs of the invention.

The field of Protein Drugs for Intracellular Targets (PDIT) is a relatively novel field, derived, in part, from the completion of the Human Genome Sequencing Project, which allows identification of a huge number of novel intracellular targets for potential medical interventions, through administration of protein drugs, gene silencing, RNA or DNA editing, or protein replacement therapy. Conceptually, such therapeutic strategies can be useful for treatment of almost any medical disorder. Specific, highly attractive candidate proteins within the PDIT field are the CRISPR (clustered regularly interspaced short palindromic repeats)-related proteins, and specifically, the Cas9 Protein. Practically, Cas9 can be loaded by any RNA sequence, entailing specificity in directing the protein specifically to any locus within the genome, rationally-selected according to its potential relation to a mutated, defective gene. Cas9 then induces an accurate double-strand cut of the DNA. Naturally-occurring DNA repair mechanisms may then be subsequently recruited, to repair said DNA locus within the malfunctioning gene. Therefore, Cas9 and related proteins enable highly effective gene editing (adding, disrupting or changing the sequence of specific genes) and gene regulation and repair, applicable to species throughout the tree of life. By delivering Cas9 protein and an appropriate guide RNA into a cell, the organism's genome can therefore be cut at any desired location, and be subjected to editing and repair.

As exemplified below (Example 4), an embodiment of the invention includes one or more "molecule nanometers (MNMs)" linked to the Cas9 protein, having a potential role in DNA or RNA editing. Another embodiment of the invention relates to a therapeutic protein, administered as replacement therapy. Such replacement therapy may be needed in the treatment of a disease, associated with reduced levels of a physiologically-important protein, due to its deficiency or mutations. In such case, the respective protein may be delivered exogenously as a drug. Since protein is a charged macro-molecule, many times it is incapable of trans-membrane delivery, unless conjugated to a delivery system, such as the MNMs of the invention.

MNMs according to embodiments of the invention are typically hydrophobic [for example, without limitation, having an octanol to water partition co-efficient (log P)>1], dipolar, uncharged chemical moieties, designed according to the principle of asymmetrical polarity (explained above). As discussed, this unique set of features of the MNM (namely, being, hydrophobic, of overall neutral charge, but being polar, with focused partial negative charges and dispersed partial positive charges, creates a unique vectorial system when put in the internal membrane electric field, entailing movement of the molecule within the phospholipid milieu from the membrane/water interface to the membrane center. When attached to a drug, this molecule respectively pulls the drug to the membrane core.

As schematically illustrated in FIG. 1B, Conjugates according to embodiments of the invention typically include "Molecular NanoMotor(s) (MNMs)" as described above, being an E, E' or E" moiety [demonstrated, for example, by a moiety according to any of Formulae (VII-XIa)]. The "Molecular NanoMotor (MNM)" is a combination of the following structural motifs:

(i) A negative pole (group A of moiety E, E', or E"), typically comprising at least one electronegative atom(s), selected from a halogen [for example, fluorine atom(s)] or oxygen, that ma be arranged in space as a focused, spherical (or near spherical) arrangement. Due to the electron-withdrawing properties of such atoms, and their structural arrangement in space, the negative pole of the Conjugate is an electron-rich focus. In a preferred embodiment, A is a residue of nona-fluoro-tertbutanol.

(ii) A positive pole (group B of moiety E, E' or E"), comprising relatively electropositive atoms, selected from carbon, silicon, boron, phosphor and sulfur, arranged to enable maximal interaction with adjacent hydrocarbon chains, when put in a phospholipid membrane, preferably through arrangement as an aliphatic or aromatic structure of linear, branched or cyclic chains, or combinations thereof. In an embodiment of the invention, the positive pole comprises linear, saturated hydrocarbon chain(s), or a steroid moiety, such as cholesterol, bile acids, estradiol, estriol, or derivatives or combinations thereof. Optionally, the Conjugate of the invention may comprise several negative pole and/or several positive pole structural motifs, for example, sequentially-arranged perfluro- and oxygen-motifs, separated by hydrocarbon chains, exemplified by any of Formulae (VII-XId).

In addition to the "Molecular NanoMotor(s) (MNMs)" and the drug D, a Conjugate according, to embodiments of the invention may also comprise one or more linker(s) (L) and cleavable group(s) (Q), as further described in the specific Formulae of the invention. The linkage of a drug D to the Molecular NanoMotor(s) E, E' or E" can be either directly, or through moiety L or Q; said linkage can be either through covalent or non-covalent bonds, such as electrostatic or coordinative bonds.

In addition to the above, an MNM of the invention may be used as part of a pharmaceutical composition, in addition to an active drug. Due to the enhancement of membrane interactions provided by the MNM, performance of the active drug may be improved by the inclusion of the MNM, in aspects such as efficacy or safety.

Embodiments of the invention further relate to the use of Conjugates according, to the invention, comprising therapeutically-useful drugs, such as, proteins or oligonucleotides (e.g., siRNA or ASO), for the treatment of medical disorders in a subject in need thereof. The medical disorders may be, without being limited, degenerative disorders, cancer, traumatic, toxic or ischemic insults, infections or immune-mediated disorders, in which specific protein(s) play(s) a role in either disease etiology or pathogenesis, and where modulation of the expression of the respective gene(s), through siRNA or antisense mechanisms, or modulation of the activity of the respective protein by a therapeutic protein or by protein replacement therapy, may have beneficial effects in inhibiting disease-related processes or treating the underlying disease.

For example, Conjugates according to embodiments of the invention may be used as antisense therapy, which is a form of medical treatment comprising the administration of a single-stranded or a double-stranded nucleic acid strands (DNA, RNA or a chemical analogue), that binds to a DNA sequence encoding for a specific protein, or to the respective messenger RNA (mRNA), where the translation into protein takes place. This treatment may act to inhibit the expression of the respective gene, thereby preventing the production of the respective protein. Alternatively, the Conjugates of the invention may comprise therapeutic proteins, such as the Cas9 protein.

The terms "drug" or "medicament" in the context of the present invention relate to a chemical substance, that when administered to a patient suffering from a disease, is capable of exerting beneficial effects on the patient. The beneficial effects can be amelioration of symptoms, or counteracting, the effect of an agent or a substance, that play(s) a role in the disease process. The drug may comprise a small molecule or a macromolecule, such as, a protein, or single- or double-stranded RNA or DNA, administered to inhibit gene expression. Among others, the drug may comprise siRNA or ASO. In some embodiments, the drug is aimed at treating degenerative disorders, cancer, ischemic, infectious, toxic insults, or immune-mediated disorders.

The term "biological membrane" according to the invention refers to any phospholipid membrane related to as biological system. Examples for such phospholipid membranes are the plasma membrane of cells, intercellular membranes, or biological barriers, such as the blood-brain-bather (BBB), the ocular-blood-barrier (BOB), or the blood-placenta barrier.

Embodiments of the invention provide Conjugates, comprising MNMs according to embodiments of the invention, and a drug. Embodiments of the invention further provide pharmaceutical compositions, comprising the Conjugates described herein, and pharmaceutically-acceptable carrier(s) or salt(s).

Other embodiments of the invention, describe methods for treatment of medical disorders, comprising administration to a patient in need a therapeutically effective amounts of a pharmaceutical composition comprising Conjugates of the invention. In some embodiments, the medical disorder is cancer. In some specific embodiments, the cancer is, among others melanoma or uterine cervical cancer.

According to some embodiments, the Conjugates and pharmaceutical compositions of the invention may be used to achieve efficient delivery and effective performance of a replacement protein therapy or gene therapy, [for example, without limitation siRNA or antisense therapy (ASO), in vivo, in the clinical setting.

A Conjugate according to embodiments of the invention may be advantageous in improving delivery of siRNA, ASO or a therapeutic protein through cell membranes or through biological barriers, such as the Blood-Brain-Barrier (BBB), thus improving the performance of the macromolecule drug in one or more aspects, such as, for example, efficacy, toxicity, or pharmacokinetics.

In an embodiment of the invention, it provides that the drug is a macromolecule, selected from the group consisting, of siRNA, ASO and a therapeutic protein.

In an embodiment of the invention, it provides a Conjugate of the invention and a pharmaceutically-acceptable salt or carrier.

In an embodiment of the invention, it provides a method for delivery drug into biological cells, wherein said cells a are in culture, or living animal or a human subject; the method comprising contacting the cells with a Conjugate of the invention.

In an embodiment of the invention, it provides a method wherein the biological membrane is selected from a group consisting of cell membranes and biological barriers, wherein said biological barrier are selected from the blood-brain-barrier, blood-ocular-barrier or the blood-fetal-barrier.

As described above in a non-limiting potential Mechanism Of Action (MOA), Conjugates according to embodiments of the invention, comprising a drug such as siRNA or a therapeutic protein, conjugated MNM(s), undergo transmembrane delivery when interacting with a phospholipid membrane. This mechanism of action is schematically summarized in FIG. 2. Due to the principle of asymmetrical polarity, initially, the MNM(s) move(s) from the membrane surface membrane core, energized by the internal membrane electric field FIG. 2A. As the second stage, FIG. 2B, the macromolecule, linked to the MNMs, is forced to approach the membrane surface, thus perturbing the hydration shells of both the cargo macromolecule drug and the phospholipid head-groups. Consequently, there is lateral movement of the phospholipid head-groups and formation of transient membrane pores, through which the macromolecule drug is delivered into the cell. Subsequent closure of the transient pore then takes place with membrane healing. FIG. 2C, being energetically favored.

Conjugates according to embodiments of the invention have the structure, as set forth in general Formula (I):

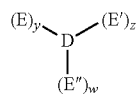

Formula (I)

including pharmaceutically acceptable salts, hydrates, solvates and metal chelates of the compound represented by the structure as set forth in Formula (I), and solvates and hydrates of the salts; wherein, D is a drug to be delivered across biological membranes. D may be a small-molecule drug, a peptide, a protein, or a native or modified, single-stranded, or double-stranded DNA or RNA, such as siRNA or ASO; y, z and w are each an integer, independently selected from 0, 2, 3, 4, 5, 6, wherein whenever the integer a is 0, it means that the respective E moiety is null; at least one of y, z or w is different from 0. In one embodiment, y=1, z=o and w=0; in another embodiment y=1, z=1 and w=0.

E, E', or E" can be the same or different, each having the structure as set fourth in general Formula (II):

$$(A)_a\text{-B-L}_1\text{-Q}_1\text{-L}_2\text{-Q}_2\text{-L}_3$$ Formula (II)

wherein each A moiety is independently selected from the structures as set forth in Formulae (III), (IV), (V) and (VI):

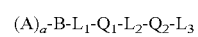

Formula (III)

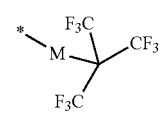

Formula (IV)

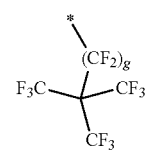

Formula (V)

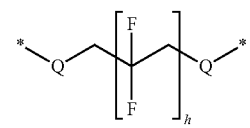

Formula (VI)

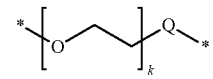

M is selected from —O— or —CH$_2$—; and g, h and k are each individually an integer selected from the group consisting of 0, 1, 2, 3, 4, 5, 6, 7, 8, 9, 10, 11, 12, 13, 14, 15 and 16; * is —H, or a point of linkage to B, or to another A group; a is an integer, selected from 1, 2, 3 or 4; Q is oxygen or amine.

B (a positive pole as described above) is selected from one or more of the groups, consisting of:

linear, cyclic or branched $C_1$, $C_2$, $C_3$, $C_4$, $C_5$, $C_6$, $C_7$, $C_8$, $C_9$, $C_{10}$, $C_{11}$, $C_{12}$, $C_{13}$ or $C_{14}$, alkyl or hetero-alkyl, wherein each is optionally substituted by one or more halogen, hydroxyl, methoxy, fluorocarbon, amine or thiol; or optionally linked to an ether, an ester, or an amide group;

linear, cyclic or branched $C_2$, $C_3$, $C_4$, $C_5$, $C_6$, $C_7$, $C_8$, $C_9$, $C_{10}$, $C_{11}$, $C_{12}$, $C_{13}$ or $C_{14}$ alkylene or heteroalkylene, wherein each is optionally substituted by one or more halogen, hydroxyl, methoxy, fluorocarbon, amine or thiol; or optionally linked to an ether, an ester, or an amide group;

$C_5$, $C_6$, $C_7$, $C_8$, $C_9$, $C_{10}$, $C_{11}$, $C_{12}$, $C_{13}$ or $C_{14}$ aryl or heteroaryl, wherein each is optionally substituted by one or more halogen, hydroxyl, methoxy, fluorocarbon, amine or thiol; or optionally linked to an ether, an ester, or an amide group;

one or more steroid moiety (such as cholesterol, bile acid, estrogen, estradiol, estriol, lithocholic acid or any analog thereof), nucleoside, nucleotide; and any combination thereof, wherein each is optionally substituted by one or more halogen, hydroxyl, methoxy, fluorocarbon, amine or thiol; or each is optionally linked to an ether, an ester, an amine, or an amide group; or any combination thereof;

$Q_1$ and $Q_2$ are each a cleavable group, independently selected from null, ester, thio-ester, amide [e.g., —C(=O)—NH— or —NH—C(=O)—], carbamate [e.g., —O—C(=O)—NH— or —NH—C(=O)—O—], urea [—NH—C(=O)—NH—], disulfide [—(S—S)—], ether [—O—], amine, imidazole, triazole, dilactone, a pH-sensitive moiety, a redox-sensitive moiety; a metal chelator, including its chelated metal ion; and any combinations thereof;

$L_1$, $L_2$ and $L_3$ are each independently selected from null and the group consisting of linear, cyclic or branched $C_1$, $C_2$, $C_3$, $C_4$, $C_5$, $C_6$, $C_7$, $C_8$, $C_9$, $C_{10}$, $C_{11}$, $C_{12}$, $C_{13}$, or $C_{14}$, alkyl or hetero-alkyl, wherein each is optionally substituted by one or more halogen, hydroxyl, methoxy, fluorocarbon, amine, or thiol; or linked to an ether group;

linear, cyclic or branched $C_2$, $C_3$, $C_4$, $C_5$, $C_6$, $C_7$, $C_8$, $C_9$, $C_{10}$, $C_{11}$, $C_{12}$, $C_{13}$ or $C_{14}$ alkylene or heteroalkylene, wherein each is optionally substituted by one or more halogen, hydroxyl, methoxy, fluorocarbon, amine, thiol, or linked to an ether group;

$C_5$, $C_6$, $C_7$, $C_8$, $C_9$, $C_{10}$, $C_{11}$, $C_{12}$, $C_{13}$ or $C_{14}$ aryl or heteroaryl, wherein each is optionally substituted by one or more halogen, hydroxyl, methoxy, fluorocarbon, amine, thiol; or linked to an ether group;

—(O—CH$_2$—CH$_2$)$_u$—, wherein each is optionally substituted by one or more halogen, hydroxyl, methoxy, fluorocarbon, amine, or thiol;

nucleoside, nucleotide; imidazole, azide, acetylene; and any combinations thereof, wherein each is optionally substituted by one or more halogen, hydroxyl, methoxy, fluorocarbon, amine, thiol; or linked to an ether group; and wherein u is an integer of 1, 2, 3, 4 or 5; and any combinations thereof;

wherein at least one of $Q_1$, $Q_2$, $L_1$, $L_2$ and $L_3$ is not null; and wherein each of $Q_1$, $Q_2$, $L_1$, $L_2$ and $L_3$ is optionally comprises a T moiety; wherein T is an initiator group, selected from $C_4$, $C_5$, $C_6$—1,2-dithiocycloalkyl (1,2-dithiocyclo-butane; 1,2-dithiocyclo-pentane, 1,2-dithiocyclohexane; 1,2-dithiocycloheptane); γ-Lactam (5 atoms amide ring), δ-Lactam (6 atoms amide ring) or ε-Lactam (7 atoms amide ring); γ-butyrolactone (5 atoms ester ring), δ-valerolactone (6 atoms ester ring) or ε-caprolactone (7 atoms ester ring); wherein each is optionally substituted by one or more halogen, hydroxyl, methoxy, fluorocarbon, amine, or thiol; or is linked to an ether group;

wherein at least one of B, $Q_1$, $Q_2$, $L_1$, $L_2$ and $L_3$ is conjugated to a drug (D), as defined in Formula (I).

In an embodiment of the invention, it provides that at least two of $Q_1$, $Q_2$, $L_1$, $L_2$ and $L_3$ are not null;

In an embodiment of the invention, it provides that at least two of $Q_1$, $Q_2$, $L_1$, $L_2$ and $L_3$ are not null;

The linkage of D to other moieties of the molecule can be through covalent, electrostatic, or coordinative bonds. In the case that the bond is covalent, linkage can be through a $Q_1$ or $Q_2$ moiety, each being selected from the group consisting of ether, ester, amide, thioester, thioether and carbamate groups. In the case that the bond is coordinative, it involves a $Q_1$ or $Q_2$ group that is a metal chelator, and the linkage preferably involves coordination of calcium ion(s). An example for electrostatic linkage can be a salt bridge between amine groups of moiety $L_1$, $L_2$ or $L_3$ of E, E' or E", and negatively-charged phosphate groups of D. In case that D is an oligonucleotide, linkage can be to the nucleobase, to the ribose moiety (e.g., through the 2', 3' or 5' positions of the ribose), or to the phosphate moiety of the nucleotide; linkage can be either to a terminal, or to a non terminal nucleotide of the oligonucleotide chain; linkage can be through a natural or through a modified nucleotide. In the case that D is as protein, its linkage to the other moieties of the molecule can be through linkage to side chain(s) of the protein's amino acids, such as lysine, cysteine, glutamate or aspartate.

The term "oligonucleotide", in the context of the invention, may include DNA or RNA molecules, each being a single-stranded or double-stranded sequence of one or more nucleotides. Each nucleotide comprises a nitrogenous base (nucleobase), a five-carbon sugar (ribose or deoxyribose), and a phosphate group. The nucleobases are selected from purities (adenine, guanine) and pyrimidines (thymine, cytosine, uracil). In addition, the term may also refer to modified forms of nucleotides, where the modification may be at the backbone of the molecule (e.g., phosphorothioate, peptide nucleic acid) or at the nucleobase (e.g., methylation at the 2' position of the ribose group in RNA, or attachment of fluorine atoms at that site). These modifications may enable properties such as improved stability or improved pharmacokinetics of the oligonucleotide in body fluids. The use of such modified oligonucleotides is therefore also within the scope of the invention.

In one embodiment a method for specific inhibition of gene expression is disclosed, applicable either in vitro or in vivo. The method comprises the utilization of a Conjugate of the invention, or a pharmaceutical composition comprising the Conjugate, where D is siRNA or ASO, designed to silence the expression of a specific gene, which encodes for a pathogenic protein, that has a role in the etiology or pathogenesis of disease.

Accordingly, Conjugates according to embodiments of the invention may be used for the treatment of a medical disorder. Embodiments of the invention therefore disclose a method for medical treatment, comprising the administration to a patient in need, therapeutically effective amounts of as pharmaceutical composition according to embodiments of the invention. In one embodiment, the administered pharmaceutical composition may comprise siRNA or an antisense oligonucleotide, active in inhibiting the expression of a specific gene encoding for a disease-related protein.

In one embodiment of the invention, there are provided Conjugates according to general Formula (I), wherein E, E' or E" moiety has the structure as set forth in general Formula (VII), and related structures:

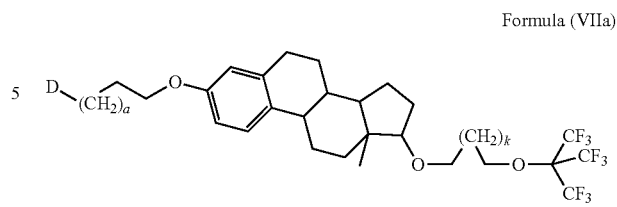

Formula (VIIa)

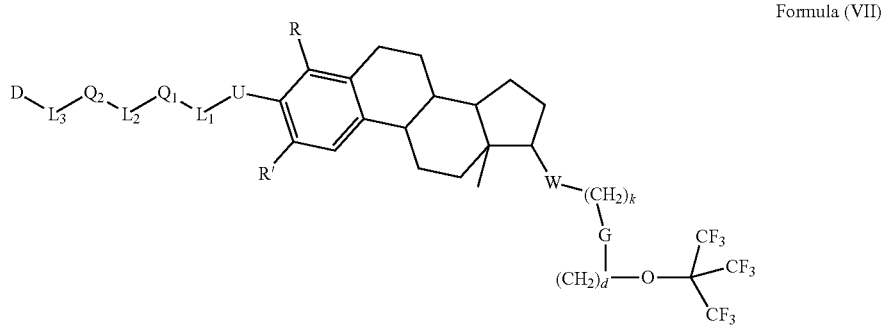

Formula (VII)

U is selected from the group consisting of null, —O—, ester, amide, and amine (secondary or tertiary amine); $L_1$, $L_2$, $L_3$, $Q_1$, $Q_2$ have the same meaning as described for Formula (I), R and R' are each independently selected from the group consisting of hydrogen, halogen, hydroxyl group, a methoxy group, and a fluorocarbon group; W and G are each independently selected from null, oxygen, ester, amide or amine (secondary or tertiary amine) groups; k and d, each stands independently for an integer, selected from null, 0, 1, 2, 3, 4, 5 or 6; and the E, E' or E" moiety is conjugated to D, wherein D is a drug, as defined in Formula (I); including pharmaceutically acceptable salts, hydrates, solvates and metal chelates of the Compound represented b the structure as set forth in Formula (VII), or the related analogues, and solvates and hydrates of the salts.

In an embodiment of the Invention, R or R' is each independently selected from hydrogen and a fluorine atom.

In an embodiment of the Invention, the estradiol moiety is substituted by another steroid residue. Said steroid residue can be cholesterol, lithocholic acid, or as related analogue.

In an embodiment of the Invention, $L_1$, $L_2$ and $L_3$ are each individually selected from null and as linear, cyclic or branched $C_1$, $C_2$, $C_3$, $C_4$, $C_5$, $C_6$, $C_7$, $C_8$ hydrocarbon chain, optionally linked to an ether or amine group; $L_1$, $L_2$ and $L_3$ can be the same or different.

In an embodiment of the Invention, $Q_1$ or $Q_2$ is a moiety selected from amide, ester, ether, carbamate or disulfide.

In another embodiment of the Invention, $L_1$, $L_2$ or $L_3$ comprises a T moiety, wherein T is 1,2-dithiocyclo-butane, optionally substituted by halogen, hydroxyl, methoxy, fluorocarbon, amine, or thiol.

In a more specific embodiment, the Invention provides a Conjugate according to general Formula (I) or Formula (VII), wherein E, E' or E" has the structure as set forth in Formula (VIIa):

Wherein a and k each stands independently for an integer of 0, 1, 2, 3, 4, 5 or 6; including pharmaceutically acceptable salts, hydrates, solvates and metal chelates of the Compound represented by the structure as set forth in Formula (VIIa), or the related analogues, and solvates and hydrates of the salts.

In other embodiments, the Invention provides the following Conjugates:

Class A: Conjugates According to Formulae (I), (VII), Wherein E, E' or E" Comprise(s) "Dynamic Protonation Moieties":

The Invention provides Conjugates according to general Formula (I) or Formula (VII), comprising MNM(s), wherein E, E' or E" moiety may comprise a "dynamic protonation moiety" as described above, that consists of (i). An amine group, positioned between the negative and positive poles of the MNM; and (ii). Electron-withdrawing groups that flank the amine moiety, setting the amine pKa value at the 7.0-8.5 pH unit range. Examples for such flanking electron-withdrawing groups are carbonyl, ether, ester or fluorocarbon moieties/groups. Each of these E, E' or E" moieties, may independently have the structure as set forth in Formulae (VIIIa), (VIIIb), (VIIIc), (VIIId), (VIIIe), (VIIIf), (VIIIg), (VIIIh), or (IXd), (IXe), (IXf), (IXg), (IXh), including related pharmaceutically-acceptable salts, hydrates, solvates and metal chelates, and solvates and hydrates of the salts; wherein D is a drug, as defined in Formula (I); $L_3$ has the same meaning as in Formula (I); a, k, d when applicable, each stands independently for integer of 0, 1, 2, 3, 4, 5 or 6; and R''' is selected from the group consisting of hydrogen, methyl and ethyl:

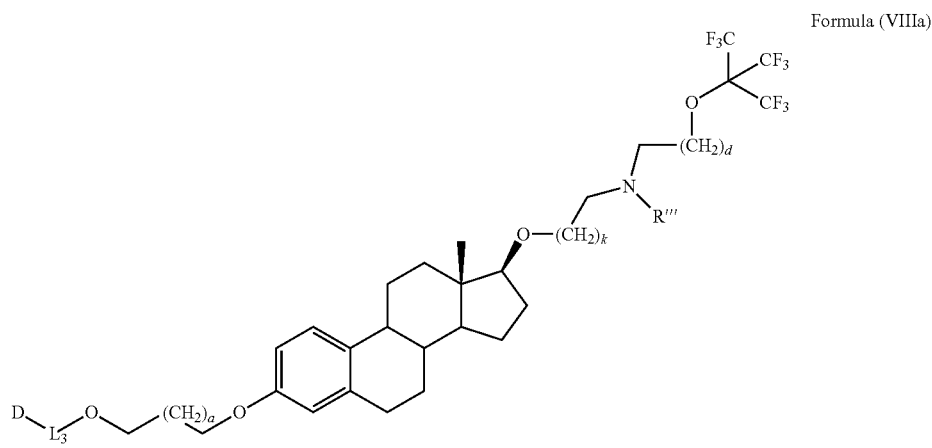
Formula (VIIIa)
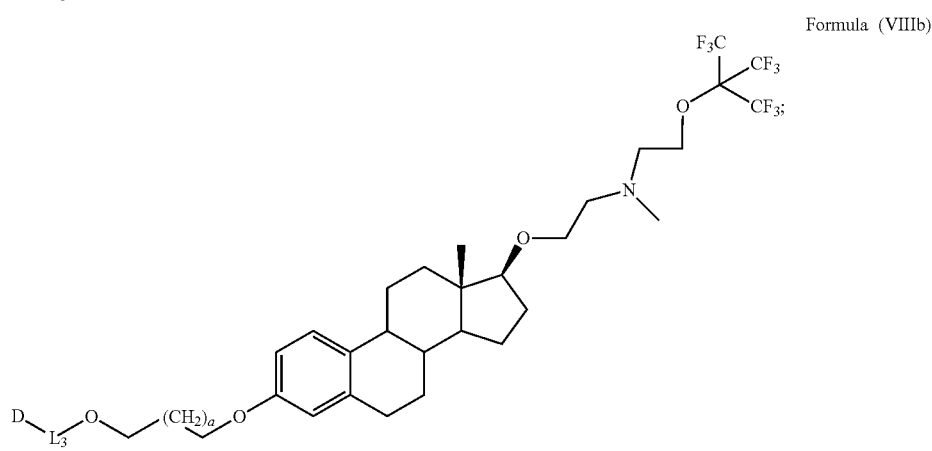
Formula (VIIIb)
when a = 2 and L₃ = null; designated Apo-Si-W
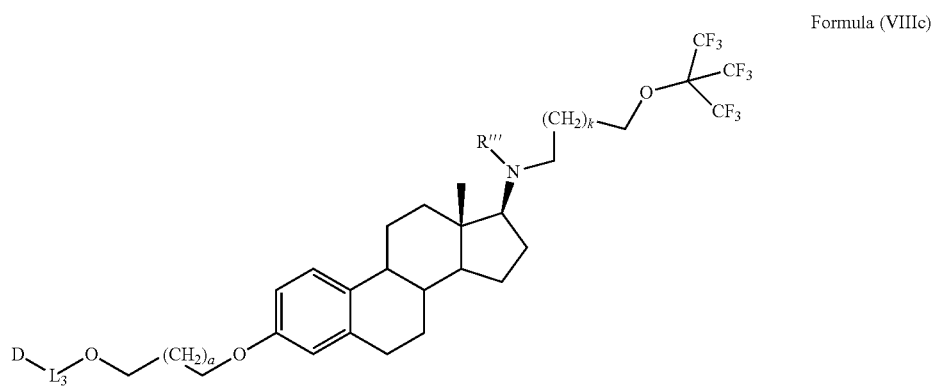
Formula (VIIIc)
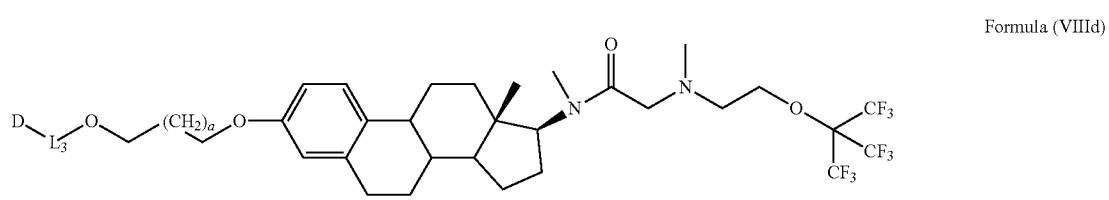
Formula (VIIId)
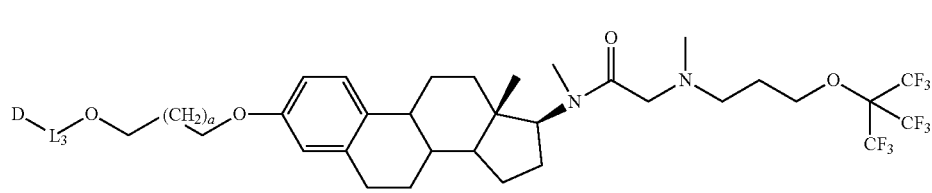
Formula (VIIIe)

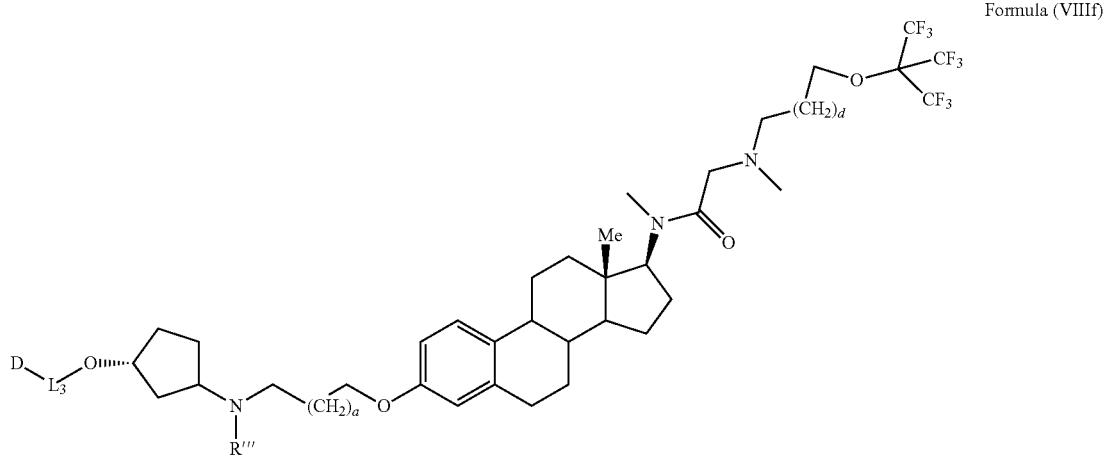

Formula (VIIIf)

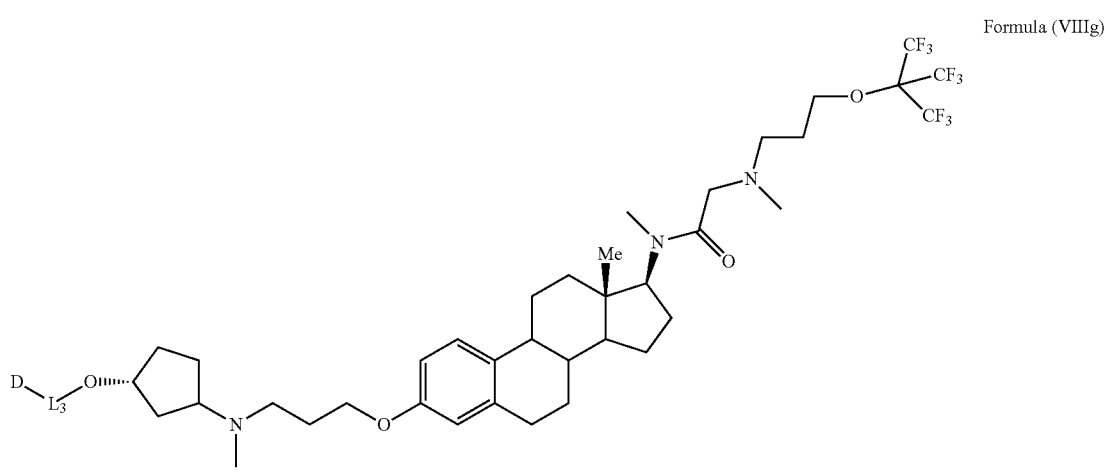

Formula (VIIIg)

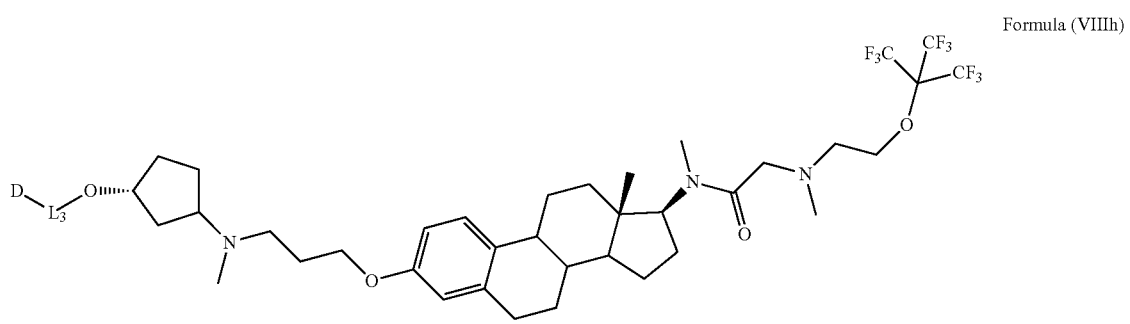

Formula (VIIIh)

Class B: Conjugates According to Formulae (I), (VII), Wherein E, E' or E" Comprise a Cleavable Disulfide Moiety:

The invention also provides a Conjugate according to general Formula (I) or Formula (VII) wherein E, E' or E" may comprise a cleavable group, being a disulfide moiety. These E, E' or E" moieties may each haw the structure as set forth in Formula (IX), and related structures according to Formula (IXa), Formula (IXb), Formula (IXc), Formula (IXd), Formula (Xe), Formula (IXf), Formula (IXg), and Formula (IXh):

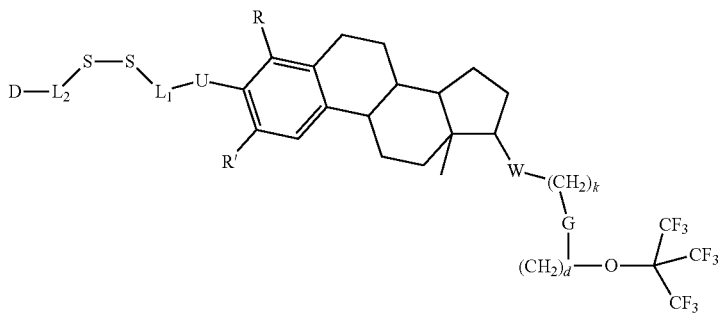

Formula (IX)

Wherein U is selected from the group consisting of null, —O—, ester, amide, and amine (secondary or tertiary amine); $L_1$, $L_2$ and $L_3$ have the same meaning as above; R and R' are each independently selected from the group consisting of hydrogen, halogen, hydroxyl group, a methoxy group, and a fluorocarbon group; W and G are each independently selected from null, oxygen, ester, amide or amine (secondary or tertiary amine) groups; a, h, k and d, each stands independently for an integer, selected from null, 0, 1, 2, 3, 4, 5 or 6; and the E, E' or E" moiety is conjugated to D, wherein D is a drug, as defined in Formula (I); including, pharmaceutically acceptable salts, hydrates, solvates and metal chelates of the Compound represented by the structure as set forth in Formulae (IX), or the related analogues, having the structure as set forth in Formula (IXa), Formula (IXb), Formula (IXc), Formula (IXd), Formula (Xe), Formula (IXf), Formula (IXg) and Formula (IXh), and solvates and hydrates of the salts:

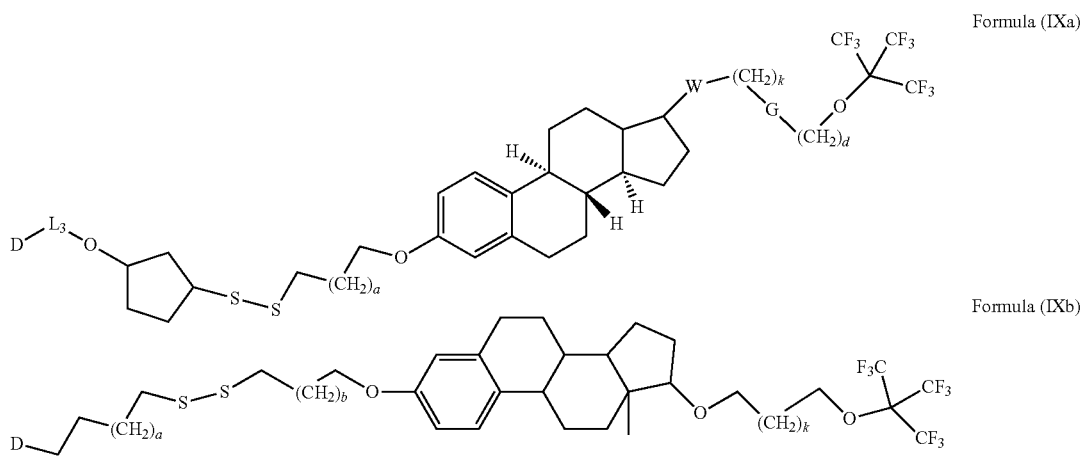

Formula (IXa)

Formula (IXb)

In the case that a = 3, b= 0 and k = 1, the moiety is designated Apo-Si—S—S

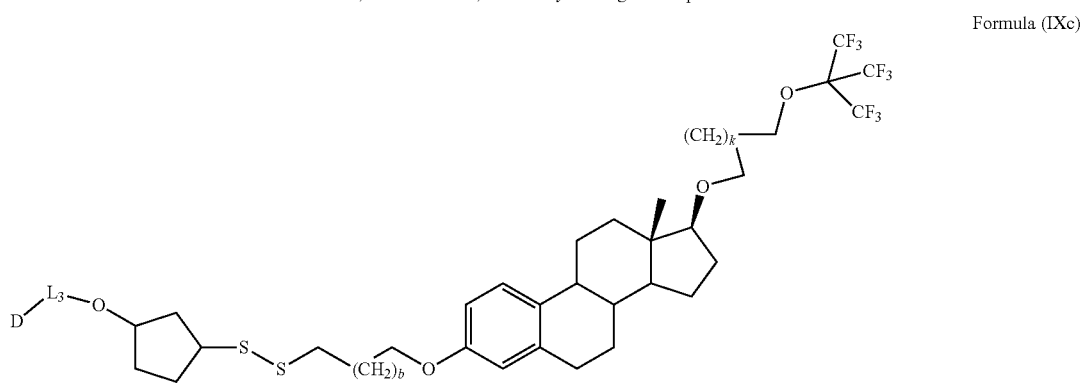

Formula (IXc)

in the case that a = 1, k = 1; the moiety is designated Apo-Si—G

Class C: Structures According to Formulae (I), (VII), (IX), that Comprise Both a Cleavable Disulfide Moiety, and a Dynamic Protonation Moiety:

Wherein $L_3$ has the same meaning as above; b, d, each stands independently for an integer, selected from null, 0, 1, 2, 3, 4, 5 or 6; and R'" selected from the group consisting of hydrogen, methyl and ethyl; and the E, E' or E" moiety is conjugated to D, wherein D is a drug, as defined in Formula (I);

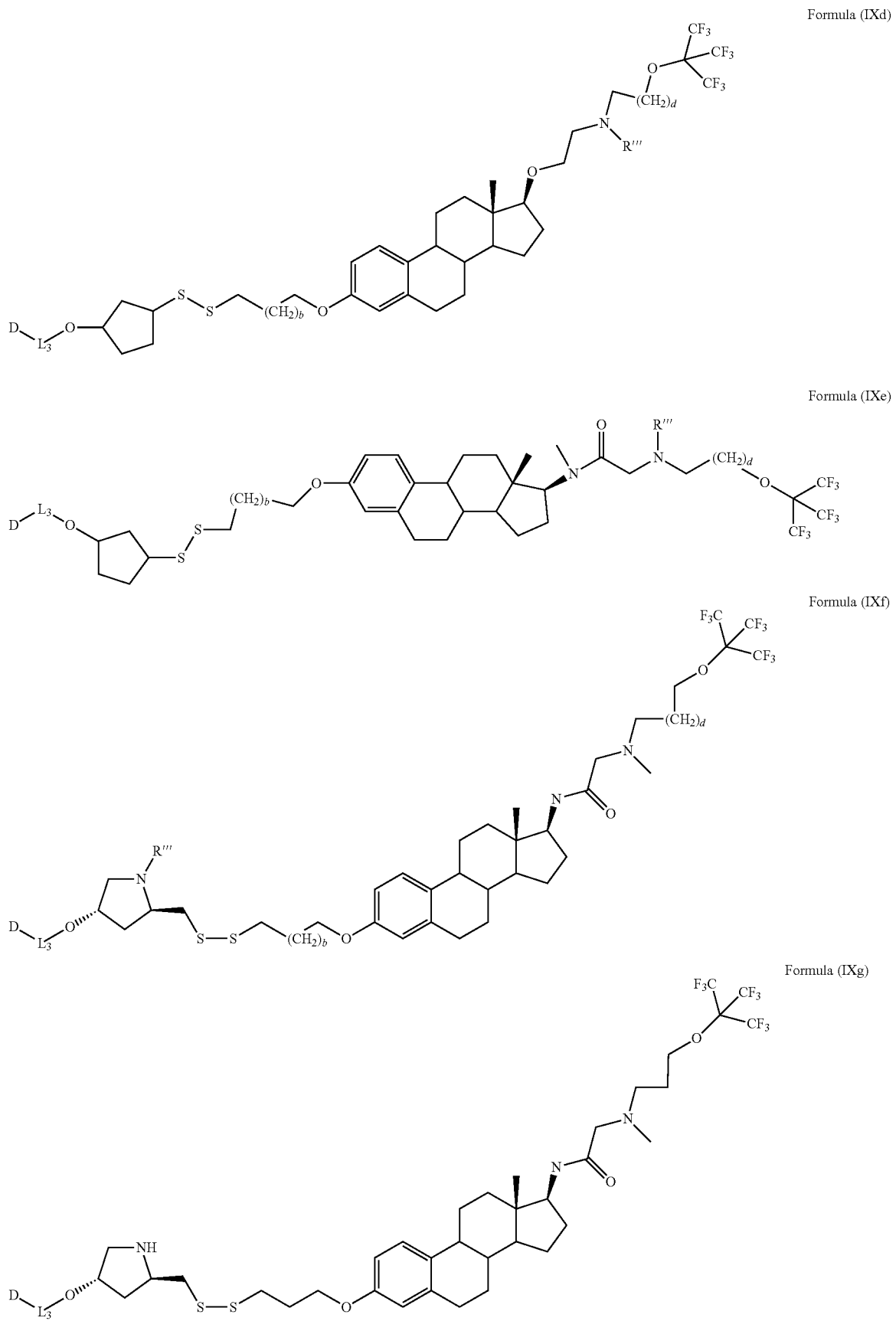

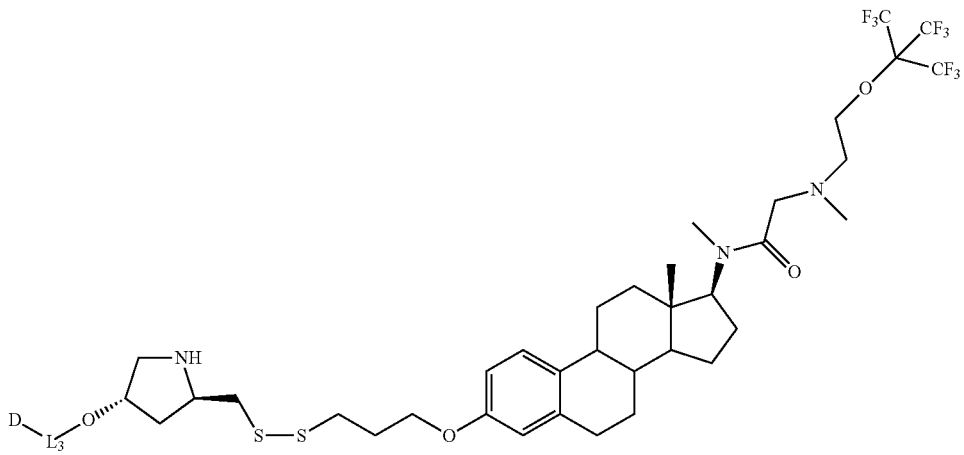

Formula (IXh)

Class D: Conjugates According to Formulae (I), (VII), (X), Wherein E, E' or E" Comprises a Cyclic Disulfide Moiety and a Carbamate Moiety:

The invention also provides Conjugates according to General Formula (X), wherein E, E' or E" may comprises a carbamate group, and the cleavable disulfide moiety is within a cyclic structure, according to Formulae (X), (Xa), (Xb) or (Xc); and related structures, wherein the disulfide can be either in its oxidized or reduced (open-ring) forms:

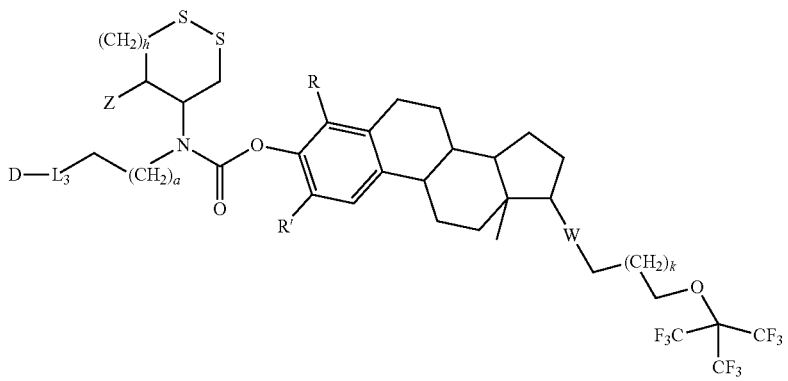

Formula (X)

wherein a, d, k, d each stands independently for an integer, selected from the group consisting of 0, 1, 2, 3, 4, 5, 6; h is an inter of 1, 2, 3, or 4; Z is selected from hydrogen, fluorine, hydroxyl and amine groups; R and R' are each independently selected from the group consisting of hydrogen, halogen, hydroxyl group, a methoxy group, and a fluorocarbon group; $L_3$ has the same meaning as in Formula (I); G is selected from the group consisting of hydrogen, halogen, hydroxyl group, a methoxy group, and a fluorocarbon group; W is selected from oxygen, amide, ester and amine (secondary or tertiary amine); D is a drug, as defined in Formula (I), including pharmaceutically acceptable salts, hydrates, solvates and metal chelates of the Compound represented by the structure as set forth in Formulae (X), or the related analogues, having the structure as set fourth in Formula (IXa), Formula (IXb), Formula (Xa), Formula (Xb), Formula (Xc), and solvates and hydrates of the salts;

In an embodiment of the Invention, k=1, and h=1. In an embodiment of the Invention, at least on R of R' is a fluorine atom, the other being a hydrogen atom.

Structures of the invention, comprising, a cyclic disulfide moiety, and which are thus related to Formula (X) are:

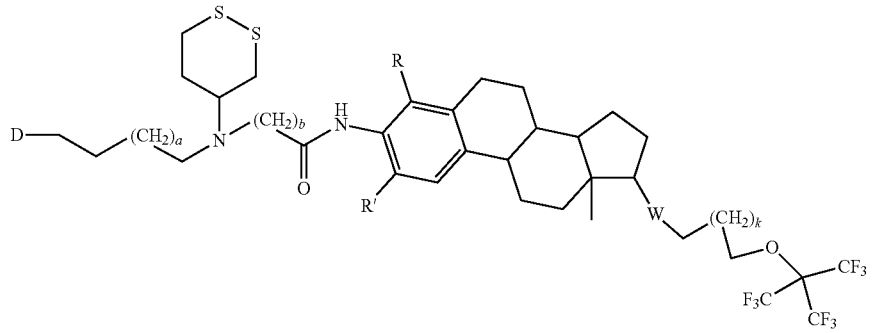

Formula (Xa)

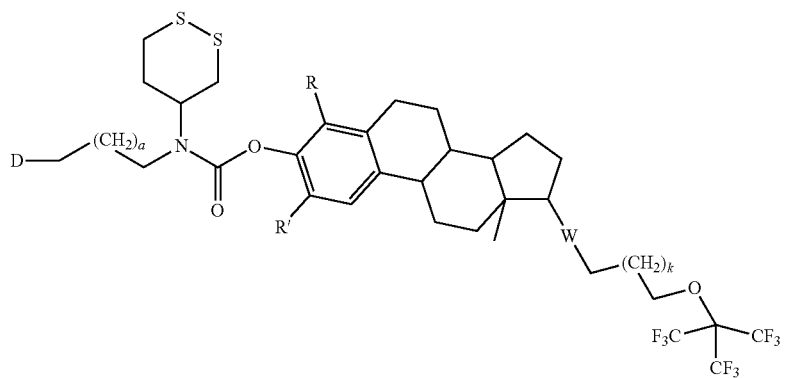

Formula (Xb)

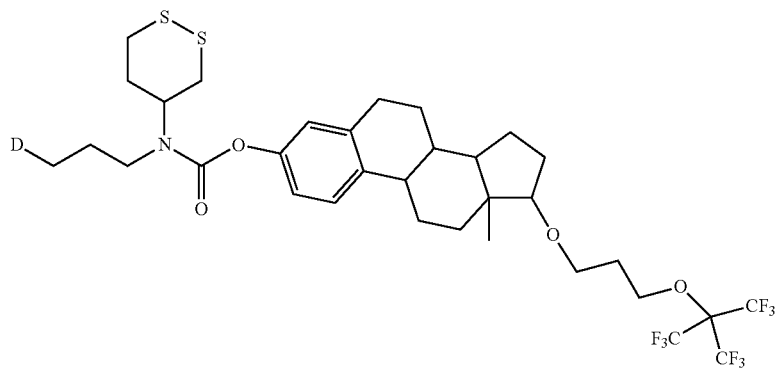

Formula (Xc)

including pharmaceutically acceptable salts, hydrates, solvates and metal chelates of the Compound represented by the structure as set forth in Formulae (X), or the related analogues, having the structure as set forth in Formula (Xa), Formula (Xb), Formula (Xc), and solvates and hydrates of the salts.

Class E: Conjugates According to Formulae (I), (VII), (XI), Wherein E, E' or F" Comprises Both a Cleavable Carbamate Moiety, and a Dynamic Protonation Moiety:

Formula (XI)

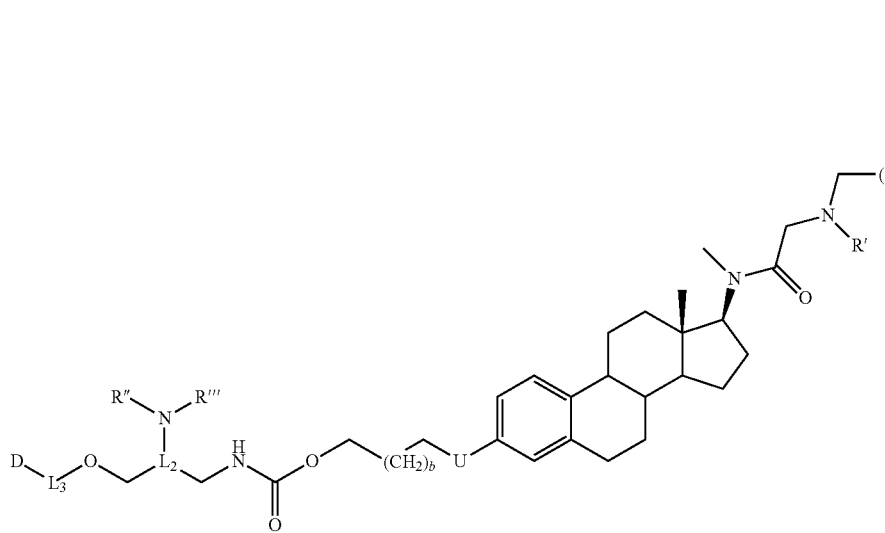

Wherein L₃ or L₂, each has the meaning according to Formula (I), U is selected from the group consisting of null, —O—, ester, amide, and amine (secondary or tertiary amine), b and d each stands for an integer of 0, 1, 2, 3, 4, 5 or 6; R', R" and R'" each strands independently for hydrogen, methyl or ethyl; D is a drug as defined in Formula (I), including pharmaceutically acceptable salts, hydrates, solvates and metal chelates of the Compound represented by the structure as set forth in Formulae (XI), or the related analogues, having the structure as set forth in Formula (IXa), Formula (IXb), Formula (IXc) or Formula (IXd), and solvates and hydrates of the salts:

Formula (XIa)

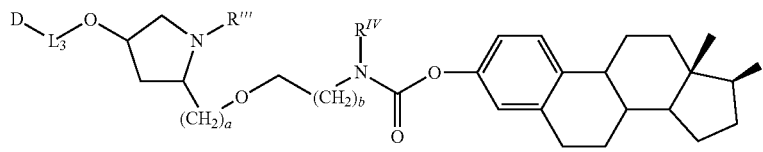

Wherein L₃ has the meaning according to Formula (I), a, b and d each stands for an integer of 0, 1, 2, 3, 4, 5 or 6; R", R'", R^IV each strands independently for hydrogen, methyl or ethyl; D is a drug as defined in Formula (I).

Formula (XIb)

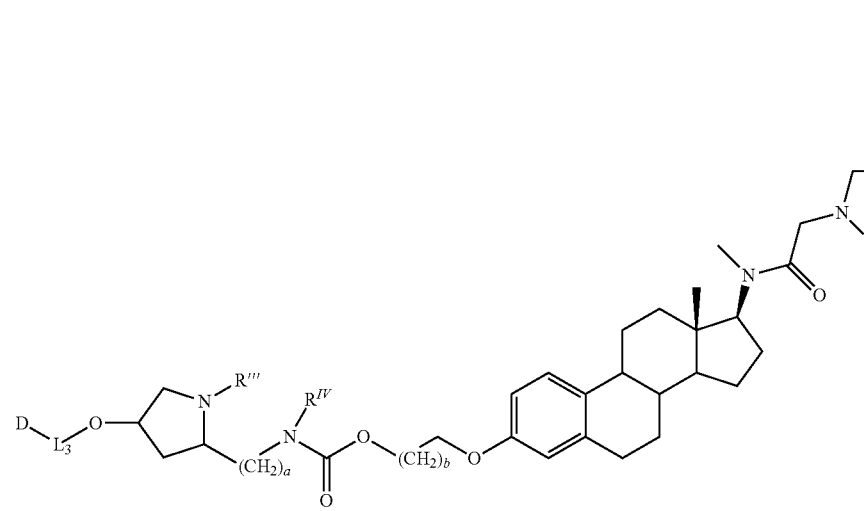

wherein L₃ has the meaning according to Formula (I); a, b and d each stands for an integer of 0, 1, 2, 3, 4, 5 or 6; R", R''', R$^{IV}$, each strands independently for hydrogen, methyl or ethyl; D is a drug as defined in Formula (I).

Formula (XIc)

wherein L₃ and D each have the same meaning as in Formula (I).

Formula (XId)

wherein L₃ and D each have the same meaning as in Formula (I).

In an embodiment of the invention, it provides a Conjugate where E, E' or E" each having independently the structure as set forth in any of Formulae (I), (II); (VII), (VIIa); (VIIIa), (VIIIb), (VIIIc), (VIIId), (VIIIe), (VIIIf), (VIIIg), (VIIIh); (IX), (IXa), (IXb), (IXc), (IXd), (IXe), (IXf), (IXg), (IXh); (X), (Xa), (Xb), (Xc); (XI), (XIa), (XIb), (XIc), (XId); attached to a drug.

Also within the scope of the invention are molecules termed "precursors". A "precursor" in the context of the invention, is a chemical moiety which is used in the synthesis of Conjugates according to embodiments of the invention. Often, the precursor comprises chemical groups, which are destined to be removed or modified during the synthesis of the Conjugate, in stages such as attachment of a therapeutic protein, oligonucleotide or another macromolecule to the MNMs of the invention. Examples for such chemical groups are phosphoroamidite, azide, acetylene or N-hydroxysuccinimide (NHS) groups. Respectively, the invention therefore also discloses such a precursor, being a Compound of the structure as set forth in any of Formulae (I), (II); (VII), (VIIa); (VIIIa), (VIIIb), (VIIIc), (VIIId), (VIIIe), (VIIIf), (VIIIg), (VIIIh); (IX), (IXa), (IXb), (IXc), (IXd), (IXe), (IXf), (IXg), (IXh); (X), (Xa), (Xb), (Xc); (XI), (XIa), (XIb), (XIc), (XId); comprising or linked to as chemical moiety, destined to be removed or modified during the synthesis of the Conjugate.

In an embodiment of the invention, it provides a precursor wherein, the chemical moiety, destined to be removed or modified is selected from the group consisting of phosphoroamidate, activated ester, azide or acetylene.

In one embodiment, the precursor has the structure, as set forth in Formula (XII):

Formula (XII)

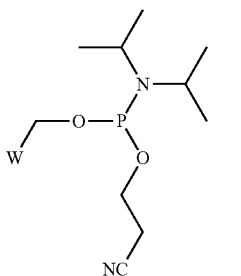

wherein W is a moiety, selected from E, E' or E", as described in to any of Formulae (I), Formulae (I), (II); (VII), (VIIa); (VIIIa), (VIIIb), (VIIIc), (VIIId), (VIIIe), (VIIIf), (VIIIg), (VIIIh); (IX), (IXa), (IXb), (IXc), (IXd), (IXe), (IXf), (IXg), (IXh); (X), (Xa), (Xb), (Xc); (XI), (XIa), (XIb), (XIc), (XId). This precursor is useful, without limitation, for attachment to the 5'-end of an oligonucleotide.

Another precursor of the invention has the structure according to Formula (XIII):

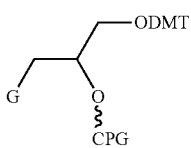

Formula (XIII)

wherein G is a moiety, selected from E, E' or E" as described in any of Formulae (I), (II); (VII), (VIIa); (VIIIa), (VIIIb), (VIIIc), (VIIId), (VIIIe), (VIIIf), (VIIIg), (VIIIh); (IX), (IXa), (IXb), (IXc), (IXd), (IXe), (IXf), (IXg), (IXh); (X), (Xa), (Xb), (Xc); (XI), (XIa), (XIb), (XIc), (XId). This precursor may be useful, among others, for attachment to the 3'-end of an oligonucleotide. DMT is Dimethoxytrityl bis-(4-methoxyphenyl) phenylmethyl; CGP=Controlled Pore Glass.

Still another precursor serves for attachment of D, being an oligonucleotide, at an internal position within the oligonucleotide sequence. For that purpose the precursor has the structure according to Formula (XIV):

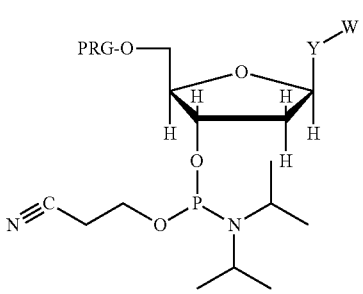

Formula (XIV)

wherein W is as moiety, selected from E, E' or E", as described in to any Formulae (I), (II); (VII), (VIIa); (VIIIa), (VIIIb), (VIIIc), (VIIId), (VIIIe), (VIIIf), (VIIIg), (VIIIh); (IX), (IXa), (IXb), (IXc), (IXd), (IXe), (IXf), (IXg), (IXh); (X), (Xa), (Xb), (Xc); (XI), (XIa), (XIb), (XIc), (XId); and wherein PRG is any protecting group suitable for protecting a hydroxyl group. Examples for such groups are: Dimethoxytrityl bis-(4-methoxyphenyl) phenylmethyl (DMT); acetyl; methoxymethyl ether (MOM);

Y is selected from a 1, 2, 3, 4, 5, 6, 7 or 8 hydrocarbon linker, optionally substituted by oxygen or nitrogen atom(s), and optionally linked to any natural or modified RNA or DNA base. In a preferred embodiment, said base is thymine or uracil.

Yet another precursor serves for attachment of E, E' or E" to D, which is a protein drug. Said precursor has the following structure, selected from the structures of A and B:

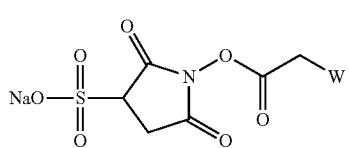

A

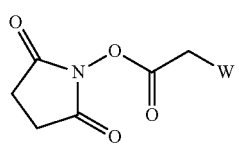

B

Said precursor is aimed at binding to amine moieties of D, wherein W is selected from E, E' or E" according to any of Formulae (I), (II); (VII), (VIIa); (VIIIa), (VIIIb), (VIIIc), (VIIId), (VIIIe), (VIIIf), (VIIIg), (VIIIh); (IX), (IXa), (IXb), (IXc), (IXd), (IXe), (IXf), (IXg), (IXh); (X), (Xa), (Xb), (Xc); (XI), (XIa), (XIb), (XIc), (XId). In other embodiments of the Invention, the precursor has the structure as set forth in any of Formulae (I), (II); (VII), (VIIa); (VIIIa), (VIIIb), (VIIIc), (VIIId), (VIIIe), (VIIIf), (VIIIg), (VIIIh); (IX), (IXa), (IXb), (IXc), (IXd), (IXe), (IXf), (IXg), (IXh); (X), (Xa), (Xb), (Xc); (XI), (XIa), (XIb), (XIc), (XId); wherein at the point of linkage to D there is linkage to a group selected from phosphoroamidite, an activated ester, azide or acetylene. The latter two groups may be useful for attachment to D by "click chemistry", for example without limitation, through the Azide-alkyne Huisgen cyclo-addition reaction.

Embodiments of the invention may further include pharmaceutical compositions, comprising a Conjugate, according to any of Formulae (I), (II); (VII), (VIIa); (VIIIa), (VIIIb), (VIIIc), (VIIId), (VIIIe), (VIIIf), (VIIIg), (VIIIh); (IX), (IXa), (IXb), (IXc), (IXd), (IXe), (IXf), (IXg), (IXh); (X), (Xa), (Xb), (Xc); (XI), (XIa), (XIb), (XIc), (XId); and a pharmaceutically-acceptable salt or carrier.

The invention also comprises methods for specific inhibition of gene expression, in vitro or in vivo. In one embodiment, the method may include utilization of a Conjugate according to any of Formulae (I), (II); (VII), (VIIa); (VIIIa), (VIIIb), (VIIIc), (VIIId), (VIIIe), (VIIIf), (VIIIg), (VIIIh); (IX), (IXa), (IXb), (IXc), (IXd), (IXe), (IXf), (IXg), (IXh); (X), (Xa), (Xb), (Xc); (XI), (XIa), (XIb), (XIc), (XId); or a respective pharmaceutical composition, wherein D is siRNA or an ASO, designed to silence the expression of a specific gene. In some embodiments, the gene encodes far a pathogenic protein, having a role in the etiology or pathogenesis of a disease. In some embodiments, D is as therapeutic protein.

Conjugates according to embodiments of the invention may be used for the treatment of a medical disorder. Embodiments of the invention include methods for medical treatment, comprising the administration to a patient in need therapeutically effective amounts of a pharmaceutical composition, comprising a Conjugate according to any of Formulae (I), (II); (VII), (VIIa); (VIIIa), (VIIIb), (VIIIc), (VIIId), (VIIIe), (VIIIf), (VIIIg), (VIIIh); (IX), (IXa), (IXb), (IXc), (IXd), (IXe), (IXf), (IXg), (IXh); (X), (Xa), (Xb), (Xc); (XI), (XIa), (XIb), (XIc), (XId); wherein D is a drug useful for treatment of the respective medical disorder.

In one embodiment, the method is for genetic treatment with siRNA or ASO, said method comprising the administration to a patient in need therapeutically effective amounts of a pharmaceutical composition, comprising a Conjugate of the invention, according to any of Formulae (I), (II); (VII), (VIIa); (VIIIa), (VIIIb), (VIIIc), (VIIId), (VIIIe), (VIIIf), (VIIIg), (VIIIh); (IX), (IXa), (IXb), (IXc), (IXd), (IXe), (IXf), (IXg), (IXh); (X), (Xa), (Xb), (Xc); (XI), (XIa), (XIb), (XIc), (XId); wherein D is siRNA, an ASO or a therapeutic protein, useful in inhibiting, the expression of a gene which plays a role in the disease of the specific patient.

In another embodiment of the invention, the invention includes a method for medical treatment of a disease by therapeutic a protein, where D is a protein to be delivered across biological phospholipid membranes into cells, or through biological barriers, such as the blood-brain barrier. Said cells are either in cell culture in vitro, or in a living animal or a human subject in vivo. In some embodiments, the cell is a neoplastic cell. In some embodiments, the neoplastic cell is a tumor cell. In some embodiments, the neoplastic cell is a cell within a metastasis. The cell may be a eukaryotic cell, a eukaryotic cell transfected by an oncogenic agent, a human cell, a cell that is a pre-cancerous cell, or any combination thereof. The cell may be a cell within a cell culture, or within a living animal or a human subject.

In yet another embodiment of the invention, D is a protein, administered as a replacement therapy, e.g., to replace a mutated, malfunctioning protein, thus addressing a physiological need. In another embodiment, D is a protein that has as role in gene regulation, including, among others, proteins that have a role in DNA or RNA editing (adding, disrupting or changing the sequence of specific genes). In one embodiment, said protein may be a member of the CRISPRs (clustered regularly interspaced short palindromic repeats) related proteins. Specifically said protein can be or may comprise the Cas9 protein (CRISPR associated protein 9), an RNA-guided DNA nuclease enzyme, or an analogue thereof.

In one of the embodiments of the invention, it describes a method for genetic treatment of a medical disorder, said method comprising administration to a patient in need therapeutically effective amounts of a pharmaceutical composition, comprising a conjugate according to Formula (I), where D is as CRISPR protein, such as Cas9, administered together with an appropriate guide oligonucleotide, thus achieving delivery of the protein, loaded with a respective guide oligonucleotide into the where the CRISPR protein can exert its genome editing activity. A guide oligonucleotide in this context, is a sequence of RNA or DNA that guides the Cas9 protein to a specific locus (place) on the DNA, in order to induce a double-strand DNA cleavage at that site, thus enabling to repair a local defect in the genetic material. In the case of Cas9, the guide oligonucleotide is short segment of RNA, the sequence of which is complementary to the sequence of the target DNA locus.

Therefore, conjugates according to embodiments of the invention, and the respective pharmaceutical compositions and methods may be beneficial, among others, in the treatment of medical disorders, selected among others, from cancer, toxic insults, ischemic disease, infectious disease, protein storage disease, trauma, immune-mediated disease, or a degenerative disease.

According to some embodiments, the medical disorder is cancer. As used herein, the term "cancer" refers to the presence of cells possessing characteristics, typical of cancer-causing cells, such as uncontrolled proliferation, loss of specialized functions, immortality, significant metastatic potential, significant increase in anti-apoptotic activity, rapid growth and proliferation rate, or certain characteristic morphology and cellular markers. Typically, cancer cells are in the form of a tumor, existing locally within an animal, or circulating in the bloodstream as independent cells, as are, for example, leukemic cells.

In the field of neurological, disorders, conjugates according to embodiments of the invention may be useful, among others, in the treatment of neurodegenerative disorders, such as Alzheimer's disease, Motor Neuron Disease, Parkinson's disease, Huntington's disease, multiple sclerosis and Creutzfeldt-Jacob disease.

EXAMPLES

Some examples will now be described, in order to farther illustrate the invention, and in order to demonstrate how embodiments of the invention may be carried-out in practice.

In the following Examples, described are Conjugates, comprising the MNM(s) of the invention, attached to a single-stranded or to a double-stranded oligonucleotide. These Examples demonstrate, for various Conjugates of the Invention, the entire spectrum of the Invention, namely, that the MNM(s) of the Invention are: (i). Successfully synthesized; (ii). Successfully conjugated to as macromolecule drug (e.g., single-stranded or double-stranded DNA or RNA); (iii). Enable efficient delivery of heavily-charged macro-molecules (across hydrophobic phospholipid membranes into cells; and (iv). Enable these macro-molecules, once inside the cells, to reach their sites of action, and exert a useful biological activity (e.g., gene silencing, that takes place in the cytoplasm).

Example 1: A General Method for Synthesis of Conjugates According to Embodiments or the Invention, Comprising Oligonucleotides Initially, a gene to be silenced is chosen, based on its role in disease etiology or pathogenesis. Then, based on bio-informatic methodologies known in the art, the nucleotide sequences are determined (typically 19-21 base-pairs double-stranded RNA for a RISC substrate, or 25-29 base-pairs double-stranded RNA for a Dicer substrate).

Synthesis is carried out in the 3' to 5' direction. Solid phase synthesis is applied, using phosphoramidite building blocks, derived from protected 2'-deoxynucleosides (dA, dC, dG, and T), ribonucleosides (A, C, G, and U), or chemically modified nucleosides, e.g., LNA (locked nucleic acids) or BNA (bridged-nucleic-acids). The building blocks are sequentially coupled to the growing oligonucleotide chain, in the order determined by the sequence of the desired siRNA.

Following the construction of the oligonucleotide, an E moiety of the invention is added as one of the building blocks of the oligonucleotide. The E moiety is added at its precursor form, as described above. For linking the compound to the 5'-end of the oligonucleotide, a precursor according to Formula (XII), comprising a phosphoramidite moiety is utilized. For linking the compound at the 3'-end of the oligonucleotide, a precursor according to Formula (XIII) is utilized. For linking the compound at an internal position along the oligonucleotide, a precursor according to Formula (XIV) is utilized. Among others, this precursor may comprise, an acetylene or azide moiety to mediate linkage, of the E moiety to the oligonucleotide chain. The process is fully automated. Upon completion of the assembly of the chain, the product is released from the solid support into solution, de-protected, and collected. The desired Conjugate is then isolated by high-performance liquid chromatography (HPLC), to obtain the desired conjugated oligonucleotide in high purity. In the case of siRNA, each of a complementary RNA strands is synthesized separately, and then annealing of the two strands is performed in standard conditions as known in the art, to yield the desired double-stranded siRNA.

Example 2: Chemical Synthesis of E Moieties of the Invention (E, E' or E")

The starting material perfluoro-tertbutanol is commercially-available. In this example, the E moieties are designed to be linked to the 5'-end of the oligonucleotide, and therefore, a phosphoramidite moiety is added at the last step of the synthesis, towards conjugation to the oligonucleotide chain.

Example 2a: A Method for Synthesis of an E Moiety According to Formula (VII)

Exemplified is a method for synthesis of a precursor of E moiety of the Invention, according to Formula (VIIa), designated Apo-Si-C4. The precursor is designed for attachment to a 5'-end of an oligonucleotide, and has the following structure:

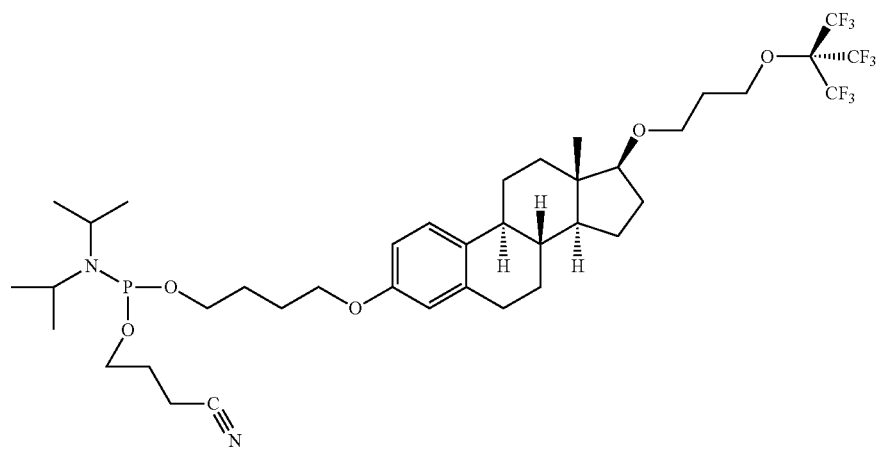

The synthesis starts from estradiol.

Scheme 1

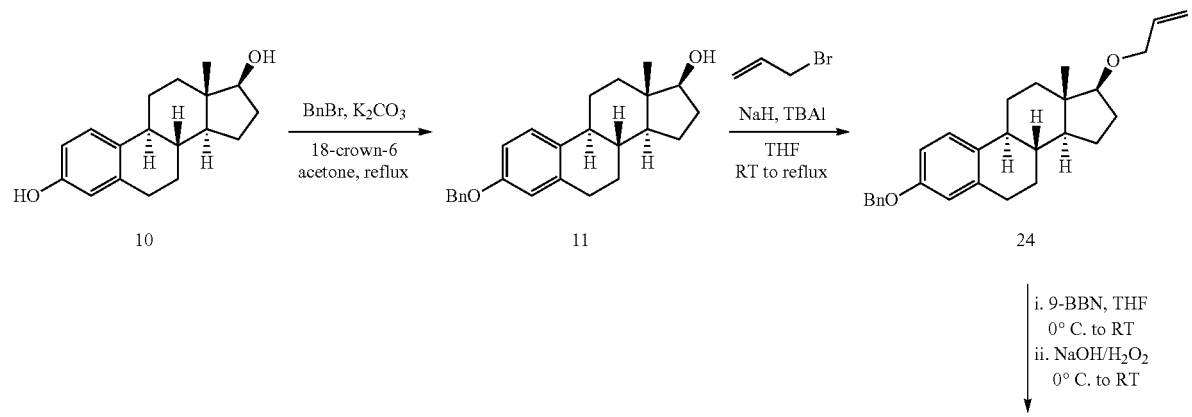

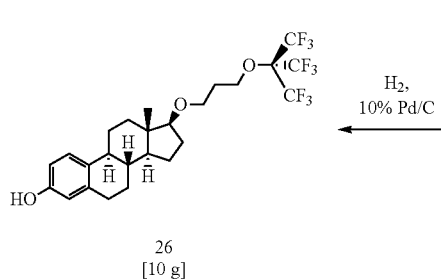
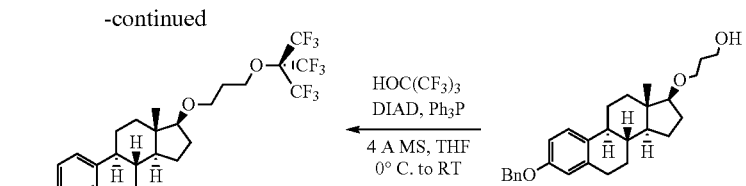
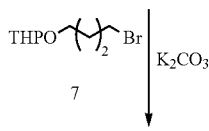
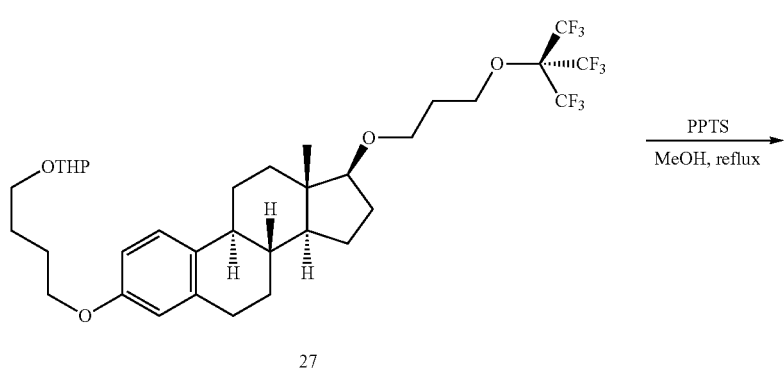
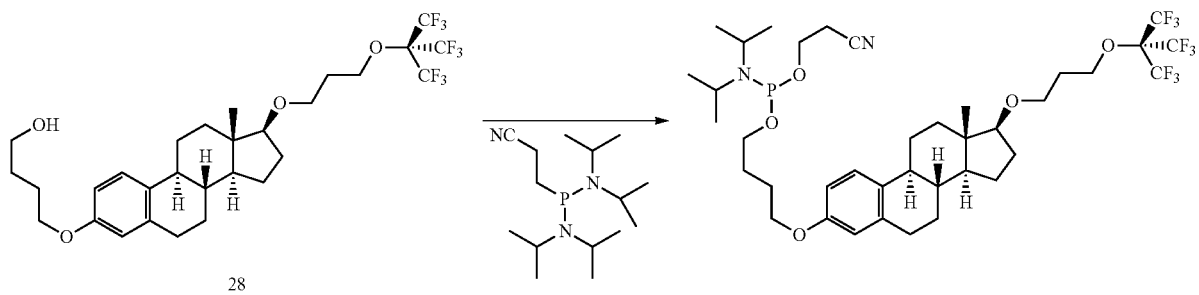

Synthesis was performed according to Scheme 1. For example, estradiol was protected by a benzyl group to provide compound 11. Allylation of alcohol 11 (25.6 g) under optimized reactions conditions (allyl bromide, NaH, cat. Tetra-n-butylammonium bromide (TBAI), tetrahydrofuran (THF), reflux, 16 h) afforded allyl ether 24 (21.85 g, 77%) as a white solid (purified by successive trituration in heptane and MeOH). Regio-selective hydroboration of the terminal alkene 24 (21.8 g) with 9-Borabicyclo[3.3.1] nonane (9-BBN), upon standard oxidative workup (NaOH/ $H_2O_2$) provided alcohol 22. Mitsunobu reaction of the alcohol 22 (13.6 g) with excess perfluoro-tert-butanol under optimized reaction conditions [Diisopropyl azodicarboxylate (DIAD), $PPh_3$, 4 A molecular sieve (MS), THF, RT, 16 h] afforded the desired ether 21. Compound 21 was subjected to catalytic hydrogenation (10% Pd/C, RT) using a mixture (1:1) of THF and 2,2,2-trifluoroethanol as solvent (5 bars, Parr reactor) to afford (after ~18 h) the phenol 26 as off-white solid. De-benzylation was then performed, followed by alkylation, using a Tetrahydropalmatine (THP)-protected bromobutanol. The protecting group was then removed, followed by attachment of the phosphoramidite group, as the last step to the desired compound. This Product was then subjected to conjugation to the oligonucleotide chain, via the phosphoramidite group, as the final building block of synthesis of the oligonucleotide chain, at the 5'-end.

Example 2b: A Method for Synthesis or an E Moiety According to Formula (VII)

Exemplified is a method for synthesis of a precursor of E moiety of the Invention, according to Formula (VII), wherein the estrogen backbone has been exchanged to at residue of lithocholic acid R and R' are each a hydrogen atom; $L_1$, $L_2$, $Q_1$, $Q_2$ are all null, and $L_3$ is a 14-carbon hydrocarbon linker; this Compound is designated Apo-Si-11, shown below as a precursor, linked to a phosphoramidite group, thereby designed for attachment to a 5'-end of an oligonucleotide:

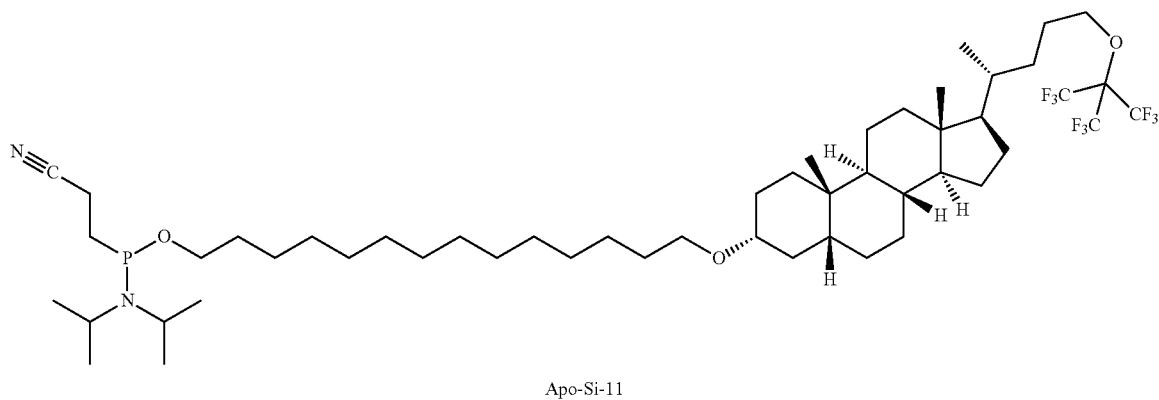 [SMILES: CC(C)N(C(C)C)P(CCC#N)OCCCCCCCCCCCCCCO[C@@H]1CC[C@@]2(C)[C@H](CC[C@@H]3[C@@H]2CC[C@]2(C)[C@@H]([C@H](C)CCCOC(C(F)(F)F)(C(F)(F)F)C(F)(F)F)CC[C@@H]32)C1]
Apo-Si-11
The synthesis started with lithocholic acid, a bile acid that is commercially-available. The synthesis follows synthetic Scheme 2:
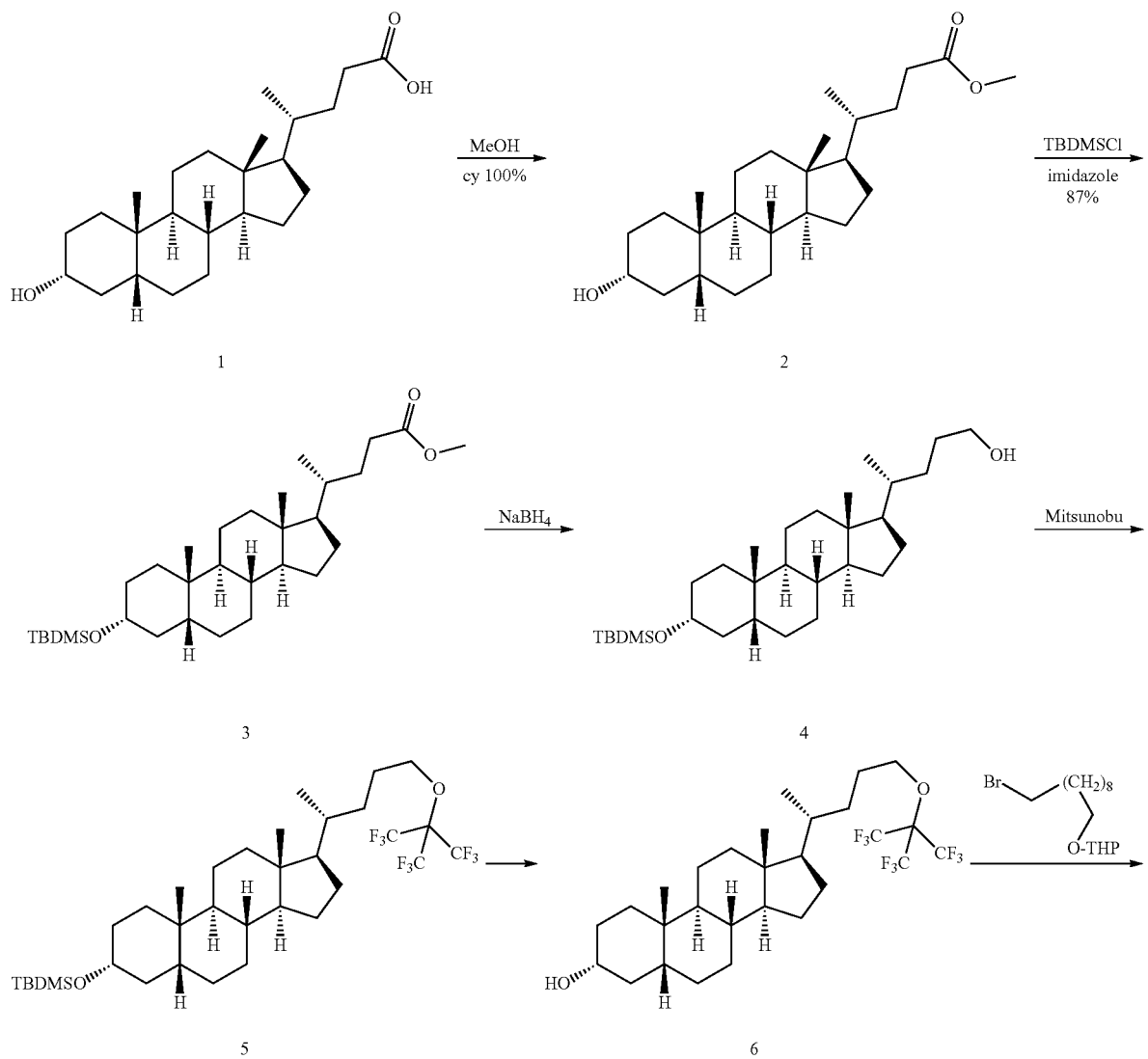
Scheme 2

-continued

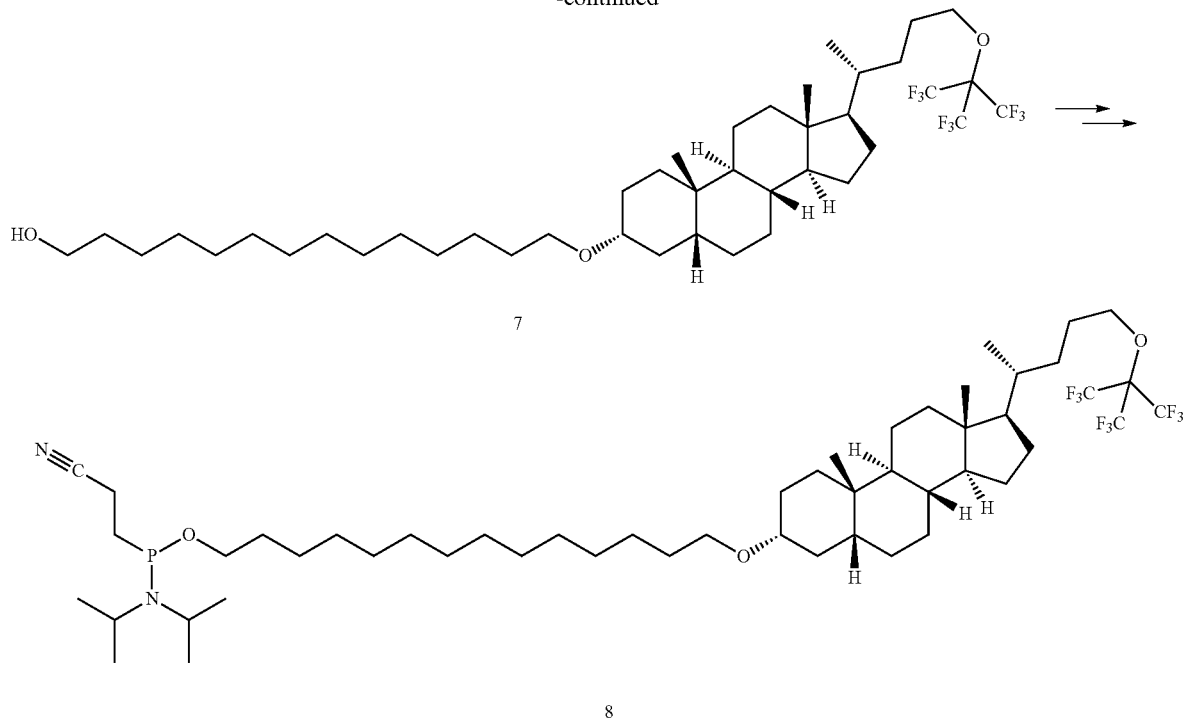

7

8

For example, 25 g of material 1 were converted to corresponding methyl-ester in a quantitative yield. 25 g of material 2 were reacted with tert-Butyldimethylsilyl chloride (TBDMSCl) 29 g, (87%, NMR). Pure compound 3 was obtained. Reduction of compound 3 (29 g) to 4 with NaBH$_4$ THF/MeOH gave, after work up and purification, compound 4 (85%) by NMR, still with some traces of compound 3. Mitsunobu reaction of material 4 with perfluoro t-butanol gave, after work-up column chromatography and trituration from MeOH, 33.5 g (92%) of compound 5, which was de-protected thereafter, to give steroid 6. Steroid 6 (2.5 g) was then coupled to THP-protected bromotetradecanol. The coupling took 3 days, and 4 equivalents of THP-protected bromotetradecanol were needed to reach complete conversion. The product was purified by column chromatography. After removal of the protecting group (THP) with MeOH/1,4-dioxane (HCl, 4 N)/THF, product 7 was purified by column chromatography to remove impurities. Product 7 (1.5 g, c.y. 48%) was obtained as white solid. Product 7 was then converted into the desired compound 8, by attachment of the phosphoramidite group. This Product was then subjected to attachment to the oligonucleotide chain, as the final building block of synthesis of the oligonucleotide chain, at the 5'-end.

Example 2c: A Method for Synthesis of an E Moiety According to Formula (Xc)

Exemplified is a method for synthesis of a precursor of E moiety of the Invention, according to Formula (Xc), which has the following structure. The precursor is designed for attachment to a 5'-end of an oligonucleotide, and has the following structure:

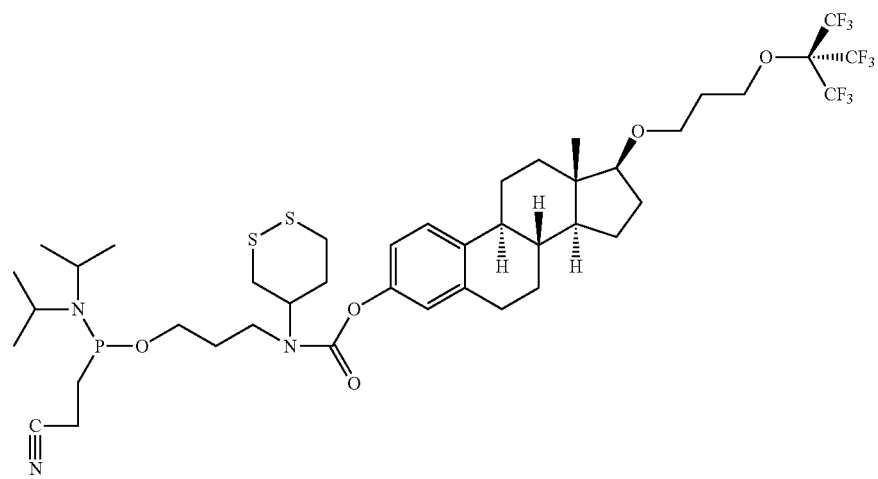

Intermediate 4 was synthesized according to the following Scheme 3.

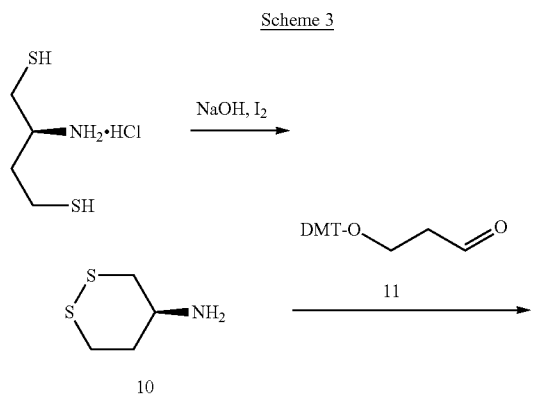

Dithiol-butyl amine (0.5 g) with iodine under basic conditions, afforded the 1,2-dithiane 10 (3.13 g, 90%) as a crystalline-white solid. The alcohol corresponding to intermediate 11 is commercially-available, and was protected with dimethoxytrityl (DMT). Reductive amination with amine 10 (258 mg) in presence of NaBH(OAc)$_3$ afforded the desired secondary amine 4 (330 mg, 91%) as a major product. Intermediate 26 according to Example 2a was then attached to intermediate 4 through carbamoylation, as known in the art. DMT was then removed, and a phosphoramidite group was attached, to yield a precursor compound. This precursor as then subjected to conjugation to the oligonucleotide chain, as its final building block, at the chain's 5'-end. Linkage was performed through an oxygen atom. Said conjugation yielded the desired Conjugate, comprising an E moiety according to Formula (Xc).

Example 2d: A Method for Synthesis of a Key Building Block of Compounds of the Invention (Steroid 1)

Steroid 1 is a major building block of many structures of the Invention. The starting material for the synthesis of Steroid 1 is estradiol. The chemistry developed for the compounds of the invention, comprises attachment of a perfluoro-tert-butanol, utilizing the Mitsunobu reaction, after protection of the aromatic hydroxyl group. Synthesis was performed a according to the following synthetic Scheme, wherein Bn means a benzyl protecting group; BnBr=benzyl bromide; TBAI=Tetrabutylammonium iodide; THF=Tetrahydrofuran; 9-BBN=9-Borabicyclo[3.3.1]nonane; DIAD=Diisopropylazodicarboxylate

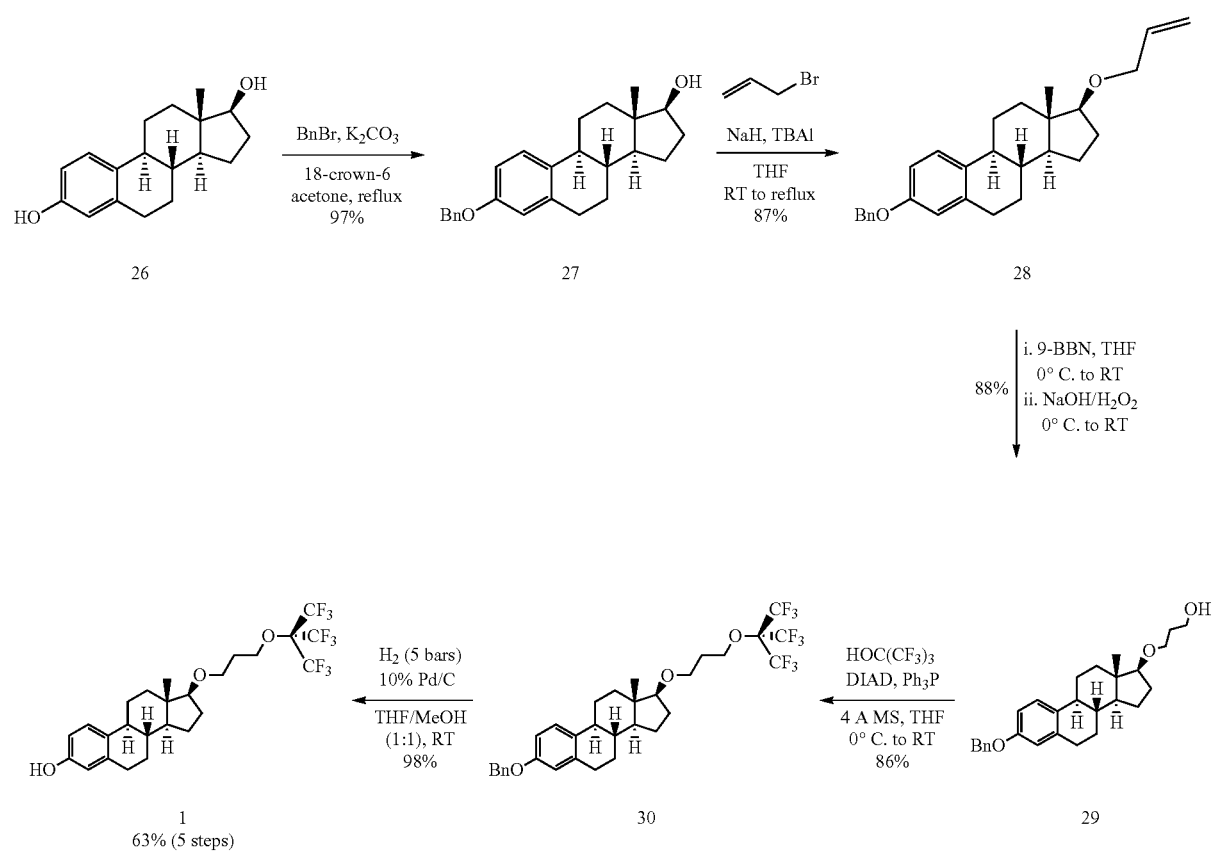

Example 2e: A Method for Synthesis of the E Moiety According to Formula (IXb)

The Example describes the synthesis of a precursor for E moiety according to Formula (IXb), wherein a=3; b=0, k=1, having the following structure. This Compound is designated precursor for Apo-Si-S-S:

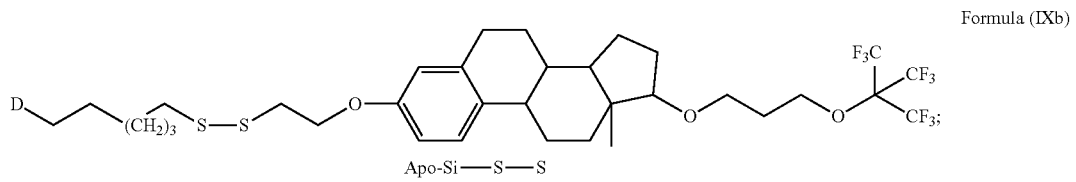

Formula (IXb)

The synthesis was performed according to the following Scheme, starting from key intermediate 1, as described in Example 2d:

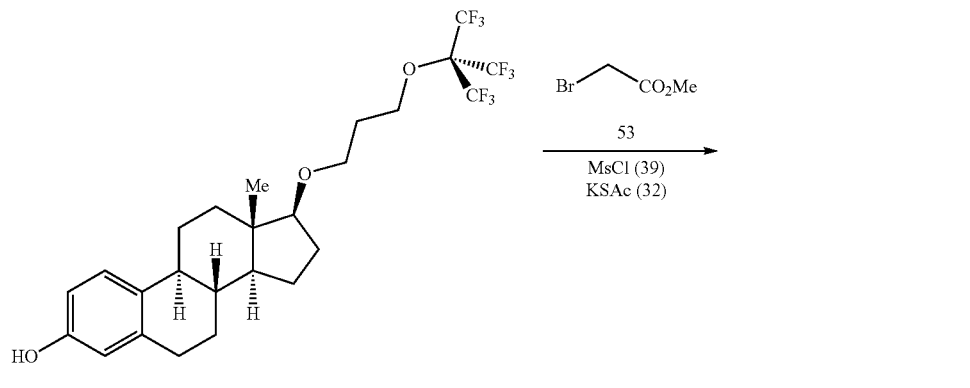

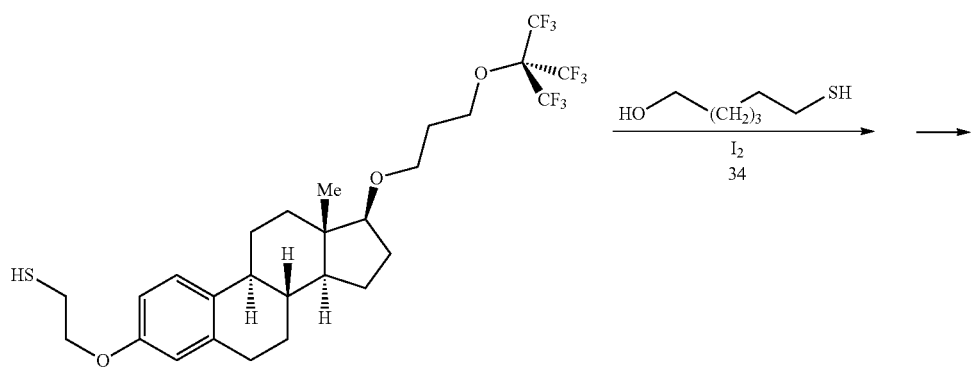

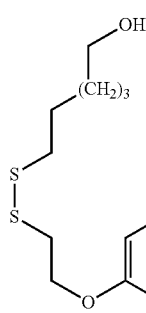
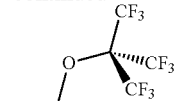
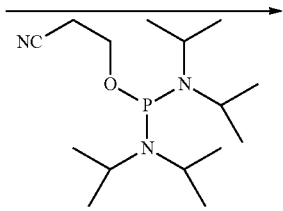

35

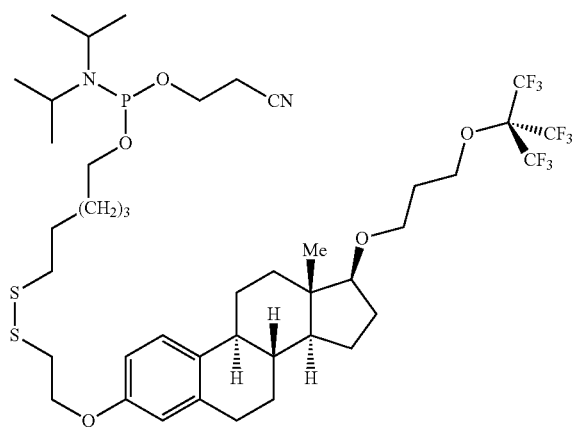

APO-Si-SS

Compound 1 (5 g) alkylated to 53, resulting in 4.95 g isolated material. It was reduced using LiAlH₄, and subsequently protected with mesyl-chloride (MsCl) (4.56 g of the mesylate). Conversion toward acetate 32, utilizing potassium thioacetate (KSAc) was successful, and after purification 4.35 g of 32 were isolated. Deprotection to provide compound 33 using pyrrolidine, and subsequent conversion toward 35, resulted in 9.88 g of crude material, that was subsequently subjected to purification. Crude material of APO-Si-SS, which contained mostly excess of the imidate reagent, was purified with pentane and MeOH, to provide a two-phase system. The supernatant was then decanted, and the white oil was stripped from its solvents to provide a pure precursor for APO-Si-SS (1.33 grams).

Example 2h: A Method for Synthesis of an E Moiety, According to Formula (VIIIb)

The E moiety according to Formula (VIIIb) has the following structure, and is designated Apo-Si-W. The Example describes the synthesis of a precursor, comprising a phosphoroamidite group, for attachment to an oligonucleotide drug, at its 5'-end:

Formula (VIIIb)

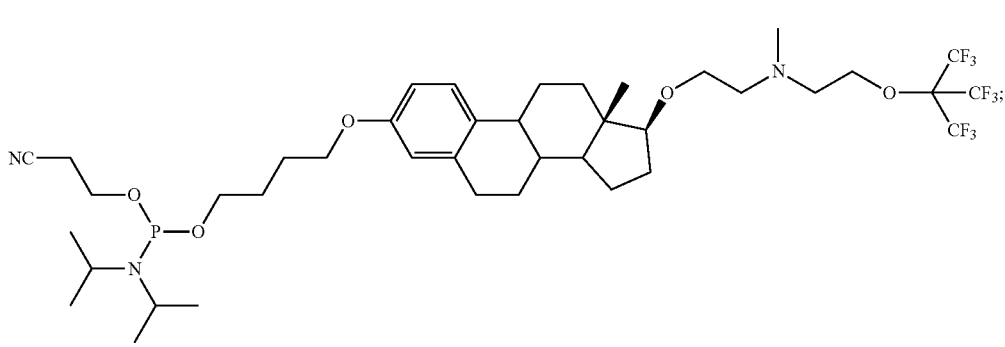

Apo-Si—W

Synthesis was performed according to the following Scheme, starting from Estradiol:

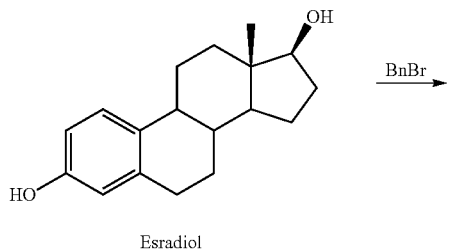

Esradiol

BnBr →

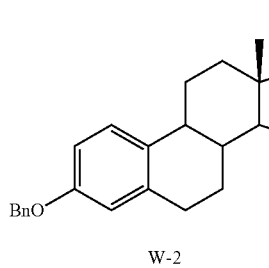

W-2

Allybromide →

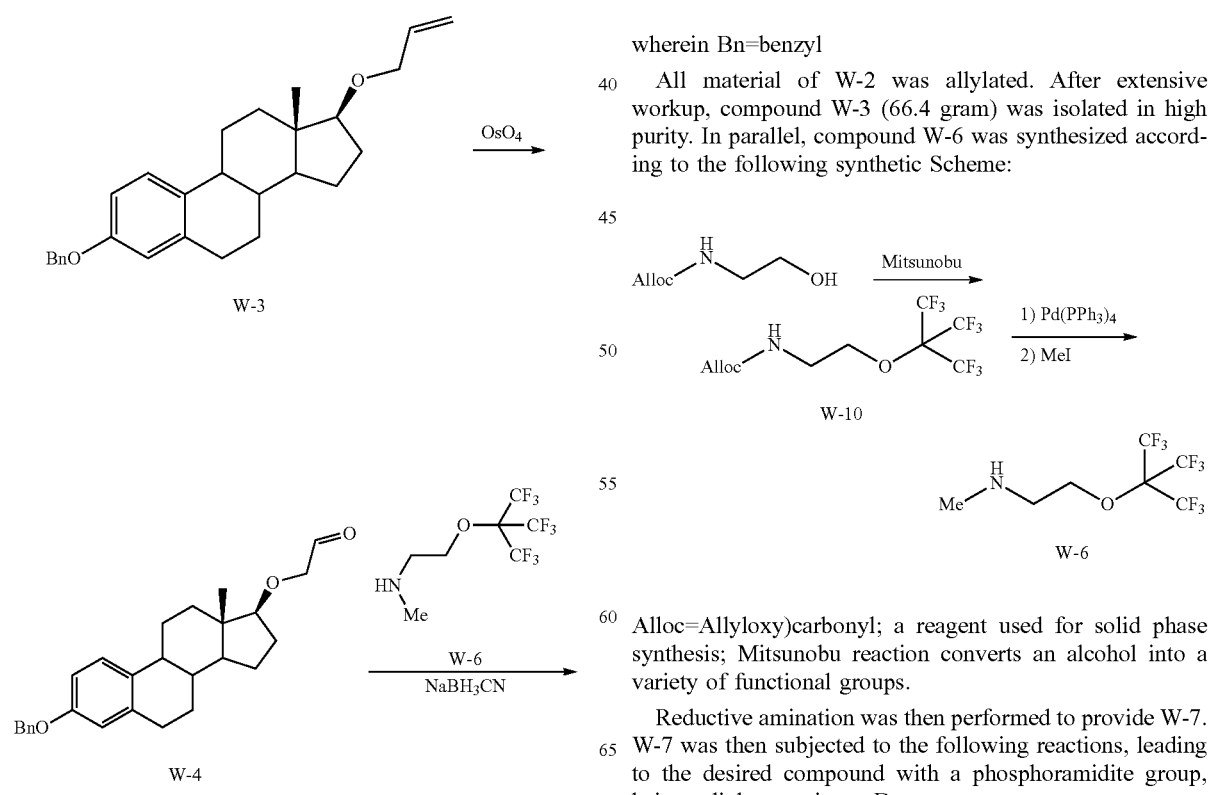

W-3

OsO₄ →

W-4

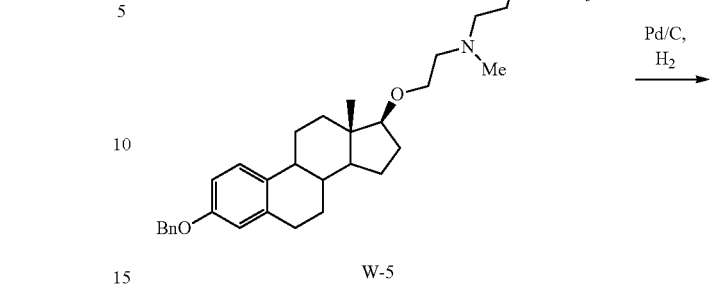

W-5

Pd/C, H₂ →

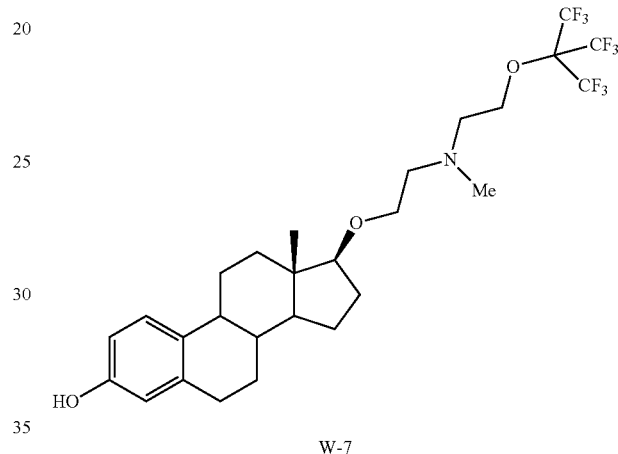

W-7 wherein Bn=benzyl

All material of W-2 was allylated. After extensive workup, compound W-3 (66.4 gram) was isolated in high purity. In parallel, compound W-6 was synthesized according to the following synthetic Scheme:

W-10

1) Pd(PPh₃)₄
2) MeI

W-6

Alloc=Allyloxy)carbonyl; a reagent used for solid phase synthesis; Mitsunobu reaction converts an alcohol into a variety of functional groups.

Reductive amination was then performed to provide W-7. W-7 was then subjected to the following reactions, leading to the desired compound with a phosphoramidite group, being a linkage point to D:

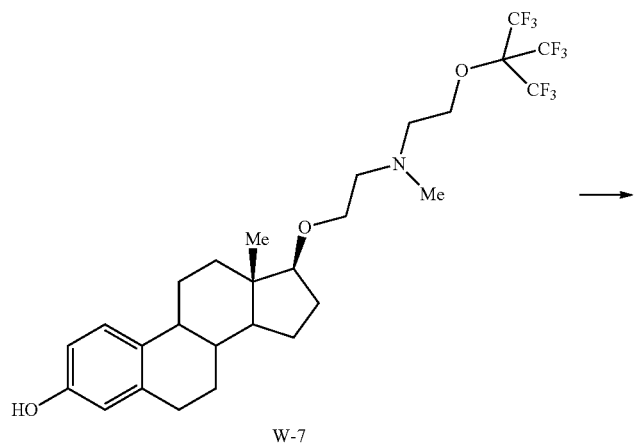
W-7
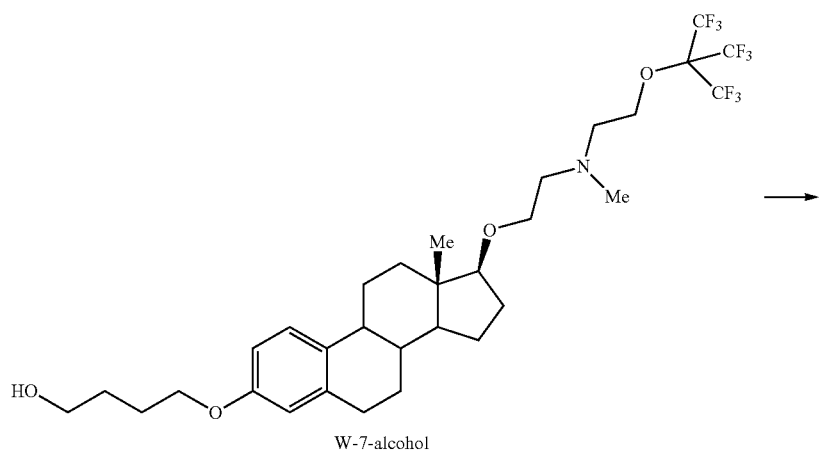
W-7-alcohol
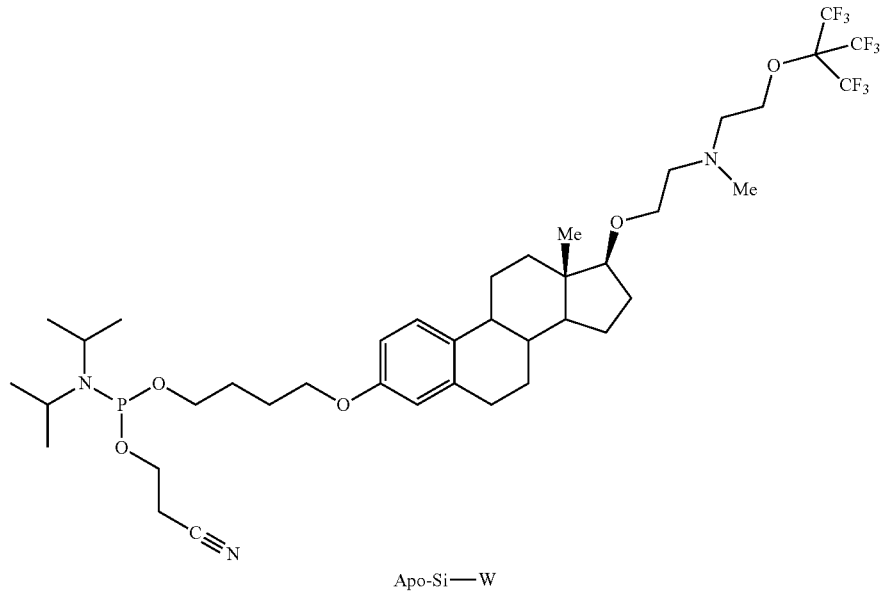
Apo-Si—W

Example 2i: A Method for Synthesis of an E Moiety, According to Formula (VIIIh)

The Example describes the synthesis of a precursor for E moiety according to Formula (VIIIh), having the following structure:

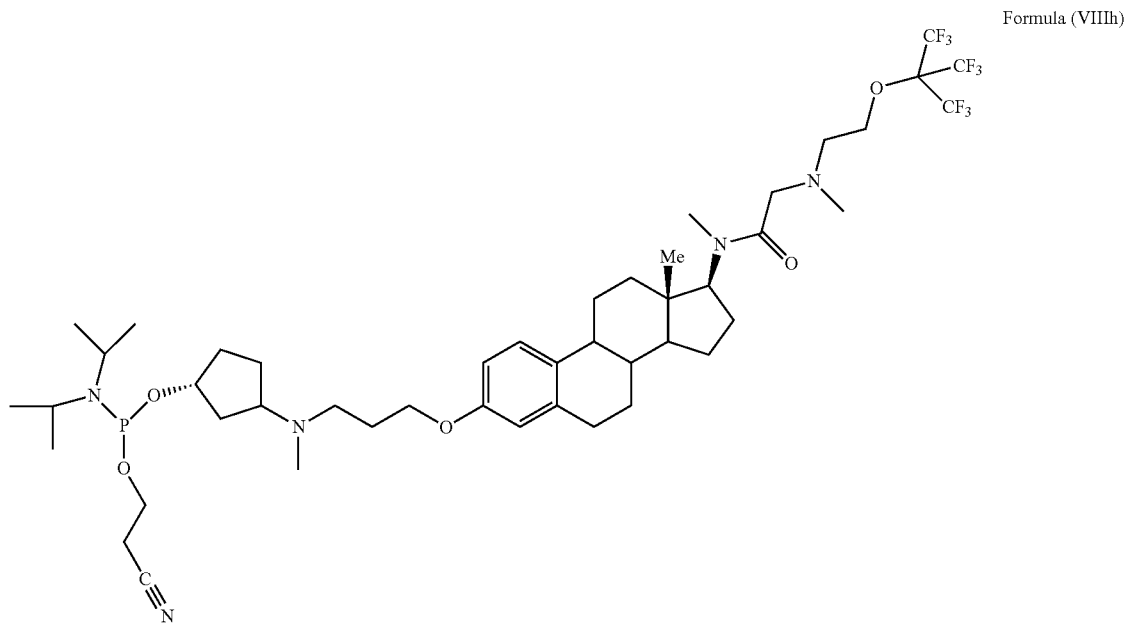 [SMILES: CC(C)N(C(C)C)P(OCCC#N)O[C@@H]1CCC(N(C)CCCOc2ccc3c(c2)CCC2C3CC[C@@]3(C)C2CC[C@@H]3N(C)C(=O)CN(C)CCOC(C(F)(F)F)(C(F)(F)F)C(F)(F)F)C1]

Formula (VIIIh)

Synthesis was performed according to the following Schemes. First, B3-1 described in the Scheme below was synthesized. Alkylation of the readily available starting materials provided B3-2 in good purity and quantity. The Mitsunobu reaction was then performed, to provide 8.5 grams of isolated B3-3.

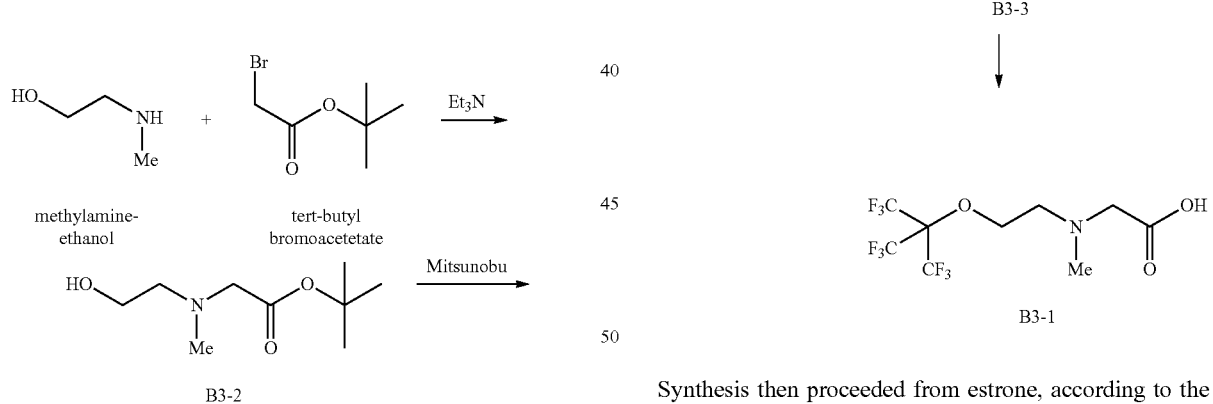

Synthesis then proceeded from estrone, according to the following scheme, to provide the desired compound

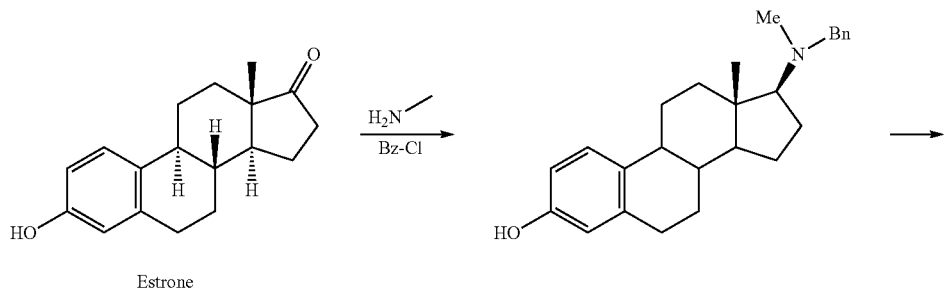

-continued
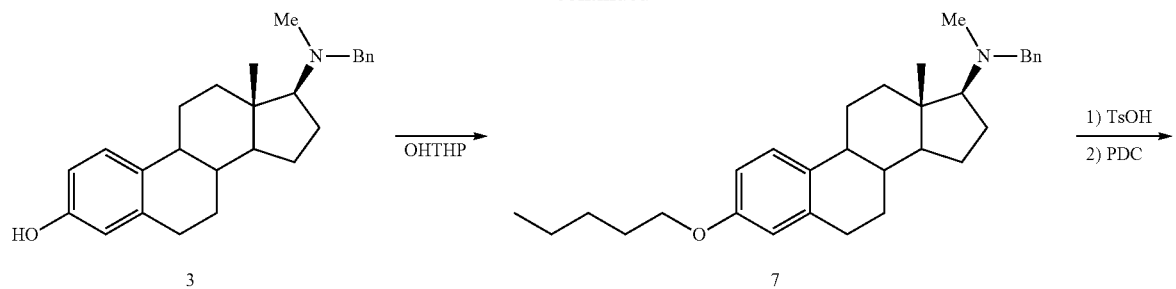
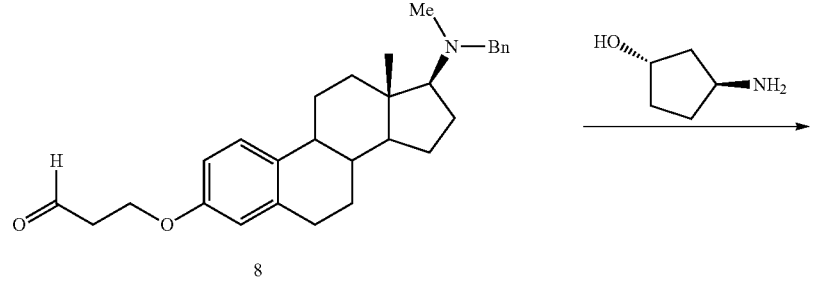
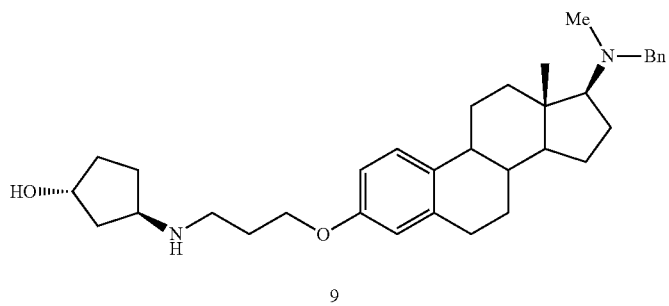
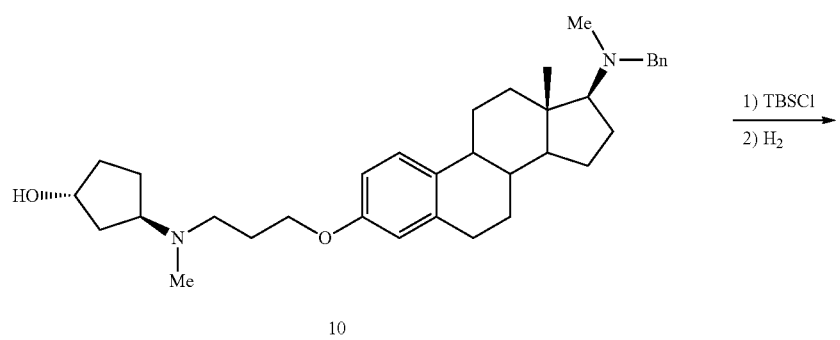
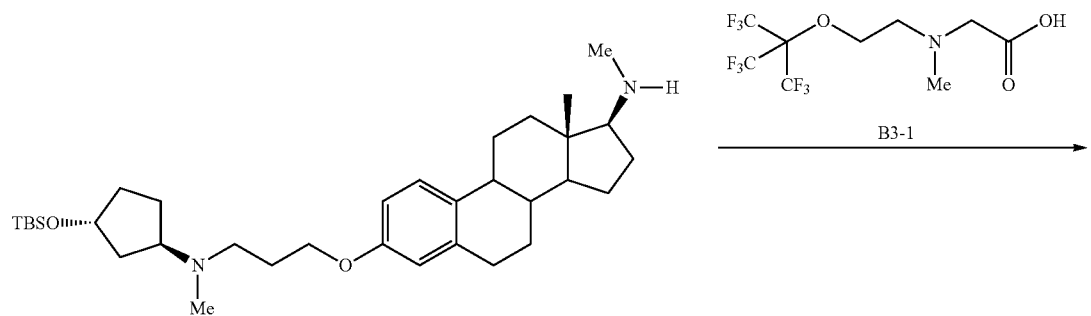

-continued

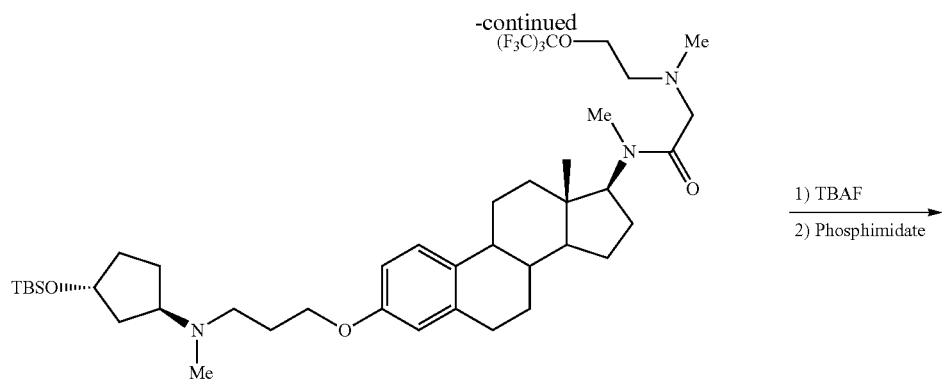

12

1) TBAF
2) Phosphimidate →

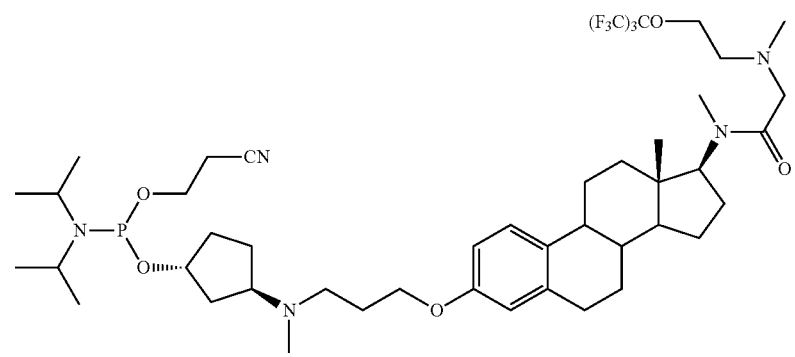

Wherein Bz-Cl=benzylchloride; Bn=benzyl; TsOH=tosylic acid; TBS=tert-Butyldimethylsilyl other; TBAF=Tetra-n-butylammonium fluoride Example 2j: A Method for Synthesis of an E Moiety, According to Formula (IXh)

The Example describes the synthesis of a precursor for E moiety according to Formula (IXh), having the following structure:

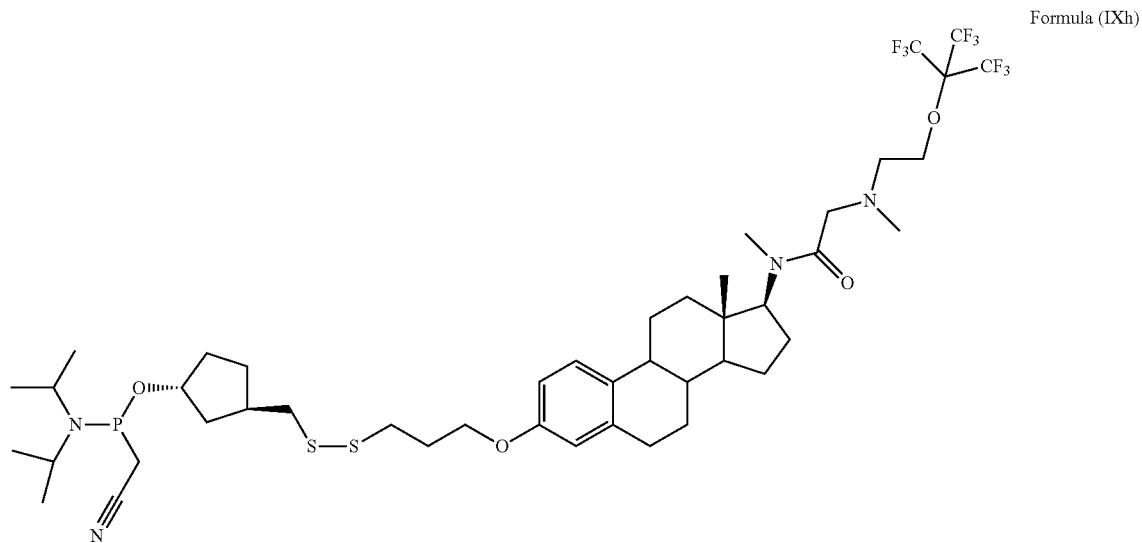 [SMILES: CC(C)N(C(C)C)P(CC#N)O[C@@H]1CC[C@@H](CSSCCCOc2ccc3c(c2)CCC2C3CC[C@@]3(C)C2CC[C@@H]3N(C)C(=O)CN(C)CCOC(C(F)(F)F)(C(F)(F)F)C(F)(F)F)C1]

Formula (IXh)

67

Synthesis started from a hydroxyl-proline derived building block, as shown below.

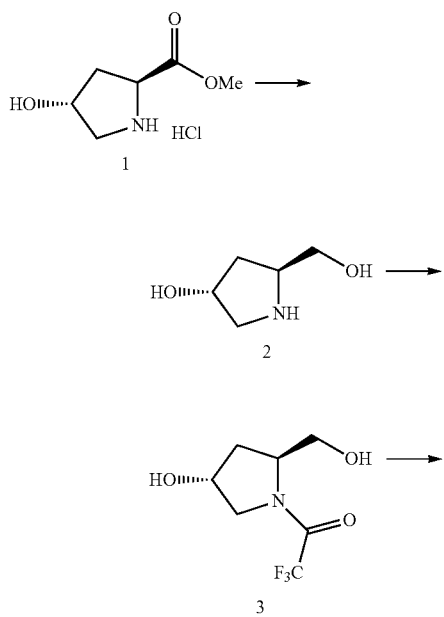

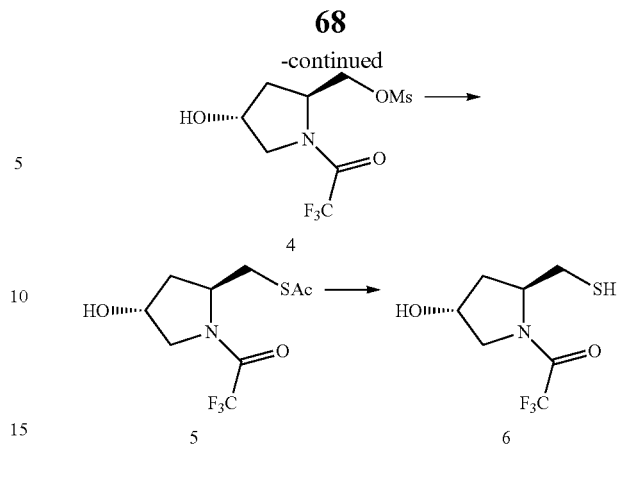

Reduction of proline methyl ester ([CAS #40216-83-9] with NaBH$_4$ gave the corresponding diol. Subsequent treatment with ethyl trifluoroacetate provided acetamide 3. Selective reaction of the primary alcohol with mesyl chloride gave compound 4. Reaction with thioacetate then gave compound 5 that was then subjected to removal of the acetate group. The following steps of the synthesis are described below, to provide the target precursor molecule of the compound according to Formula (IXh).

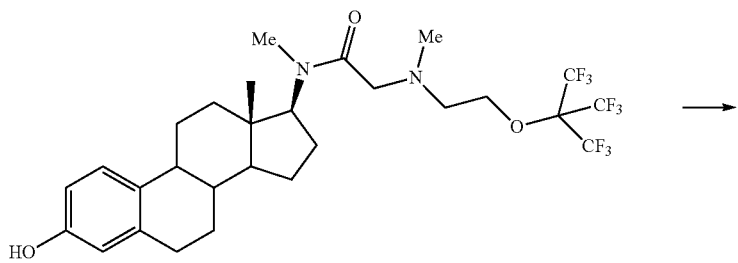

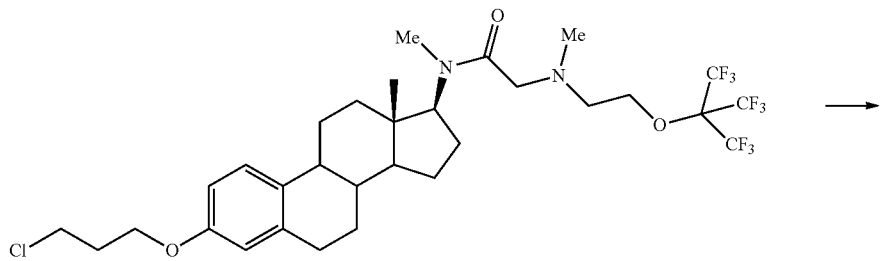

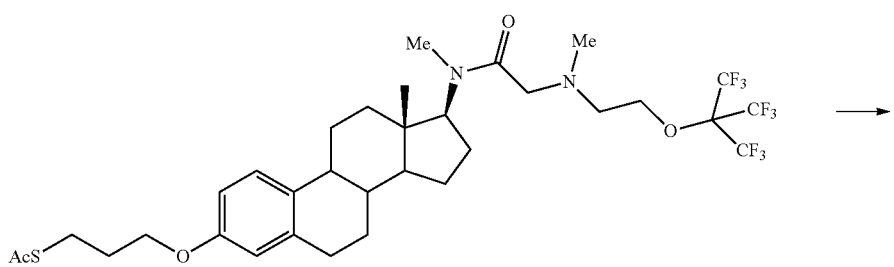

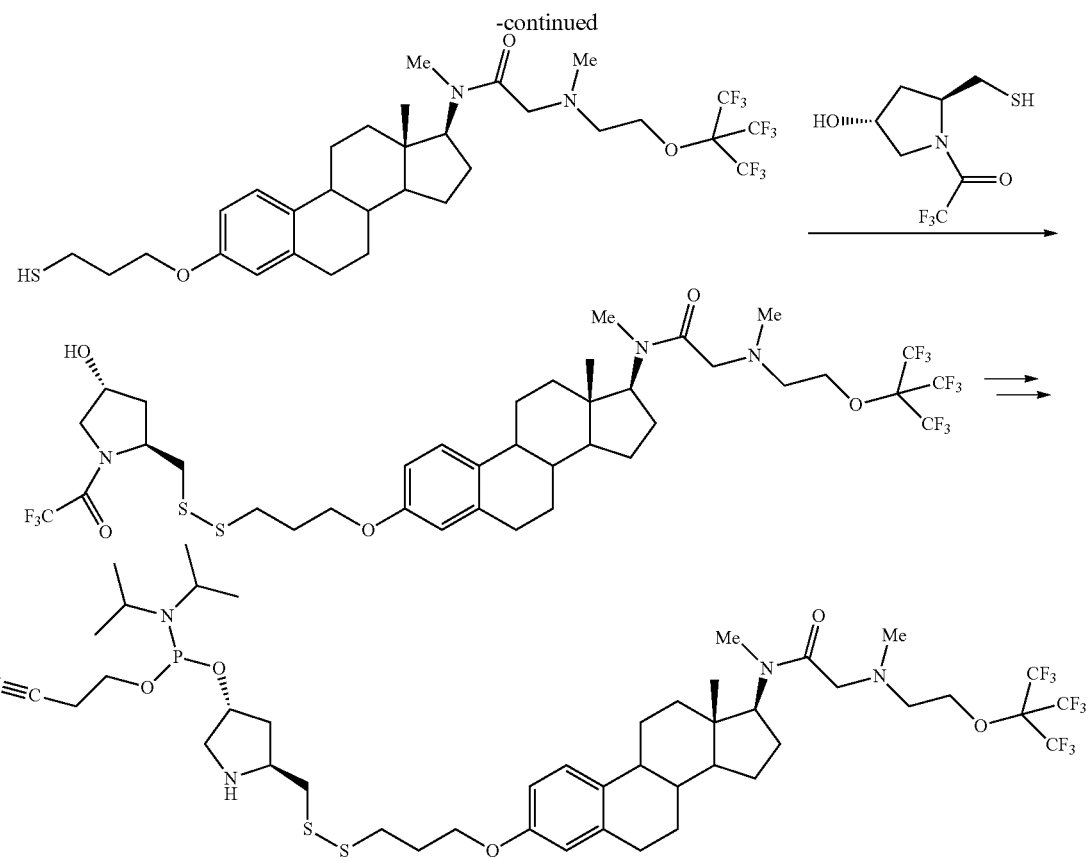

Example 3: Examples of Conjugation of MNM(s) to Oligonucleotide Chains

Examples of structures of precursors and respective compounds, when conjugated to an oligonucleotide chain.

a. Linkage at the 5'-End of the Oligonucleotide:
Precursor:

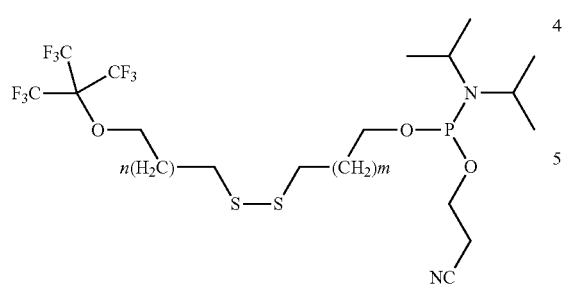

As Attached an Oligonucleotide:

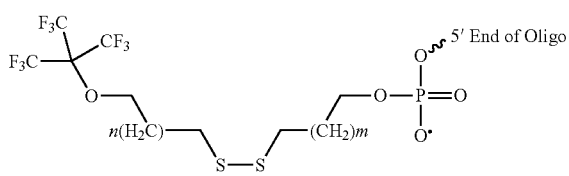

b. Linkage at the 3'-End of the Oligonucleotide:
Precursor

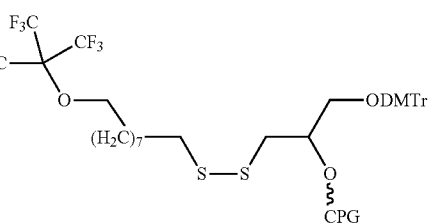

wherein DMT=Dimethoxytrityl; and CPG=Controlled Pore Glass as a solid support for the synthesis of the oligonucleotide.

As Attached to an Oligonucleotide:

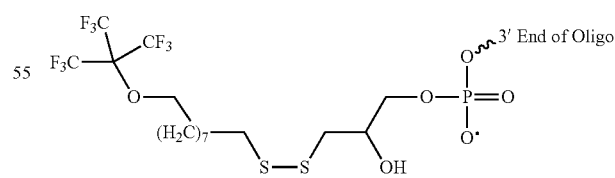

c. Linkage at an Interval Site on Oligonucleotide Chain:
In such case, a nucleotide, (e.g., thymine) is attached to E, serving to anchor it to the oligonucleotide chain. This modification can serve for attachment of in E moiety within an oligonucleotide chain, rather than at a terminal position. It is now exemplified with E having the structure according to Formula (VIIa):

Precursor:

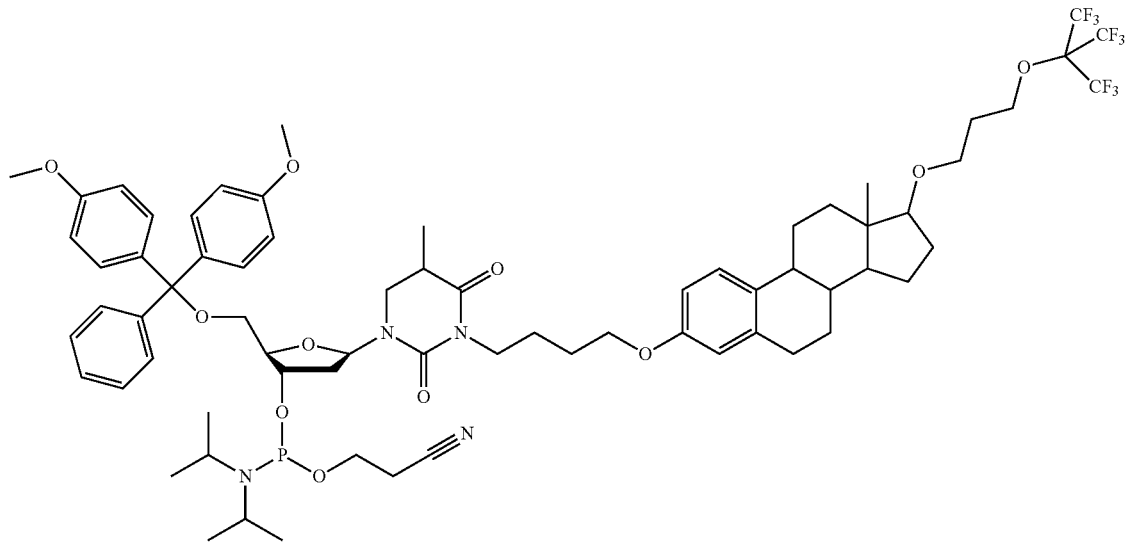

Attached to the Oligonucleotide

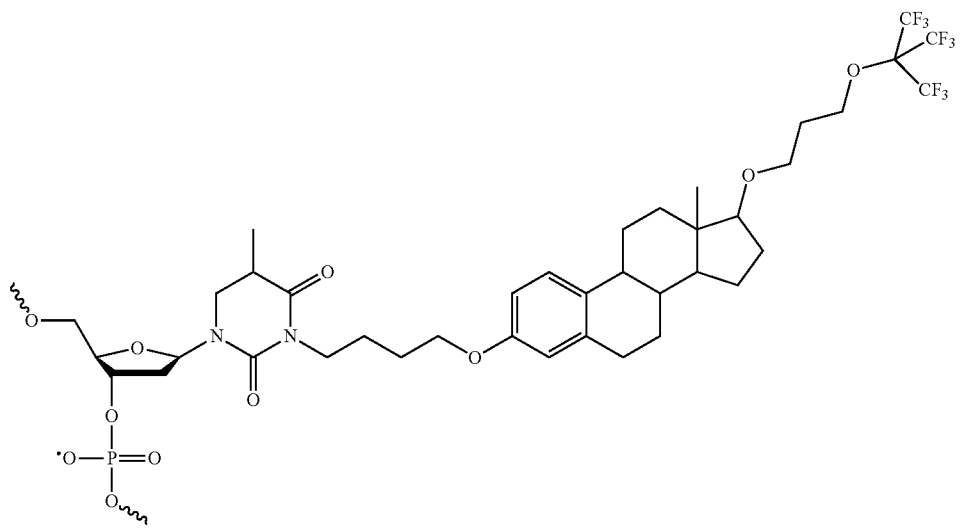

Example 4: An Exemplary Structure of a Conjugate the Invention, Comprising a Protein (for Example, without Limitation, Cas9), Conjugated to E Moieties of the Invention As schematically illustrated below, MNM(s) E, E' or E" according to embodiments of the invention, were attached to a protein through a linker group. Binding was performed through carbamate or amides bonds, to lysine side-chains oil the protein surface. For attachment, active esters were used. For this purpose, an alcohol group was converted into an active ester (e.g., N-hydroxysuccinimide, NHS). Such moiety preferentially reacts with nitrogen of the protein lysine side-chains, over oxygen (water). Reaction as performed according to the following Scheme:

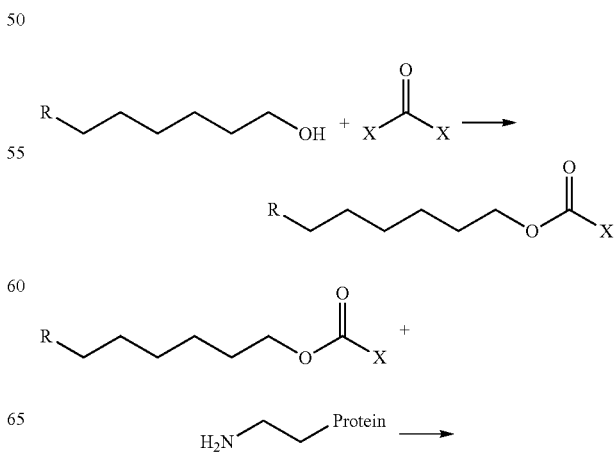

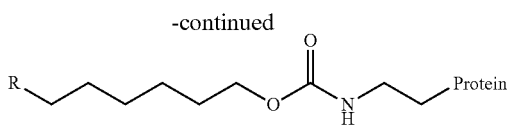

Possible derivatizing agents are:
a) Phosgene: linkage is through chloroformate ester.
b) Disuccinimidyl carbonate (X=N-hydroxysuccinimide): linkage is through a succinimidyl carbonate.
Carbonyldiimidazole (CDI, X=Imidazole): linkage is through imidazolyl carbamates.

Protein labeling with any of these groups takes place in an amine-free [not Tris (Tris(hydroxymethyl)aminomethane)] slightly basic buffer (pH=8-9). The linkage point is hydrophobic, thus requiring a co-solvent [normally DMF (Dimethylformamide), or Dimethyl sulfoxide (DMSO)] for the reaction with proteins to take place. Of the three options above, carbonyl-di-imidazole is preferred, due to its highest nitrogen over oxygen selectivity, and due to a respective synthetic simplicity. The number of E, E' or E" moieties per protein molecule is calibrated and determined by pre-setting of desired molar ratios.

Example 5: Cellular Uptake of Conjugates, Comprising DNA Oligonucleotides, Conjugated to One or to Two Molecular NanoMotors of the Invention FIGS. 5-9 exemplify biological performance in delivery of Conjugates according to embodiments of the invention, comprising MNM(s) of the invention, into various cell types in vitro. Said Conjugates comprise MNM(s) according to Formula (VIIa), wherein a=2, and k=1 (designated Apo-Si-C4); or Apo-Si-11, as specified in Example 2b above. These MNMs were attached to either a Cy3-labeled single-stranded 29-mer DNA sequence (carrying 29 negative charges), or to a double-stranded 58-mer DNA sequence (carrying 58 negative charges), wherein each sequence being labeled by the red fluorophore Cy3. The sequences of the DNA oligonucleotides were 5'-MNM-TT-iCy3-CG-GTGGTGCA GATGAACTTCAGGGTCA (SEQ ID. No. 1); and 5'-MNM-TGACCCTGAAGTTCATCTGCAC-CACC GAA. iCy3 (SEQ. ID. No. 2); means the fluorophore Cy3, at an internal position along the sequence. These sequences (synthesized, for example without limitation, by IDT, Iowa, USA) were chosen randomly, aimed at serving as an example lot the trans-membrane delivery into the cells. The incorporation of the fluorophore served as a tool to detect the localization of the examined Conjugate. Performance in various cell lines is presented, in order to demonstrate that the trans-membrane delivery of macromolecules by the Apo-Si MNMs is universal, and that it is not limited to a specific cell type. It is also noteworthy, that in general. Apo-Si-C4 and Apo-Si-11 manifested a similar performance profile.

Example 5a: 3T3 Cells

In order to assess the ability of an MNM of the invention to deliver a 29-mer single strand DNA (ssDNA) oligonucleotide into cells, an assay in vitro was conducted. One day before experiment. NIH-3T3 cells, stably transfected with the EGFP protein (3T3-EGFP cells) in the exponential growth phase, were plated in 24-well plates, at a density of 4.5×10$^4$ cells/well in DMFM+supplement growth medium (500 µl/well), without antibiotics, initially, a Cy3-labeled 29-mer ssDNA oligonucleotide was tested, having the sequence of 5'-Apo-si-11-TT-iCy3-CGGTGGTGCAGAT-GAACTTCAGGGTCA (SEQ ID. No. 3). Uptake of this Conjugate into cells was compared to the uptake of a control compound, composed of the same DNA strand with Cy3, but W about the Apo-Si-11 MNM. Each Conjugate was diluted in 100 µl/well of Opti-Mem (Life technologies-Cat. 31985062, USA), incubated for 10 minutes in room temperature, and added to the cells at a final concentration of 100 nM. Uptake of the Conjugate by the cells versus Control was evaluated at 8 hours of incubation, when cells were washed with Hank's Buffered Salt Solution (HBSS buffer; Biological Industries, Israel) and subjected to analysis. Cells were visualized using an Olympus fluorescent microscope (BX51TF; Olympus Optical, U.K.) with UV illumination from a mercury lamp (×20 magnitude). The Cy3-fluorophore was visualized with an excitation wavelength of 470-495 nm and emission at 590 nm, while the EGFP fluorophore was visualized with excitation wavelength of 530-550 nm, and emission at 510-550 nm. As shown by fluorescent microcopy in FIG. 5A, Apo-Si-11, comprising Apo-si-11 linked to a 29-mer DNA strand, manifested efficient delivery across cell membranes into the 3T3-EGFP cells, in contrast to the Control oligonucleotide without the MNM, in which no significant uptake was observed.

The ability of the Apo-Si MNM to deliver a 29-mer ssDNA oligonucleotide to 3T3-EGFP cells was also quantified using an ELISA reader (FIG. 5C). For this purpose, cells at an exponential growth phase were plated one day before experiment in 24-well plates, at as density of 4.5×10$^4$ cells/well with DMEM, plus supplemental growth medium (500 µl/well) without antibiotics. Each Cy3-labeled oligonucleotide was diluted in 100 µl/well of Opti-Mem), and added to the cells, at as final concentration ranging from 40 nM to 100 nM. The accumulation of the Apo-Si MNM-Conjugate within the cells, versus the Control Compound without MNM was evaluated at 24 h of incubation. For this purpose, cells were washed with HBSS buffer and subjected to analysis. Detection and quantification of Cy3-positive population were performed using Tecan Infinite® 200 PRO multimode reader (excitation wave length 548±4.5 nm and emission 580±10 nm). Uptake of the Apo-Si MNM Conjugate was compared to the uptake of the control DNA oligonucleotide at the same concentrations, and results were expressed as percentage, compared to Control. As shown in FIG. 5C, a significant uptake of the Conjugate into the cells was observed, as compared to the Control.

Cellular uptake of the Apo-Si MNM, linked to a 29-mer DNA oligonucleotide was also evaluated by flow cytometric analysis (FACS). As described above, one day before the experiment, 3T3-EGFP cells in the exponential growth phase were plated in 6-well plates, at a density of 1.5×10$^5$ cells/well, with DMEM complete medium, without antibiotics. Each of the Cy3-labeled oligonucleotides was diluted in 500 µl/well of Opti-Mem, and added to the cells, at a final concentration varying from 1 nM to 40 nM. Delivery of the Conjugate was evaluated at 24-72 hours post transfection. Following the incubation period, cells were trypsinized, supplemented with Hank's Buffered Salt Solution (HBSS buffer; Biological Industries, Israel) and centrifuged fix 5 min at 1100 rpm. Cells were then re-suspended with Hank's Buffered Salt Solution, and subjected to analysis using FACSAria III Cell Sorter (BD Biosciences, San Jose, Calif., USA), utilizing the Cell Diva software. For each sample, a total of 10$^4$ events were collected. Detection and quantification of the Cy3-positive cell population were performed using measurements of the fluorescence intensity in the cells incubated with the Apo-Si-11 Conjugate, relative to that of the cells incubated with the control oligonucleotide, having the same sequence, but devoid of the MNM.

FACS analysis confirmed that Apo-Si MNM is capable of efficient delivery of a 29-mer ssDNA oligonucleotide into 3T3-EGFP cells. FIG. 5B provides to dot-plot analysis, showing that in the cell population incubated with the Apo-Si-11 Conjugate, practically all cells manifested uptake of the Conjugate, in contrast to Controls, where such uptake did not take place.

The ability of Apo-Si-11 to deliver double-stranded oligonucleotide (dsDNA) across cell membranes was then assessed. For that purpose, two Apo-Si-11 MNMs were attached, one at each 5'-end of a 29 bp dsDNA oligonucleotide, labeled by the cy3 fluorophore, and annealed to generate the double-stranded oligonucleotide. Sequence of the dsDNA was as described above: 5'-Apo-si-11-TT-iCy3-CGGTGGTGCAGATGAACTTCAGGGTCA (SEQ ID. No. 3); and 5'-Apo-si-11-TGACCCTGAAGTTCATCTGCAC-CACCGAA (SEQ ID. No. 4).

Attachment of the MNM to the oligonucleotide was performed as exemplified in Example 3 above, 3T3-EGFP cells were incubated with 40 nM of the Conjugate, cellular uptake was evaluated by fluorescent microscopy at 24 h of incubation, and was compared to the uptake by cells incubated with a Control oligonucleotide of identical sequence, but devoid of the MNMs. As described in FIG. 5D, two Apo-Si-11 MNMs were able to efficiently delivery a 58-mer dsDN A oligonucleotide into the 3T3-EGFP cells.

This delivery was further demonstrated by FACS. For this purpose, 3T3-EGFP cells were plated in 6-well plates, and treated as described in FIG. 5C. Each of the Cy3-labeled oligonucleotide (with or without the MNMs) was diluted in 500 μl/well of Opti-Mem, added to the cells at final concentrations of 40 nM, 10 nM and 1 nM. Following a 24 h incubation period, delivery of the oligonucleotides was evaluated by FACS-Aria III Cell Sorter (BD Biosciences, San Jose, Calif.) and analyzed by the Cell Diva software. A total of $10^4$ events were collected for each sample. Detection and quantification of the Cy3-positive population were performed using measurements of the fluorescence intensity in the cells incubated with the Apo-Si-11 MNMs Conjugate, relative to that of the cells exposed to the Control Oligonucleotide, devoid of the MNMs. As shown in FIG. 5E and FIG. 5F, FACS analysis confirmed that two Apo-Si MNMs are capable of efficient delivery of a 58-mer dsDNA oligonucleotide into 3T3-EGFP cells: FIG. 5E (left and right) shows Dot plot analysis, showing that only cells incubated with the Apo-Si-11 Conjugate manifested DNA uptake into the cells, with accumulation of the conjugate in practically all cells; FIG. 5F. Histogram geomean analysis, indicating a marked signal in the Apo-Si MNM-Conjugate-treated cells, in contrast to a low, background levels in cells treated with the Control oligonucleotide, devoid of Apo-Si-11. A clear dose-response was observed, in the examined concentrations (40 nM, 10 nM, and 1 nM).

Confocal microscopy was used, in order to further confirm uptake of the Conjugate, attached to two Apo-Si-11 MNMs. Cells were prepared as described above. Nuclear staining with the Hoechst 33258 dye (Sigma Aldrich, USA, 1:1000 in HBSS for an hour) was also performed. As shown in FIG. 5G, the Apo-Si Conjugate manifested efficient uptake through the cell membranes and accumulation within the cell.

Example 5b: Murine B16 Melanoma Cells

The objective of this set of experiments was to determine the capability of a Conjugate, comprising two Apo-Si-11 MNMs (each attached at a 5'-end of the strand), to perform uptake into cultured B16 murine-skin melanoma cells. For this purpose, B16 cells were grown and maintained as described in Example 5A. Briefly, cells were grown in DMEM (Sigma Aldrich, USA), supplemented with 10% FBS, 2 mM L-glutamine and 1% Pen-Strep at 37° C., in a humidified incubator containing 5% $CO_2$. One day fore transfection, $2 \times 10^4$ B16 cells were plated in standard 24-well plate chambers. 40 nM of Cy3-labeled 58-mer double-stranded DNA, conjugated to two Apo-si-11 MNMs were incubated with the cells for 24 hours in the presence of complete growth medium. An identical Cy-3-labeled oligonucleotide, devoid of the Apo-Si MNMs was used as control, and was incubated with the cells for the same time-period. Each well was washed twice with HBSS before quantification of Fluorescence. Microscopy figures were taken with an Olympus BX51 microscope as described above.

The B16 cells were also subjected to FACS analysis. For this purpose, one day before transfection, $16 \times 10^4$ B16 cells were seeded in standard 6-well plates. 10 nM and 40 nM of Cy3-labeled 58-mer dsDNA, conjugated to two Apo-si-11 MNMs were incubated for 24 hours with complete growth medium. A Cy3-labeled 58-mer DNA, devoid of the MNMs was used as control. Cells were washed with HBSS, and analyzed for fluorescence intensity with the BD FACSAria™ III as described above.

In addition, confocal microscopy was used, in order to further confirm uptake and intracellular localization of the Apo-Si MNM conjugate, comprising the two MNMs. Cells were prepared as described above. Nuclear staining with the Hoechst 33258 dye (Sigma Aldrich, USA, 1:1000 in HBSS for about an hour) was also performed.

Marked uptake was detected in cells treated with the Apo-Si-11 Conjugate comprising 58-mer double-stranded DNA, but not m the cells exposed to an identical Cy3-labeled oligonucleotide, but without the MNMs. This was evident in the fluorescent microcopy (FIG. 6A), as well as in the FACS analysis (FIG. 6B). At 40 nM, the Apo-Si MNM. Conjugate manifested uptake by 98% of cells. A clear dose-response was observed, comparing signal intensities at 40 nM versus 10 nM. Confocal microscopy (FIG. 6C) further showed efficient uptake of the Apo-Si Conjugate through cell membranes into the cells.

Thus, Apo-Si MNM(s) enable efficient delivery of a 58-mer ds-DNA oligonucleotide into B16 melanoma cells, in a dose-dependent manner.

Example 5c: C26 Murine Colon Adenocarcinoma Cells

In order to demonstrate the capability of Apo-Si MNMs to enable delivery of heavily-charged 58-mer dsDNA into C26 colon adenocarcinoma cells, cells were grown and maintained as described above. Briefly, cells were grown in DMEM, supplemented with 10% FBS 2 mM L-glutamine and 1% Pen-Strep, at 37° C. in a humidified incubator, containing 5% $CO_2$.

Cells were subjected to FACS analysis. For this propose, one day before transfection, $16 \times 10^4$ C26 cells were seeded in a standard 6-well plates. 40 nM of the 58-mer double-stranded DNA, conjugated to two Apo-Si-11 MNMs, each at a 5'-end of the oligonucleotide, and linked to the Cy3 fluorophore, were incubated for 24 hours in the presence of complete growth medium. The same construct, devoid of the Apo-Si MNMs, served as Control. Cells were washed with HBSS, and analyzed for fluorescence intensity with the BD FACSAria™ III as described above.

As shown in FIG. 7, marked Cy3 fluorescence was detected in 98% of cells treated with the Apo-Si-11 Conjugate. Such uptake was not detected in cells exposed to the control oligonucleotide. Therefore, the Apo-Si-11 MNMs enabled efficient trans-membrane delivery of the oligonucleotide.

Example 5d: Human HeLa Cell Line

The objective was to demonstrate the capability of Apo-Si-11 MNMs to enable delivery of heavily-charged 58-mer dsDNA into the HeLa human cervical epithelial carcinoma cell line. For this purpose, cells were grown and maintained as described above. Briefly, cells were grown in DMEM supplemented with 10% FBS 2 mM L-glutamine and 1% Pen-Strep, in a 37° C. humidified incubator, containing 5% $CO_2$.

For the FACS analysis, one day before transfection, $16 \times 10^4$ HeLa cells were seeded in standard 6-well plates, 40 nM of Cy3-labeled, 58-mer double-stranded DNA, conjugated to two Apo-Si-11 MNMs were incubated for 24 hours in the presence of complete growth medium. Cy3-labeled 58-mer DNA was used as control. Cells were washed with HBSS, and analyzed for fluorescence intensity by the BD FACSAria™ III system, as mentioned above. Cells which were treated with 58-mer double stranded DNA, conjugated to two Apo-Si MNMs, manifested marked uptake into nearly all cells in the culture (FIG. 8). By contrast, such uptake was not observed in cells treated by the Control oligonucleotide. Therefore, in conclusion, Cy3-labeled, 58-mer double-stranded DNA, carrying 58 negative charges, and conjugated to two Apo-Si-11 MNMs manifests efficient delivery into human HeLa cell line in vitro.

Taken together, these results, presented in Example 5, and obtained from four distinct cell types: 3T3 murine fibroblast cells, marine melanoma B16 cells, murine C26 colon carcinoma cells, and human HeLa uterine cervical carcinoma cells, demonstrate an efficient trans-membrane delivery and uptake of highly-charged macromolecules, when linked to either one or two Apo-Si-11 MNMs. Such uptake was not observed in control oligonucleotides, devoid of the MNMs. These data support the notion that performance of the MNMs of the invention in enabling trans-membrane delivery of oligonucleotides is universal, and is not limited to a specific cell type.

Example 6: Demonstration of Performance Enhancing Moieties (PEM), Comprising a Dicer Substrate In an embodiment of the invention, it discloses a method for removal of the MNMs for efficient gene silencing, based on the activity of the enzyme Dicer, an endonuclease capable of processing double-stranded RNA, by cutting it at the size of 19-21 base pairs, suitable for interaction with RISC (RNA Inducible Silencing Complex) for gene silencing. Said method comprises: (i). Administration of a Conjugate of the Invention, wherein the oligonucleotide is a Dicer substrate, consisting of a double-stranded RNA of 25-30-nucleotide long, with the sequence selected as per the desired target gene for silencing; and conjugated to 1-2 MNMs of the invention, attached at the 3'-end or the 5'-end of the sense (passenger) strand, and/or at the 5'-end of the antisense (guide) strand; (ii). Trans-membrane delivery of the siRNA, enabled by the MNMs; (iii). Cleavage of the dsRNA by the Dicer enzyme, thus removing one MNM from the Duplex; (iv). Physiological subsequent separation of the double-helix (e.g., by the Argonaute/Helicase enzyme), leading, to release of the intact antisense strand, to interact with RISC, in order to silence the specific target gene (FIG. 3).

In order to demonstrate this mechanism in vitro, 25-27-nucleotide siRNA duplexes (100 pmol), with each strand being conjugated to one Apo-Si-W MNM according to Formula (VIIIb), at the 5'-end; and Control identical dsRNA, devoid of the MNMs, were incubated in 20 ml of 20 mM Tris pH 8.0, 200 nM NaCl, 2.5 mM MgCl2, with 1 unit of recombinant human Dicer (Stratagene) for 24 h. A 3-ml aliquot of each reaction (15 pmol RNA) was then separated in a 15% non-denaturing polyacrylamide gel, stained with GelStar (Ambrex) and visualized using UV excitation. As shown in FIG. 16, the Conjugate comprising two MNMs was effectively cleaved by Dicer, generating shorter ds-RNA fragments, with removal of one of the MNMs. Importantly, the attached MNMs did not cause any significant interference with the efficacy of the Dicer-mediated cleavage, as compared to cleavage of 25-27 dsRNA without the Apo-Si-W modifications. In FIG. 16: Lane#1: 21-nucleotide dsRNA the right size for RISC; lanes#2: Cleavage of a Conjugate, harboring the Apo-Si-W NMN by DICER, with resultant removal of one MNM. Second MNM is still attached, thus slightly slowing Conjugate movement in the gel; Lane#3: 25-27 dsiRNA, with methylations on some of the nucleotides, being substrate for the DICER enzyme; Lane#4: dsiRNA Conjugate, harboring two Apo-Si-W MNMs. Lane#5: 25-27 dsiRNA, without DICER.

These studies in isolated enzymatic system were further supported by the observed efficacious silencing of the EFGP gene, exerted by Conjugates of siRNA comprising Apo-Si-W in live cellular systems, in vitro (Examples 7a 7b).

Example 7a: Silencing of the EGFP Gene by Apo-Si-W Conjugates in HeLa Cells In Vitro The biological system used for this demonstration was human HeLA cells, stably expressing the enhanced green fluorescent protein (EGFP) gene (NIH-HeLa EGFP cells). The administered Conjugate of the Invention comprised siRNA designed to silence the expression of the EGFP gene. Normally, unless utilizing as transfection reagent, such RNA construct cannot pass through the cell membrane into the cytoplasm, where it can exert its gene-silencing activity. Due to conjugation of this siRNA to the MNMs of the invention [for example without limitation, E moieties having the structure as set forth in Formula (VIIIb) (wherein a=2, and $L_3$ is null, designated Apo-Si-W), gene silencing activity was observed, without the need liar a transfection reagent.

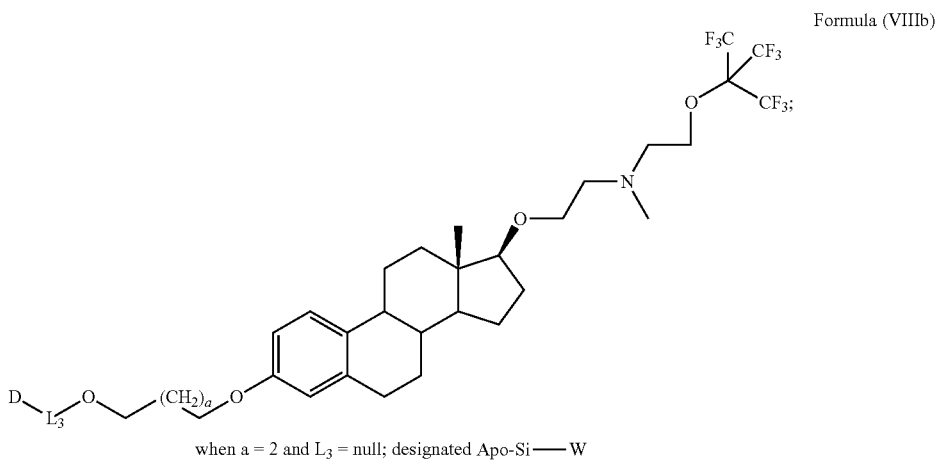

when a = 2 and $L_3$ = null; designated Apo-Si——W

For this purpose, cells were incubated with a Conjugate of the invention, comprising siRNA designed for silencing of the EGFP protein (IDT, Iowa, USA), linked to two MNMs according to Formula (VIIIb). The sequence of the double-stranded RNA was: Sense sequence 5' to 3': ACCCUGAAGUUCAUCUGCACCACCG (SEQ ID. No. 5); Antisense sequence 5' to 3': CGGUGGUGCA-GAUGAACUUCAGGGUCA (Seq. ID. No. 6). A respective double-stranded DNA sequence, linked to the MNM moiety served as Control, since such DNA construct cannot exert gene-silencing activity. Specifically, one day before the experiment, NIH-HeLa EGFP cells at the exponential growth phase were plated in 24-well plates, at a density of $4.5 \times 10^4$ cells/well, with DMEM and supplements growth medium (500 μl/well) without antibiotics. The siRNA-Apo-Si-MNM Conjugate was diluted in 100 μl/well of Opti-Mem (Life technologies), and added to the cells at the final concentration of 40 nM.

Figure 9A:
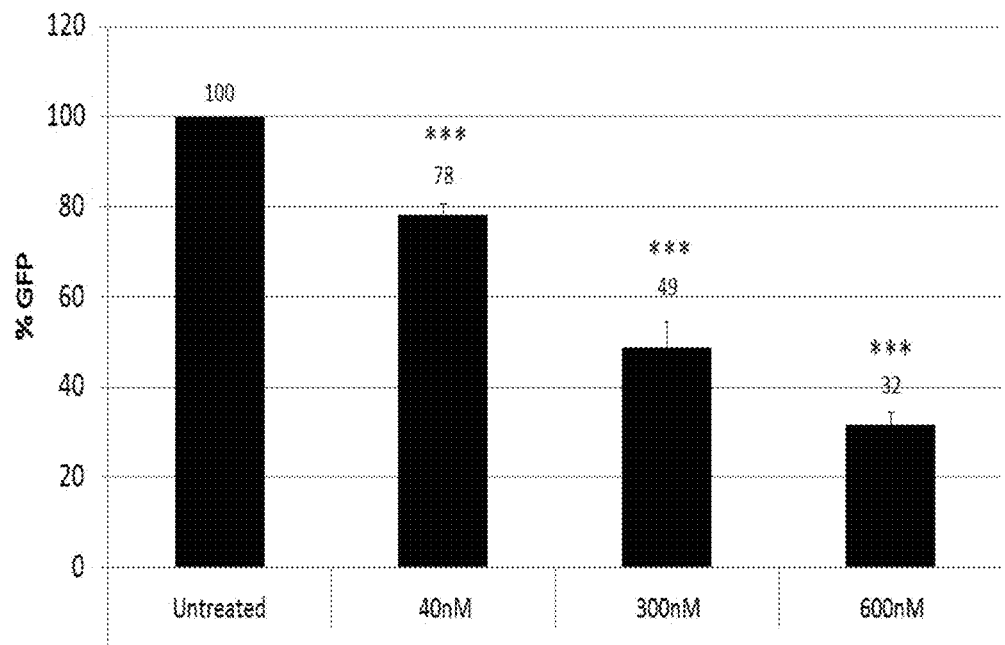

Gene silencing was assessed at 72 hours of incubation. At that time-point, cells were washed with Rank's Buffered Salt Solution (HBSS buffer; Biological Industries, Israel) and subjected to analysis. Detection and quantification of the EGFP-related fluorescent signal was performed by ELISA reader, utilizing Tecan Infinite® 200 PRO multimode reader (excitation wave length 488±4.5 nm and emission 535±10 nm). As shown in FIG. 9A, effective and marked gene silencing was observed with the Conjugate of siRNA, linked to the Apo-Si-W MNMs. Gene silencing took place in a dose-dependent manner, with an average silencing of 22% at 40 nM of the Conjugate, rising to 5% and 68%, at Conjugate concentrations of 300 nM and 600 nM, respectively (p<0.001).

Example 7b: Silencing of the EGFP by Apo-Si-W in 3T3-EGFP Cells In Vitro

Methods:

In order to assess the ability of Apo-Si-W to effectively deliver and silence the expression of the EGFP gene, two Apo-Si-W MNMs were conjugated to the respective siRNA (at the 5'-end of each strand), and the Conjugate was incubated with 3T3-EGFP cells. Cells were seeded in 24-well plates (25,000 cells/well), in antibiotic-free com-

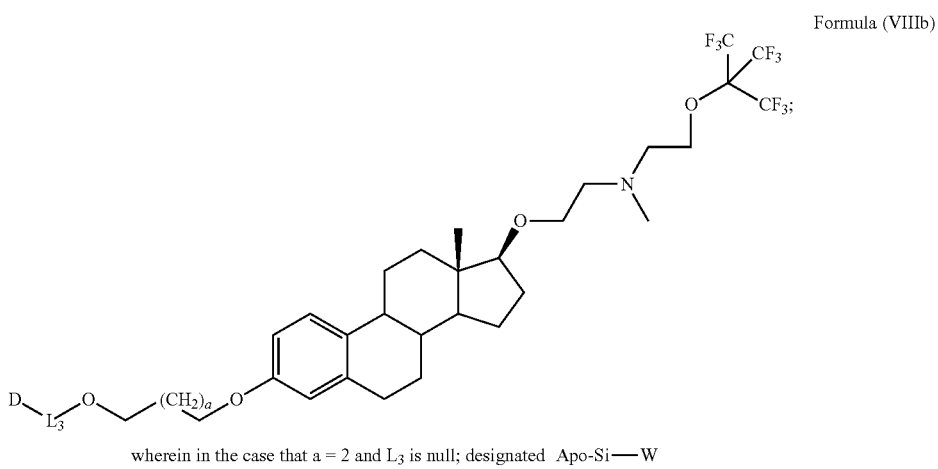

wherein in the case that a = 2 and $L_3$ is null; designated Apo-Si——W plete medium. Cells were incubated in with Apo-Si-W-dsi-RNA in these conditions for 72 hours, except for the first 24 hours, during which serum-free medium was used. 72 hours post transfection, medium was aspirated, and cells were lysed in lysis buffer [50 mM Tris (pH 8), 0.75% Triton X-100, 150 mM NaCl, 1 mM MgCl2, 10% glycerol and complete protease inhibitor (Roche)]). EGFP fluorescence intensity was then quantified with the infinite M200 Pro Multimode Reader (Tecan); with excitation wavelength of 488 nm, and emission wavelength was 535 nm. Cells exposed to the same siRNA sequences, but without conjugation to Apo-Si-W MNMs served as Controls.

Figure 9B:
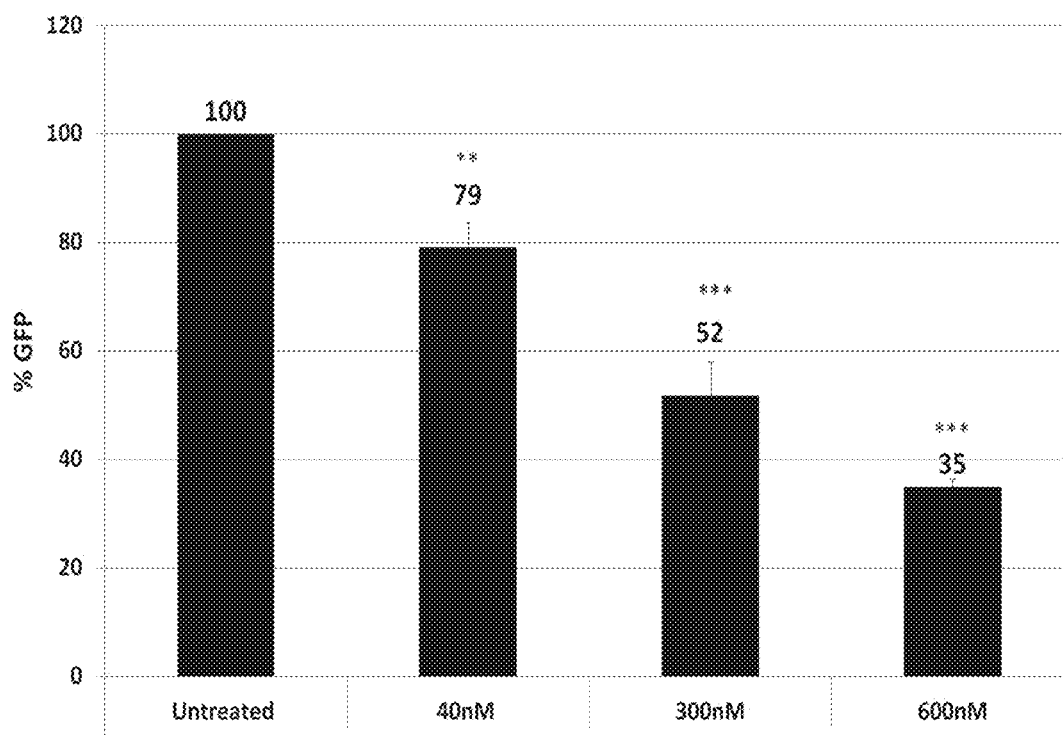

Results:

As shown in FIG. 9B, the Apo-Si-W-siRNA Conjugates exerted a marked, dose-dependent reduction in gene expression, with 65% inhibition, observed at 600 n MM of the Conjugate (p<0.001).

Conclusion:

The Apo-Si-W Conjugate is effective in mediating delivery of EGFP-siRNA to the cytoplasm, and respective gene silencing in EGFP-3T3 cells in vitro.

Example 7c: Gene Silencing of the EGFP Gene in HeLa Cells, by a Conjugate Comprising Apo-Si-S-S MNMs (Formula IXb) In Vitro The Conjugate comprised two Apo-Si-S-S MNMs, according to Formula (IXb), wherein

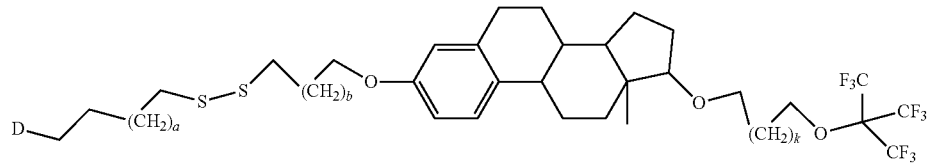

Formula (IXb): In the case that a=3, b=0 and k=1; it is designated Apo-Si-S-S:

The conjugate therefore had the following structure:

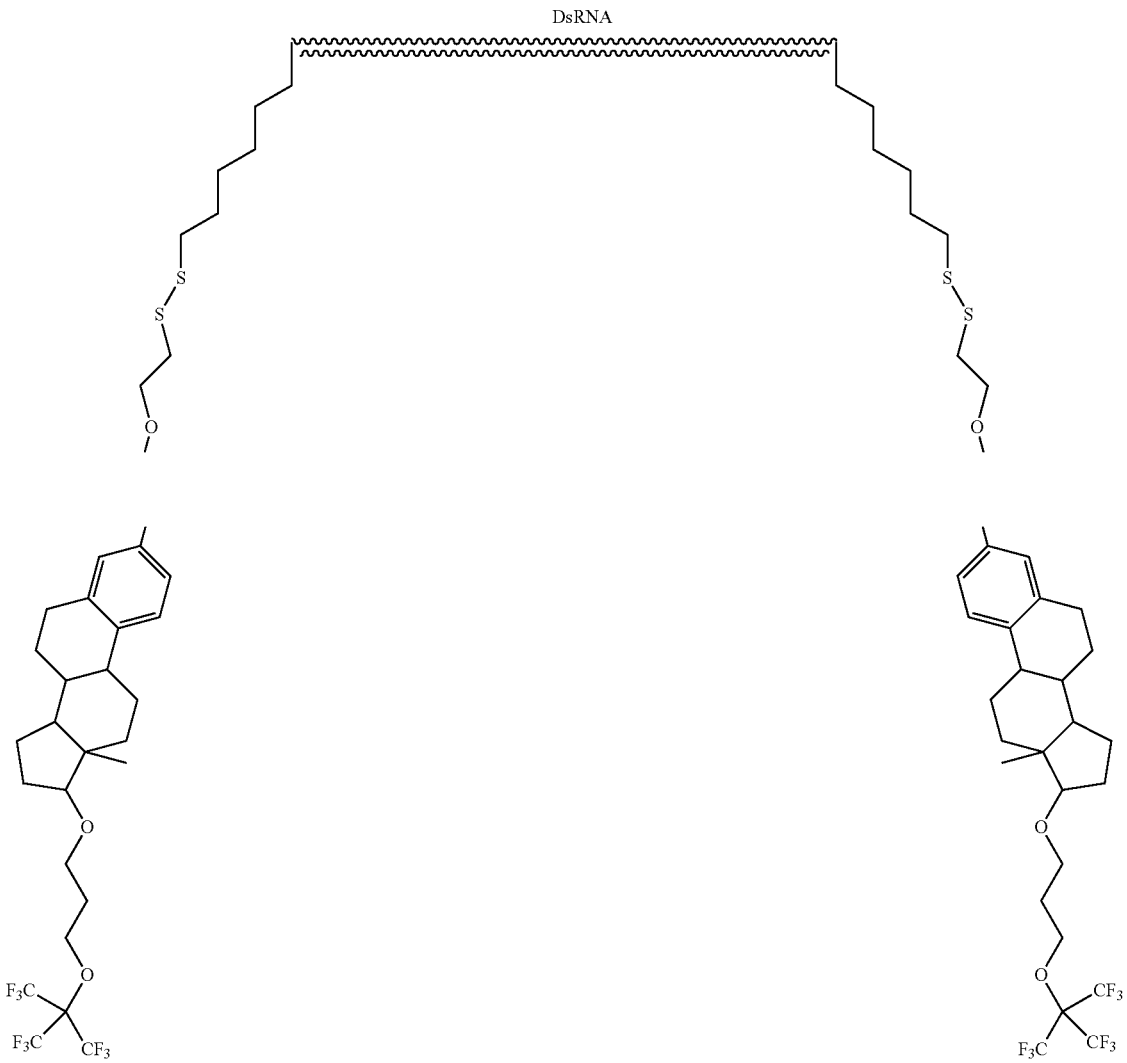

Methods:

In order to assess the ability of the Conjugates of the Invention to silence the EGFP gene, HeLA-GFP cells were seeded in 24 well plates, designed for Fluorescence-based Assays (400,000 cells/well) and incubated with the Conjugates comprising siRNA silence the EGFP gene, of the sequence:

```
Antisense Sequence:
                                          (SEQ ID. No. 7)
5'-Apo-Si-S-S-CGGUGGUGCAGAUGAACUUCAGGGUCA-3';

Sense Sequence:
                                          (SEQ ID. No. 8)
5'-Apo-Si-S-S-ACCCUGAAGUUCAUCUGCACCACCG-3'.
```

The next day, cells were washed with Hank's Balanced Salt Solution (HBSS), and medium was changed to serum free-Opti-MEM (Thermo Fisher Scientific) for 24 hours, followed by 48 of incubation complete medium. 72 Hours post transfection, medium was aspirated, and cells were washed with HBSS. EGFP fluorescence intensity was quantified with the infinite M200 Pro Multimode Reader (Tecan), Excitation wavelength 488 nm; Emission wavelength 535 nm.

Figure 9C:
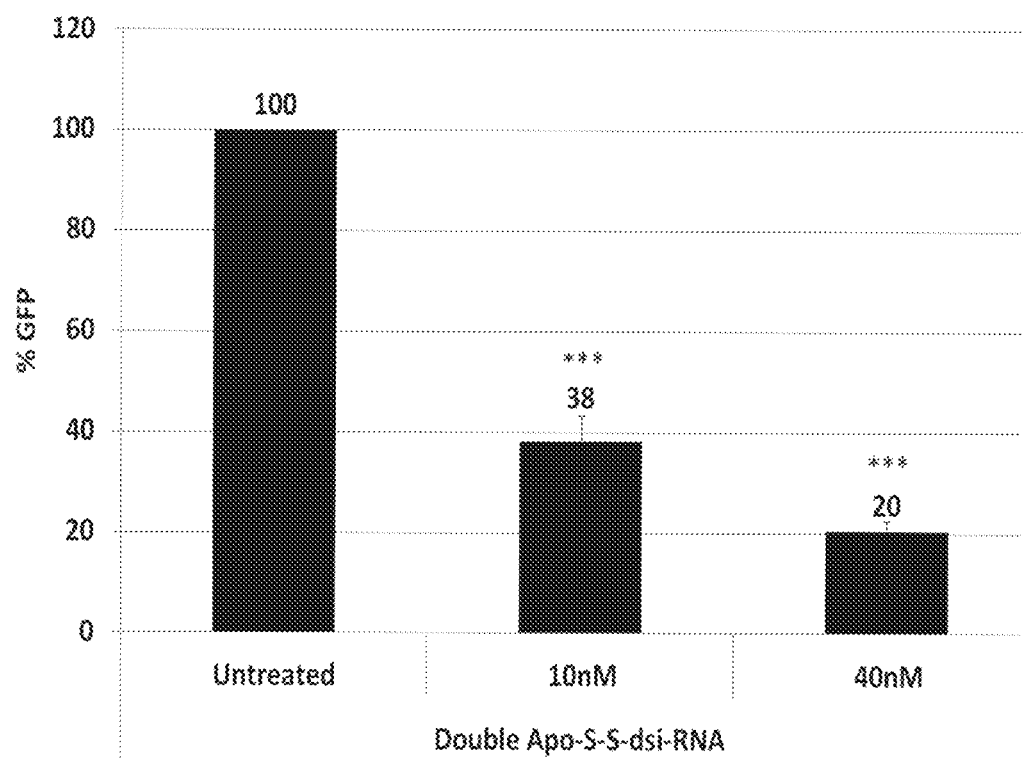

Results:

Silencing of the EGFP gene by Apo-Si-S-S MNM Conjugates is presented in FIG. 9c. As shown, an efficient, dose-dependent silencing, of the EGFP gene was observed. In average, 62% gene silencing was observed with 10 mM of an siRNA Conjugate, comprising two Apo-S-S MNMs, as compared to Control untreated cells. Silencing was increased to 80%, upon increasing the Conjugate concentration to 40 nM p<0.001 (FIG. 9C).

Conclusion:

Conjugates, comprising siRNA linked to two Apo-Si-S-S MNMs manifest robust silencing of the reporter gene EGFP in HeLa cells.

Example 7d: Gene Silencing in 3T3 Cells, Expressing the EGFP Gene, by a Conjugate of the Invention, According to Formula (IXb); APO-Si-S-S, In Vitro Methods:

The experiment was performed as described in Example 7c above with the following modifications: NIH-3T3 mouse fibroblast cell lines, expressing the EGFP protein, were grown and maintained in DMEM, supplemented with 10% FBS 2 mM L-glutamine and 1% Pen-Strep at 37° C., in a humidified incubator, containing 5% $CO_2$. Cells were then incubated for 72 hours with the above Conjugate, at concentrations of 40 nM, 150 nM and 300 nM. Subsequently, the intensity of the EGFP protein fluorescence was quantified utilizing an ELISA reader. In parallel, as Controls, served cells that were not exposed to any treatment (untreated).

Results:

Dramatic silencing of the gene expression was observed in cells treated by the Apo-Si-S-S Conjugate. The extent of the observed EGFP gene silencing was 90.0%, 91.5%, and 92.0% (+0.1%), in the cells treated with 40 nM, 150 nM and 300 nM of the Conjugate, respectively.

Conclusions:

This Example therefore demonstrates that the "Molecular NanoMotor(s) (MNMs) enable: (i). Trans-membrane delivery of the otherwise membrane-impermeable siRNA. (ii). Navigation of the E-RNA-E' Conjugate into the cytoplasm, and; (iii). Exertion of the desired performance of gene-silencing protein complexes comprising the conjugates of the invention. Notably, this Conjugate comprised an MNM linked to a cleavable group (a disulfide moiety), thus demonstrating the performance of a cleavable group, incorporated within the Conjugate of the invention.

Example 7e: Silencing of the EGFP Reporter Gene by Conjugates Comprising Apo-Si-G MNMs In Vitro

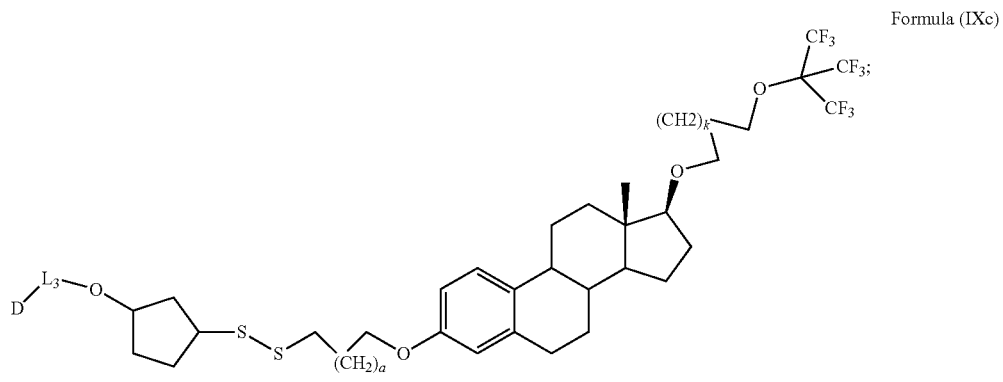

Formula (IXc)

in the case that a = 1, k = 1, $L_3$ = null; the moiety is designated Apo-Si——G

Methods:

In order to assess the ability of Apo-Si-G MNM conjugates to knockdown the EGFP gene in 3T3-GFP cells, cells were seeded in 24 well plates, designed for Fluorescence-based Assays (40,000 cells/well) and incubated with the Conjugates comprising Apo-Si-S-S. The next day, cells were washed with Hank's Balanced Salt Solution (HBSS), and medium was changed to serum free-Opti-MEM (Thermo Fisher Scientific) for 24 hours, followed by 48 of incubation in complete medium. 72 Hours post transfection, medium was aspirated, and cells were washed with HBSS. EGFP fluorescence intensity was quantified with an infinite M200 Pro Multimode Reader (Tecan); Excitation wavelength 488 nm; Emission wavelength 535 nm.

Figure 9D:
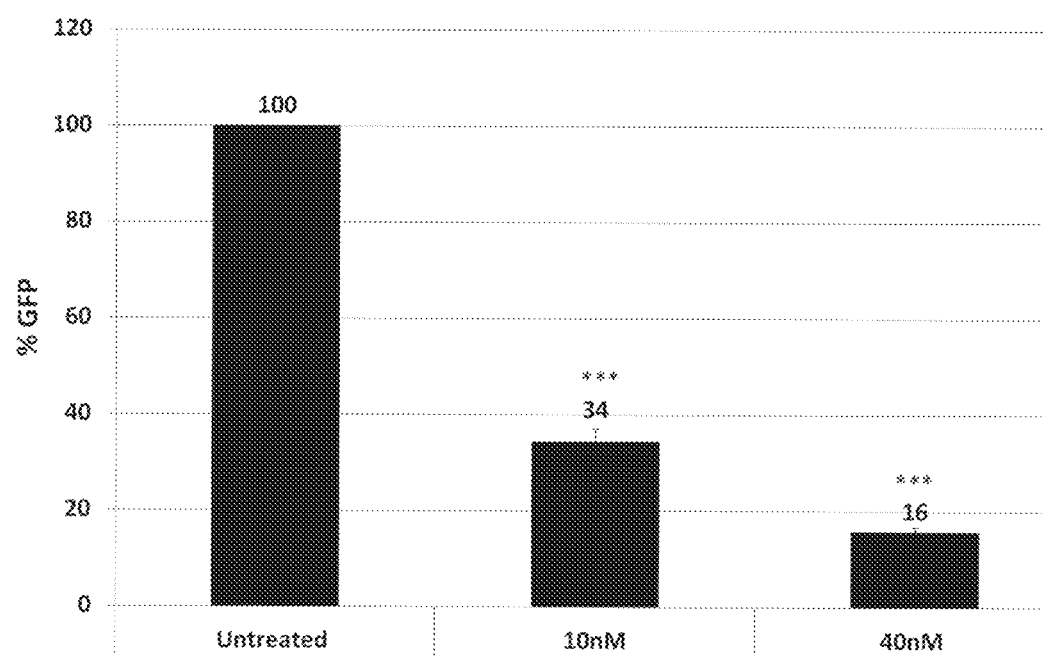

Results:

EGFP gene silencing by the Apo-Si-G MNM Conjugates is presented in FIG. 9d. As shown, Conjugates comprising Apo-Si-G manifested in average 66% silencing at Conjugate concentration of 10 nM, rising to 84% silencing at 40 nM (p<0.00.1).

Conclusion:

Conjugates, comprising siRNA, linked to two Apo-Si-G MNMs manifest efficacious silencing, of the reporter gene EGFP in HeLa cells. Similar results were obtained also with 3T3-EGFP and 293T-EGFP cell lines.

Taken together, Example 7 presents several distinct Conjugates of the Invention having distinct structures, but all sharing the core structural motifs according to Formula (I) and Formula (VII), and all manifesting very efficacious delivery of siRNA into the and respective gene silencing.

Example 8: Delivery Across Cell Membranes of a Conjugate of the Invention, where E has the Structure According to Formula (VIIa)

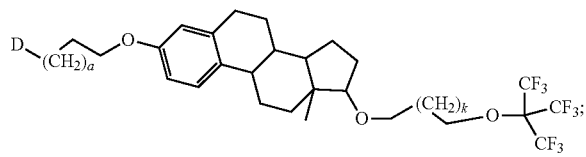

Figure (VIIa)

wherein in the case that a = 2 and k = 1, is designated Apo-Si——C4

3T3 cells and C26 cells were grown and prepared as described in Example 5 above. Cells were incubated for 1, 2, and 24 hours with a Conjugate comprising a 58-mer double-stranded (ds)DNA, linked to Cy3 fluorophore, and lined to two Apo-Si-C4 moieties. Two concentrations of the Conjugate were tested: 40 nM and 100 nM. Analysis comprised fluorescent microscopy and signal quantification by ELISA reader, as described in Example 5 above. An identical 58-mer dsDNA, not linked to E moieties, served as Control.

Fluorescent detection of the Conjugate within the cells was possible already after one hour. Signal was obtained, as desired, in the cytoplasm. Signal intensity markedly increased by 2 hours, with additional augmentation by 24 hours of incubation. Uptake was very clearly measured by the ELISA reader: The ratios of signal intensity of the Conjugate wits the respective control dsDNA, devoid of the MNMs were, for the C26 cells: 80- and 72-fold; while for the 3T3, ratios were 104-, and 101-fold, for concentrations of 40 nM and 100 nM, respectively. Therefore, for both cell types, the Conjugate of the invention enabled highly efficient delivery of a highly-charged 58-mer ds-DNA, as compared to the controls, devoid of the MNM moieties.

Example 9a: Mechanism of Redox-Sensitive Cleavage a Conjugate of the Invention, wherein E, E' or E" Comprises a Cyclic Disulfide Moiety and an Amide Moiety

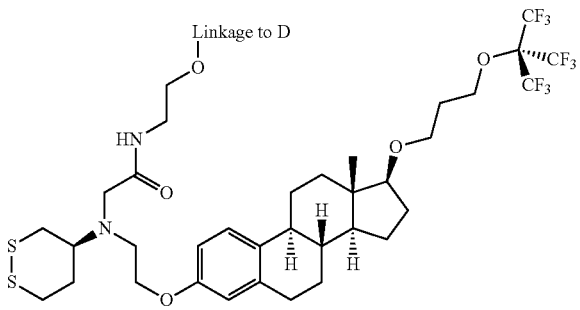

The mechanism is presented in a non-limiting manner. The Conjugate has a disulfide moiety within a six-member ring. Due to the oxidative conditions prevailing in the extracellular space, this ring manifests stability in the plasma and extracellular space. By contrast, within the cells, the Conjugate is subjected to reductive ambient conditions, provided by the high glutathione levels in the cytoplasm. Consequentially, there is cleavage of the disulfide bond, resulting in free thiol groups. Based on analogy to other cyclic disulfide molecules, the pKa values of the free thiol groups are about 8 and 9. Considering the physiological intracellular pH, being about 7, the vast majority of the thiol groups generated upon cleavage of the disulfide bond, are at any time free thiol groups (—SH), and not as the respective thiolate (—S⁻), which is considered to be more nucleophilic. Strategically, the amide carbonyl group is located five and six atoms away from the thiol groups. Similar to its action in catalysis of proteolysis to cysteine proteases, a nucleophilic attack on the carbonyl carbon atom of the amide group takes place, leading to cleavage of the estradiol moiety. Tins action therefore selectively liberates the cargo drug (D) in the cytoplasm. In the case that D is, for example, a siRNA, this leads to entrapment of the highly negatively-charged oligonucleotide in the cytoplasm, ready to interact in situ with the RNA-inducible silencing complex (RISC), in order to exert its acne silencing activity.

This mechanism is described in FIG. 10, where A. represents the intact Conjugate n the extracellular space; B. represents the cleavage of the disulfide bond in the reductive cytoplasmatic millieu; C. represents de-protonation of the thiol to provide the thiolate, in a pka-dependent process; D. represents nucleophilic attack of the thiolate on the carbonyl moiety of the amide group; E. represents generation of at tetrahedral intermediate; F. represents the consequent cleavage of the Conjugate, with generation of a thioester; G. represents subsequent hydrolysis; and H. represents ring closure with formation of a disulfide group, encountered in the oxidative environment at the extracellular space, during excretion of the MNM from the body.

Example 9b: Mechanism of Redox-Sensitive Cleavage of the Conjugate of the Invention, where E has the Structure According to Formula (Xc), and its Utilization for Targeting the Cargo Drug (D) to the Cytoplasm

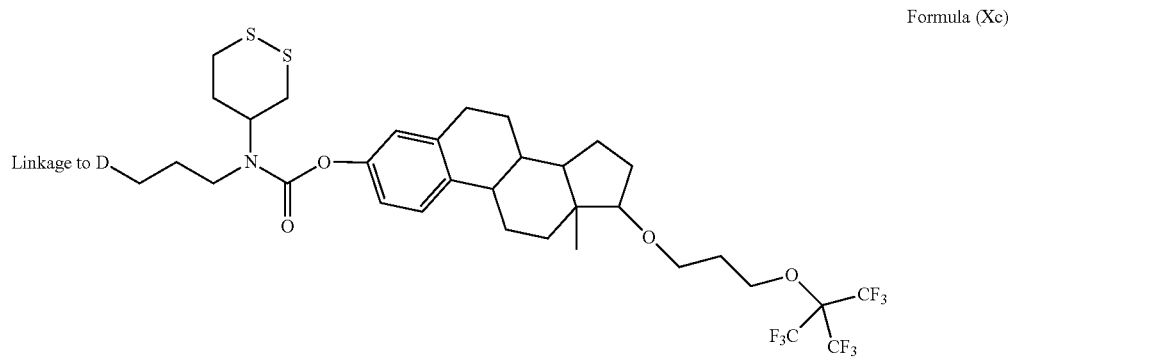

Formula (Xc)

The same mechanism described above for cleavage of the Compound according to Formula (IX), comprising an amide bond, applies also to the cleavage of the Compound according to Formula (Xc), which comprises a carbamate group. As described in FIG. 11: A. represents the intact Conjugate n the extracellular space; B. represents the cleavage of the disulfide bond in the reductive cytoplasmatic millieu; C. represents de-protonation of the thiol into thiolate, in a pka-dependent process; D. represents nucleophilic attack of the thiolate on the carbonyl moiety of the amide group; E. represents generation of a tetrahedral intermediate; F. represents the consequent cleavage of the Conjugate, with generation of a thio-ester; G. represents subsequent hydrolysis, also with release of $CO_2$; and H. represents ring closure with formation of a disulfide group, encountered in the oxidative environment at the extracellular space, during excretion of the MNM from the body.

Example 10: Stability of Structure According to Formula (XIa)

Synthesis of the Conjugates of the Invention customarily involves protecting the nucleobases of the synthesized oligonucleotides by chemical groups. For example, adenine is often protected by a benzoyl protecting group, guanine by isobutyryl, and cytosine by acetyl. These protecting, groups should be removed at the end of synthesis, in order to obtain a functional oligonucleotide. This removal is customarily performed in strong basic conditions. For example, the standard protocol of IDT (Iowa, USA) for removal of the protecting groups during synthesis of oligonucleotides comprises incubation with ammonium hydroxide at 65° C. degrees, for 2 hours. In order to evaluate whether the Compound of the Invention can sustain de-protection in these harsh conditions, a model system was constructed, based on the following Model Compound A, having the following structure:

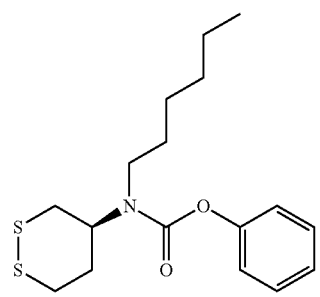

A

Molecular Weight 339,51

Model Compound A

Two mg of this compound were incubated in the above standard conditions used for deprotection. Samples were drawn after 15 minutes, 1 and 2 hours incubation, and evaluated by HPLC/MS, exploring and analyzing the formation of new peaks. Importantly, there were no signs of degradation of Compound A under the conditions of the above protocol. Therefore, this analogue of the compound of the Invention manifested stability in these relatively harsh basic conditions. In addition to the relevance of this observation to the de-protection of oligonucleotides during the synthesis of the Conjugates of the Invention, this observed high stability also suggests stability of these Conjugates during storage.

Example 11: Gene Silencing, Exerted in a Primary Culture of Hepatocytes of Transgenic Mouse Expressing the EGFP Gene, by a Conjugate of the Invention, According to Formula (VIIa), Wherein a=2, and k=1 (Designated Apo-Si-C4)

Double-stranded RNA sequence, as specified in Example 7 was attached to two MNMs according to Formula wherein a=2, and k=1, designated Apo-Si-C4. The conjugate (40 nM) was then incubated with the histone 2A protein (Histone H2A, Molecular Weight 14 kDa; New England Biolabs, Inc.) for 30 minutes (at a 2:1 Histone/RNA ratio) for generation of RNA+MNM+protein complex. The complex was then of incubated with cells of primary culture of hepatocytes of transgenic mice, expressing the EGFP gene. After 72 hours, fluorescence of the EGFP signal was quantified utilizing an ELISA reader, as described in Example 7. As shown in FIG. 12, marked reduction of the EGFP signal of 76% was observed, compared to the fluorescent signal of cells incubated with as control complex, which comprised the same RNA sequence+H2A, but was without the MNMs of the invention. These results demonstrate a robust performance of the MNMs of the invention in enabling trans-membrane delivery of macromolecular structures: the Complex of dsRNA+H2A+two Apo-Si MNMs has a molecular weight of ≈30 kDa, and it carries numerous electric charges. As evident from the results, this complex was capable of effectively crossing the cell membranes, and moreover, exerting a beneficial biological performance in gene silencing. By comparison to the performance of the Control complex, which was devoid of MNMs, the observed results can be attributed solely to the MNMs of the invention.

Example 12: Mechanism of Redox-Sensitive Cleavage of the Conjugate of the Invention, where E, E' or E" has the Structure According to the Following Formula, and its Utilization for Targeting the Cargo Drug (D) to the Cytoplasm

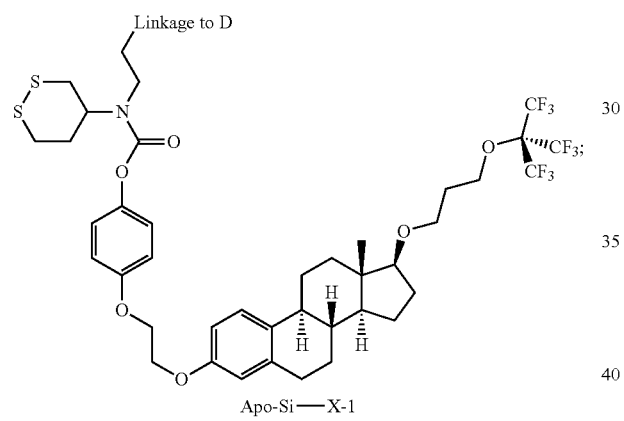

Formula (VII)

Apo-Si—X-1

In the exemplified compound according to Formula (VII); Apo-Si-X-1, as described in FIG. 13: A. represents the intact Conjugate n the extracellular space; B. represents the cleavage of the disulfide bond in the reductive cytoplasmatic millieu; C. represents de-protonation of the thiol into thiolate, in a pKa-dependent process; D. represents nucleophilic attack of the thiolate on the carbonyl moiety of the amide group; E. represents generation of a tetrahedral intermediate; F. represents the consequent cleavage of the Conjugate, with generation of a thio-ester; G. represents subsequent hydrolysis, also with release of $CO_2$; and H. represents ring closure with formation of a disulfide group, encountered in the oxidative environment at the extracellular space, during excretion of the MNM from the body.

Example 13: Molecular Dynamics Simulation (MD) Study, Demonstrating the Interactions of E Moieties of the Invention with Phospholipid Membranes For this demonstration, three compounds were elected, and their structures are set forth below: a. A compound according to Formula (VII), designated Ap-Si-X-1; b. A compound according to Formula (VII), designated Apo-Si-X-2; c. A compound avoiding to Formula (IXb), designated Apo-Si-S-S.

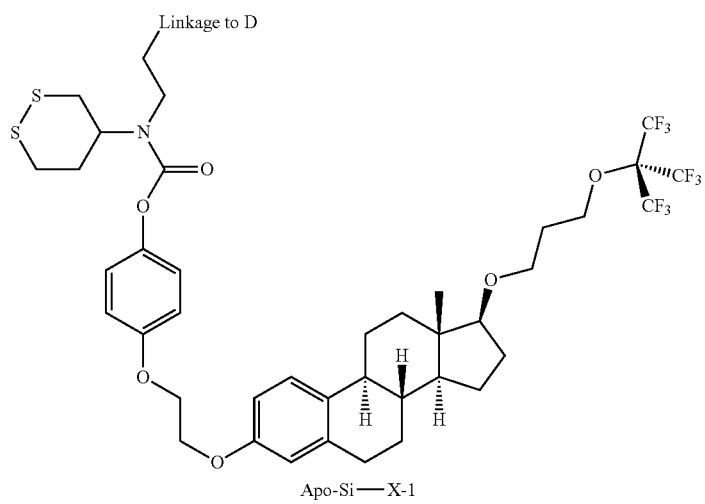

Apo-Si—X-1

-continued

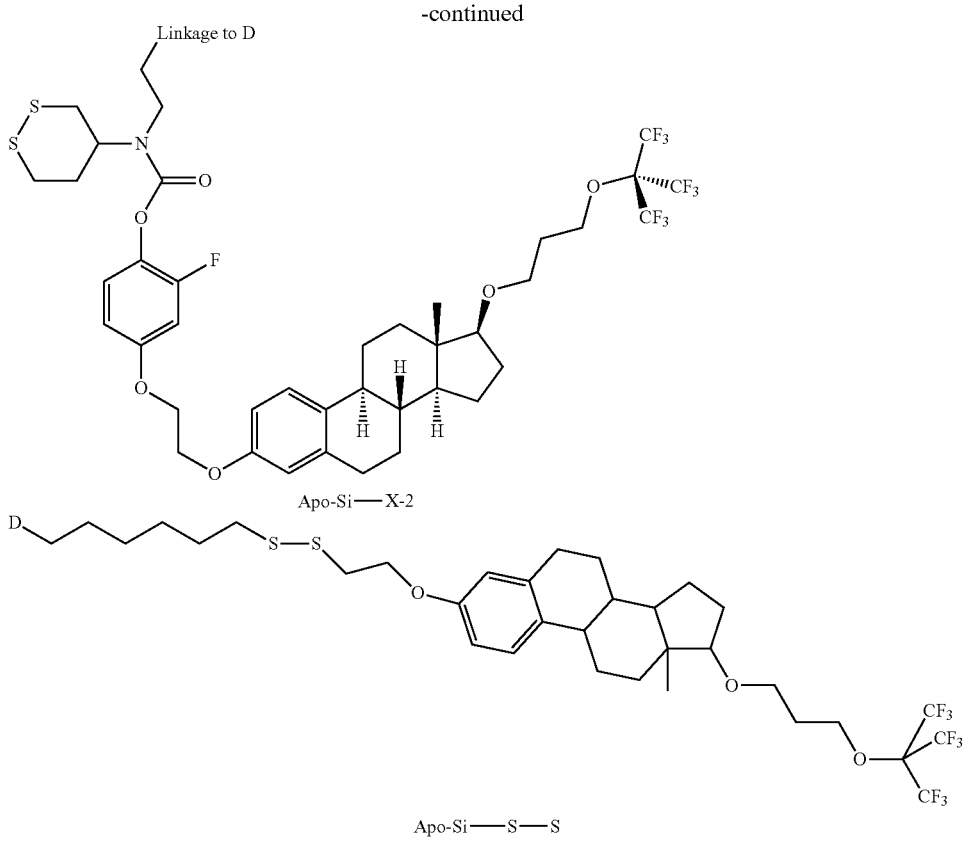

Methods:

A pre-equilibrated (400 nsec at 303° K) POPC (1-palmitoyl-2-oleoyl-sn-glycero-3-phosphocholine) bilayer membrane, consisting of 128 POPC lipids and a 20 Å TIP3P water layer was downloaded from Stockholm Lipids website (http://mmkluster.fos.su.se/slipids/Downloads.html). Apo-Si Compounds Apo-Si-X-1, Apo-Si-X-2 and Apo-Si-S-S were parameterized utilizing the AnteChamber software. Simulations were carried-out using the AMBERI2sb Force Field as implemented in Gromacs (v. 4.5). All compounds were initially located in the water layer at an orientation parallel to the membrane. Ions were added to the solution to make the system electrically neutral to a concentration of 0.15M NaCl. The system was first minimized with compounds constraint to their initial positions, and subsequently with no constraints, using 50,000 steps of steepest descent. Next, the system was equilibrated; first under NVT conditions (500 psec) and subsequently under NPT conditions (2 nsec). During NVT equilibration, the temperature was gradually increased to 303° K (which is above the phase transition temperature of the lipid). Positional restraints were imposed on the lipid head groups in the vertical (z) direction, as well as on the compounds, NPT equilibration employed the Hose-Hoover thermostat, with semi-isotropic pressure coupling, while keeping the positional restraints on the compounds only. Production MD simulations were performed under NPT conditions for 100 ns. All simulations employed a 12 Å cutoff for van der Waals and Coulomb interactions. Long range electrostatic interactions were computed using Particle Mesh Ewald Summation. Periodic boundary conditions were applied. The LINCS algorithm was used to constrain bond lengths.

Results:

As shown in FIG. 14, initially, each molecule was placed within the peri-membrane water layer. Importantly, by 30 nsec for Apo-Si-X-1 and Apo-Si-X-2, and by 100 nsec for Apo-Si-S-S (FIG. 14 A, B, C, respectively), the molecule shifted, and moved vertically within the membrane hydrocarbon core, from the water/lipid interface to the membrane center, where each molecule eventually remained. For each compound, the perfluoro-moieties, namely the negatives pole of the respective MNMs (white arrows), were found to be pulled towards the membrane center. An identical pattern of movement was observed for all three examined compounds.

Conclusion:

This elaborate, non-biased computational work, analyzing the energetics of the molecule vis-a-vis the phospholipid membrane Force-Field, therefore provides additional validation for the Mechanism Of Action (MOA) of the MNMs of the Invention. The similar observations manifested by the three molecules support a unified mechanism of action, which underlies their performance. The structure/function properties of the MNMs were demonstrated, being responsible for the movement of the MNM from the water/hydrocarbon junction to the membrane center, in a manner that is responsive to the membrane dipole potential.

Example 14: Installment of a "Dynamic Protonation Moiety" within an Moiety E, in Order to Enhance Wide Systemic Distribution of the Conjugates of the Invention Upon Systemic Administration In order to perform efficacious trans-membrane delivery of the Conjugates of the Invention that comprise macro-molecule cargo drugs, moiety E has a hydrophobic structure. Characteristically, such moieties bind avidly to plasma proteins, mainly to albumin. This strong binding to plasma proteins may substantially limit the volume of distribution of these Conjugates, limiting the distribution to the intravascular compartment. This is in contrast to the desired profile of the Conjugates, which are designed to manifest wide systemic distribution, teaching various tissues throughout the body. In order to address such potential limitation, the Invention comprises installation of an amine group within E. Such group is exemplified in the structure as set forth according to Formula (VIIIb, Apo-Si-W):

it inhibits the compliance of the E moiety with the membrane dipole potential, which is positive at the membrane center, and thus rejects the intra-membrane insertion of E and its and intra-membrane movement. Being at this form, the Conjugate is then binds less to cell membranes or to plasma proteins, while moving freely across fluid compartments within the body: plasma, intra or extracellular fluids. This form will also act to enhance and expedite the excretion of the E moiety from the body (through the urine or bile), as desired after cleavage from the cargo drug.

The main factor determining the ratio between forms A or B of the E moiety is the pKa of the amine group. While Formula (VIIIb)

wherein in the case that a = 2 and $L_3$ is null; designated Apo-Si-W

Form A (uncharged amine)

Form B (protenated, positively-charged ammonium)

The installment of the amine group generates two forms of the E moiety:

Form A. Hydrophobic.

This form takes place when the amine is at its uncharged term. This form is the effective term of the Molecular NanoMotor, driving an attached macro-molecule drugs to bind to cell membranes and to cross the membranes, utilizing the internal membrane electrical field, associated with the membrane dipole potential.

Form B: Relatively Hydrophilic.

This form takes place upon protonation of the amine. Due to this protonation, the lipid/water partition coefficient of the molecule at the physiological pH of 7.4 (Log D) becomes reduced by nearly 3 orders of magnitude. In addition by introducing a positive charge at the center of the E moiety, usually secondary amines like this amine have a pKa value of about 11 Moiety E of the Invention was designed, as exemplified Apo-Si-W, with the pKa of the amine group being 8.5. Consequently, at any given time-point, and within any compartment within the body, substantial amounts of both Form A and Form B are encountered, with the molecule being capable of conversion between these forms. This, combined with the properties of the Molecular NanoMotors in providing efficacious trans-membrane passage of the Conjugates though cell membranes, therefore enable wide systemic distribution of the Conjugate in the body. Moreover, the system can be easily calibrated by changing the length of the hydrocarbon linker and related perfluoro-motif, in order to optimize performance.

Example 15: Silencing the Expression of the PCSK9 Gene in Hepatic Murine Hepa 1-6 Cells, by a Conjugate of the Invention, According to Formula (IXb)

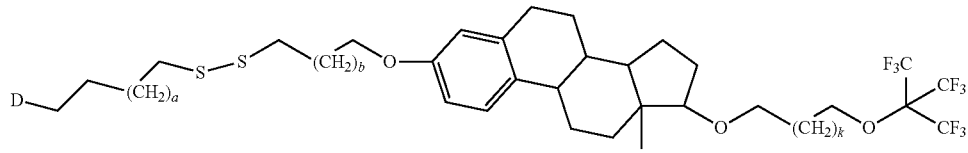

Formula (IXb): In the case that a=3, b=0 and k−1, the moiety is designated Apo-Si-S-S PCSK9 has a role in lowering blood cholesterol levels: when it binds to the LDL receptor, the receptor is broken down and can no longer remove LDL cholesterol from the blood. Therefore, if PCSK9 is blocked, more LDL receptors are present on the surface of the liver, acting to remove more LDL cholesterol from the blood, and thus lowering blood cholesterol levels. The importance of this Example is in the demonstration of the capabilities of Conjugates of the Invention to silence genes that may have a role in disease pathogenesis (hypercholesterolemia in this case), and where the respective gene silencing may have a role as a therapeutic strategy. In addition, the Example demonstrates the respective gene silencing in a relevant cell, i.e., in this case, a cell line of hepatic cells. Thus, it is demonstrated, that the activity of the Conjugates of the Invention extends beyond silencing of a reporter gene such as EGFP, to silencing of disease-related genes.

The examined Conjugate had two E moieties, each having the structure according to Formula (IXb), designated Apo-Si-S-S, thus forming a Conjugate according to general Formula (I), having the structure as described below, and termed here "E-RNA-E' Conjugate", E moieties were constructed by Syncom, Ltd., the Netherlands. Conjugation to the RNA was performed by IDT, Iowa, USA. The structure of the Conjugate was:

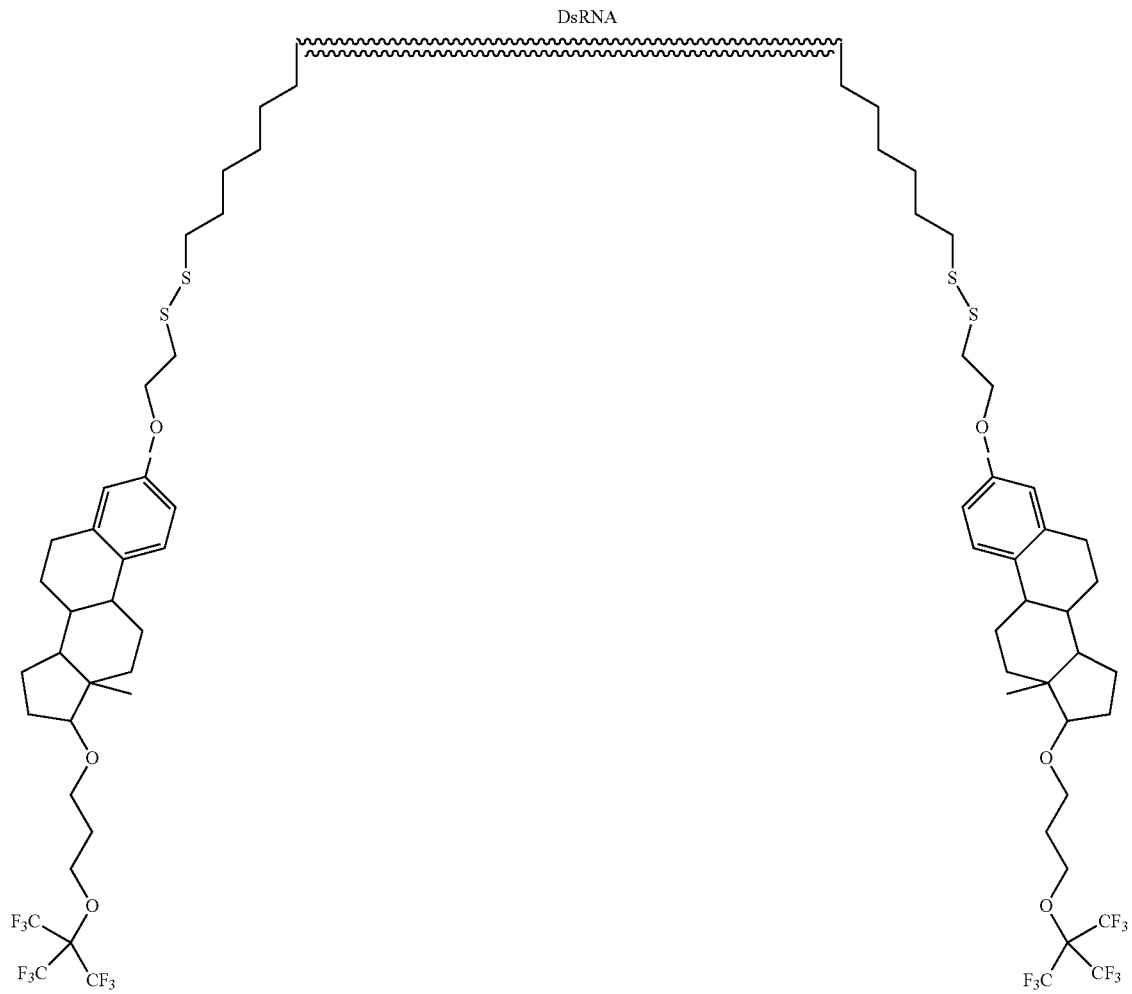

The dsRNA part of the Conjugate comprised a 25-27 Dicer substrate, double-stranded RNA, specifically designed to silence the PCSK9 gene, and linked on It was found, that the Conjugate of the Invention induced silencing of the PCSK9 gene to the extent 75.5%, at a dose of 400 nM, as compared to RNA control of the same sequence, but devoid of the Apo-Si Molecular Nano-Motors (p<0.001).

This Example therefore demonstrates that the "Molecular NanoMotor(s) (MNMs) enable: (i). Trans-membrane delivery of the otherwise membrane-impermeable siRNA, (ii). Navigation of the E-RNA-E' Conjugate into the cytoplasm, and; (iii). Exertion of a desirable performance, in silencing the expression of a disease-related gene.

Example 16: Gene Silencing, Exerted in 3T3 Cells Expressing the EGFP Gene, by a Conjugate of the Invention, According to Formula (XI) (Apo-Si-X-2)

The Conjugate examined in this Example was a Conjugate wherein E and E', each had the structure as set forth in Formula (Xb), wherein R=F, R'=H, a=2, W+O, k=1; having the following structure, and designated Apo-Si-X-2:

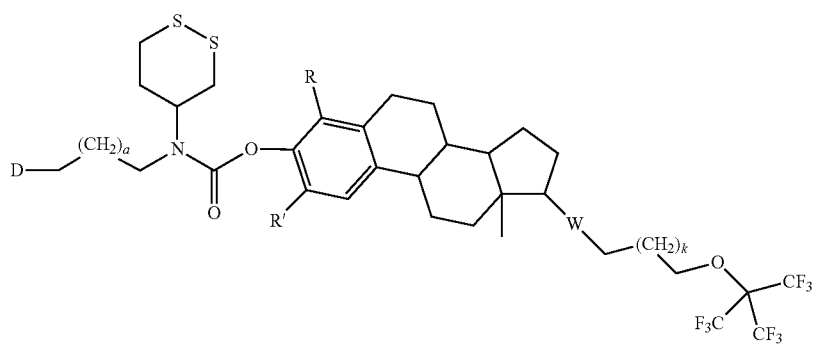

Formula (Xb)

Cells were 3T3 cells, stably expressing the EGFP gene. Cell line was grown in Dulbecco's modified Eagle's medium (DMEM) supplemented with 10% FCS, 100 U/ml penicillin and 100 mg/ml streptomycin 10 µg/ml and maintained in a 37° C. incubator with 5% $CO_2$ humidified air. One day before the transfection, 25,000 3T3-EGFP cells were plated in as 24-well chamber. The day later, cells were transfected with Apo-Si-X2 (0.6 µM), conjugated to si-RNA sequence designed to knockdown the EGFP gene (sequence described in Example 12). 72 hours post transfection, medium was aspirated and cells were lysed and subjected to fluorescence quantification with the Tecan Infinite® 200 PRO multimode reader. EGFP protein levels were quantified with excitation at 488=5 nm and emission at 535±10 nm. Compared to the controls, treated with siRNA devoid of the Apo-Si Molecular NonoMotors, cells treated with the Conjugate of the invention manifested knockdown of gene expression to 75%, thus demonstrating the performance of the Conjugates.

Example 17

Molecular simulation studies, exemplifying the Principle of dynamic protonation, utilized in the present invention, as a performance enhancing moiety, that entails, pending on the protonation state of the MNM, provides both a water-soluble form of the molecule, capable of moving within the plasma or cytoplasm, and a water-insoluble him capable of moving within the cell membrane milieu, which together provide a large volume of distribution of the Conjugate.

Methods:

Molecular simulation study of the interaction of unprotonated and protonated forms of Apo-Si-W was performed as described in Example 13. The MNM utilized was of the structure of Apo-Si-W, according to Formula (VIIIb), linked to a phosphate group, to simulate the phosphate groups of the RNA. Two protonated states of the tertiary amine of the Apo-Si-W were utilized, according to Example 14: unprotonated; and protonated (positively-charged). The structure at each protonation states was run independently in a computerized molecular simulation model system of phospholipid membrane several days, until simulation of 100 nano-seconds was achieved, initial position of each structure was parallel to the membrane surface.

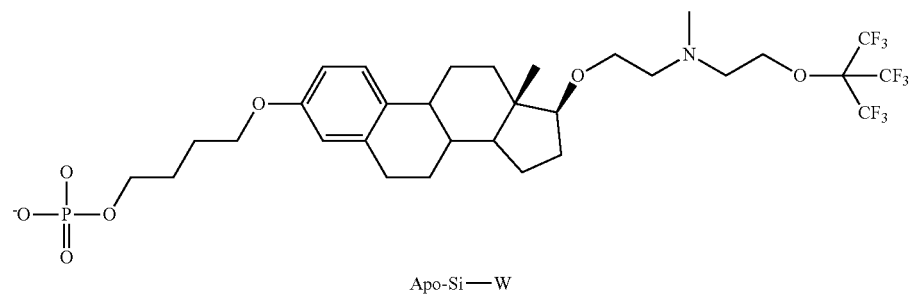

Apo-Si—W

Results:

FIG. 15 provides a representative position of each the molecule at the end of the 100 nanosecond run. Protonted, positively-charged form FIG. 15A, was found to be excluded from the membrane throughout the simulation period; By contrast, the hydrophobic, unprotonated form of the molecule manifested excellent portioning into the phospholipid membrane (FIG. 15B). Interestingly, and importantly, the membrane portioning of the uncharged form into the membrane was in accordance to the polarity of the internal membrane electrical field, with the negative pole of the MNM reaching the center of the membrane, i.e., the positive pole of the electrical field.

Conclusion:

As evaluated in this molecular simulation model, the protonation state of the single, dynamically-protonated nitrogen atom, was capable of govern the membrane interaction of the entire E motif.

The invention claimed is:

1. A conjugate according to general Formula (I),

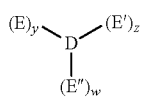

Formula (I)

or a pharmaceutically acceptable salt, hydrate, or solvate thereof, or a solvate or hydrate of the salt, wherein:

D is a drug selected from a group consisting of a small-molecule drug, a peptide, a protein, a native or modified, single-stranded or double-stranded DNA or RNA, siRNA, and antisense oligonucleotide (ASO);

y, z and w are each an integer, independently selected from 0, 1, 2, 3, 4, 5, or 6, wherein at least one of y, z or w is different from 0;

E, E' and E'' are the same or different, and are defined by the Formula (VII):

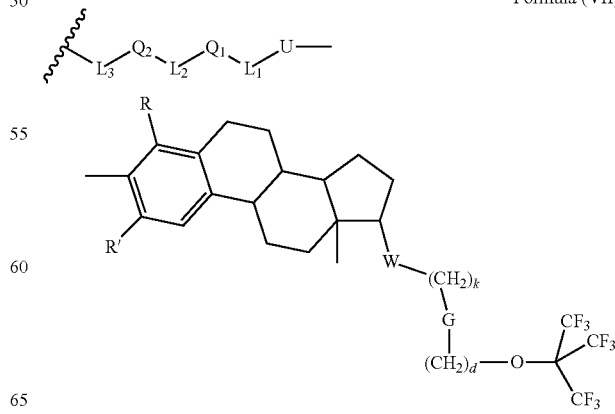

Formula (VII)

U is —O—;

$Q_1$ and $Q_2$ are each independently selected from null, ester, amide, carbamate, urea, disulfide, or amine;

$L_1$, $L_2$, and $L_3$ are each independently selected from null, a linear $C_{1-14}$ alkyl or heteroalkyl, a cyclic or branched $C_{3-14}$ alkyl or heteroalkyl, $C_{5-6}$ aryl or heteroaryl, or —(O—CH$_2$—CH$_2$)$_u$—; wherein u is an integer of 1, 2, 3, 4, or 5;

wherein at least one of $Q_1$, $Q_2$, $L_1$, $L_2$, and $L_3$ is not null;

R and R' are each hydrogen;

W is —O—;

G is null, a secondary or tertiary amine groups;

d and k are each an integer, independently selected from 0, 1, 2, 3, 4, 5, or 6.

2. The conjugate according to claim 1, wherein $L_1$, $L_2$, and $L_3$ are each independently selected from null, a linear $C_{1-8}$ alkyl, cyclic or branched $C_{3-8}$ alkyl.

3. The conjugate according to claim 1, wherein at least one of the E, E', or E" has the structure as set forth in Formula (VIIa):

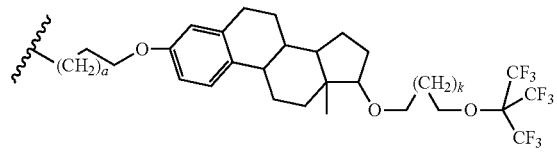

FIG (VIIa)

wherein a and k each are independently selected from 0, 1, 2, 3, 4, 5, or 6.

4. The conjugate according to claim 1, wherein at least one of the E, E', or E" has the structure as set forth in Formula (VIIIa) or Formula (VIIIb):

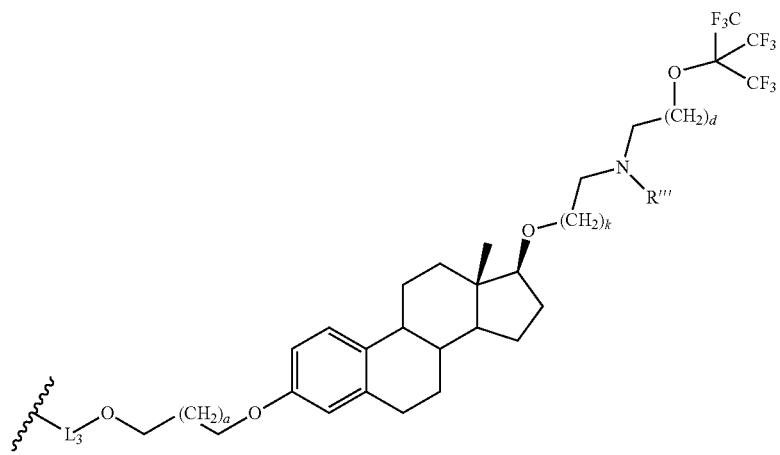

Formula (VIIIa)

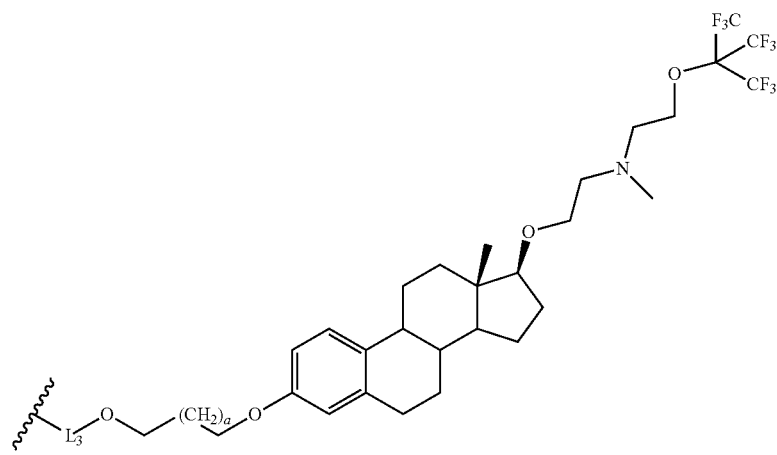

Formula (VIIIb)

wherein $L_3$ is as defined in claim 1; a, k and d are each an integer, independently selected from 0, 1, 2, 3, 4, 5, or 6; and R''' is selected from the group consisting of hydrogen, methyl and ethyl.

5. The conjugate according to claim 1, wherein at least one of the E, E', or E" has the structure as set forth in Formula (IX):

Formula (IX)

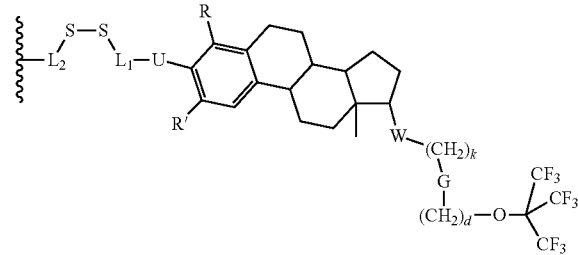

wherein U is —O—;

$L_1$ and $L_2$ are as defined in claim 1;

R and R' are each hydrogen;

W is —O—;

G is null, a secondary or tertiary amine groups;

d and k are each an integer, independently selected from 0, 1, 2, 3, 4, 5, or 6.

6. The conjugate according to claim 1, wherein at least one of the E, E', or E" has the structure as set forth in Formula (IXa), Formula (IXb), Formula (IXc), or Formula (IXd):

Formula (IXa)

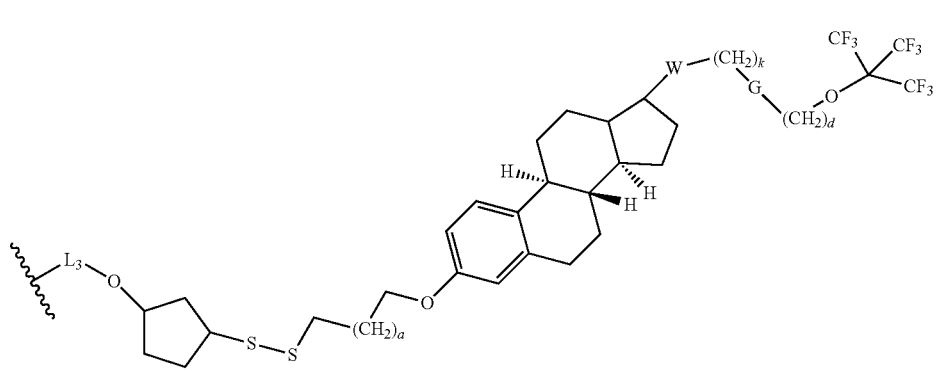

Formula (IXb)

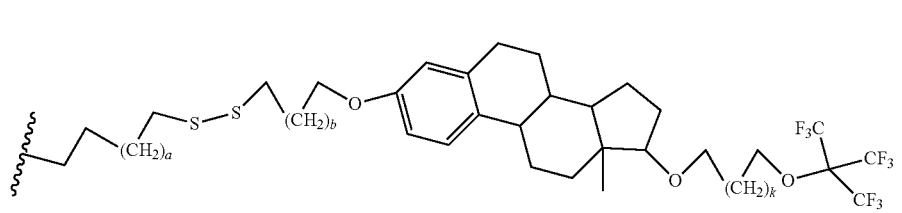

Formula (IXc)

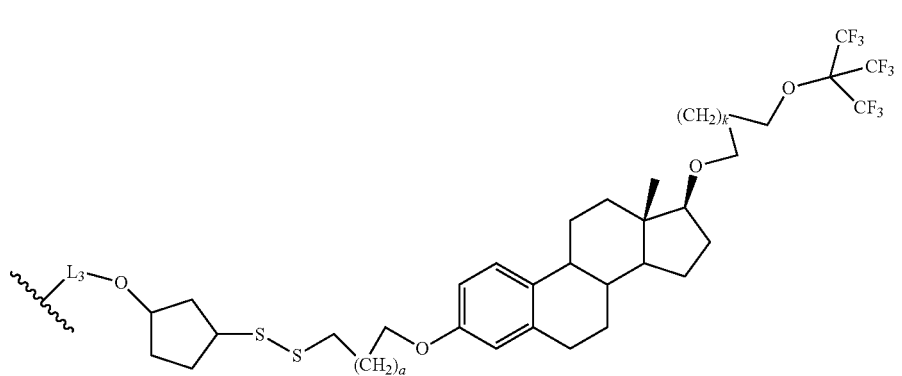

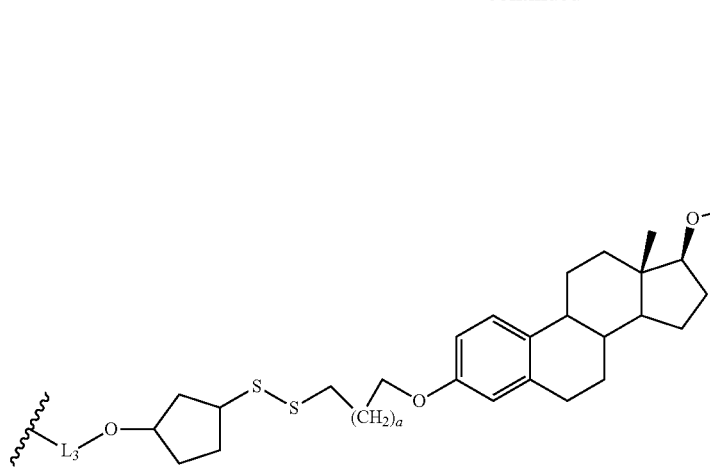

Formula (IXd)

wherein $L_3$ is as defined in claim 1;
W is —O—;
G is null, a secondary or tertiary amine groups;
a, b, d and k are each an integer, independently selected from 0, 1, 2, 3, 4, 5, or 6;
R''' is selected from the group consisting of hydrogen, methyl and ethyl.

7. The conjugate according to any of claim 1, 3, 4, 5, or 6, wherein the drug is selected from the group consisting of siRNA, ASO and a therapeutic protein.

8. A pharmaceutical composition comprising the conjugate according to any of claim 1, 3, 4, 5, or 6 and a pharmaceutically acceptable carrier.

9. A method for delivery of a drug into biological cells, wherein said cells are in culture, or in a living animal or a human subject; the method comprising contacting the cells with the Conjugate according claim 1.

10. A method for delivery of a drug across biological membranes, the method comprising delivering the drug across biological membranes by utilizing the conjugate according to claim 1.

11. The method according to claim 10, wherein the biological membrane is selected from a group consisting of cell membranes and biological barriers, wherein said biological barriers are selected from the blood-brain-barrier, blood-ocular-barrier or the blood-fetal-barrier.

12. A precursor having the structure as set forth in formula (XII):

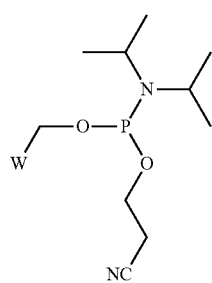

Formula (XII)

wherein W is selected from the structures defined by the formula (VII) according to claim 1, the formula (VIIa) according to claim 3, the formula (VIIIa) or (VIIIb) according to claim 4, the formula IX according to claim 5, or the formula (IXa), (IXb), (IXc), or (IXd) according to claim 6.

13. A precursor having the structure as set forth in formula (XIII):

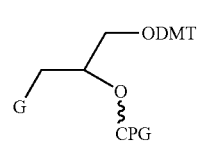

Formula (XIII)

wherein G is selected from the structures defined by the formula (VII) according to claim 1, the formula (VIIa) according to claim 3, the formula (VIIIa) or (VIIIb) according to claim 4, the formula IX according to claim 5, or the formula (IXa), (IXb), (IXc), or (IXd) according to claim 6; DMT is dimethoxytrityl which is a protecting group for hydroxyl group; and CPG is Controlled-Pore-Glass.

14. A precursor having the structure as set forth in formula (XIV):

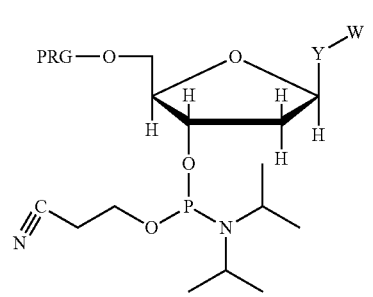

Formula (XIV)

wherein W is selected from the structures defined by the formula (VII) according to claim 1, the formula (VIIa) according to claim 3, the formula (VIIIa) or (VIIIb) according to claim 4, the formula IX according to claim 5, or the formula (IXa), (IXb), (IXc), or (IXd) according to claim 6; PRG is a protecting group suitable for protecting a hydroxyl group; Y is selected from a 1, 2, 3, 4, 5, 6, 7, or 8 hydrocarbon linker, optionally substituted by oxygen, or nitrogen(s), and optionally linked to any natural or modified RNA or DNA base.

15. A precursor acco4ding to claim 14, wherein PRG is dimethoxytrityl bis-(4-methoxyphenyl) phenylmethyl; and the base is thymine or uracil.

16. A precursor having the structure as set forth in formula A or B

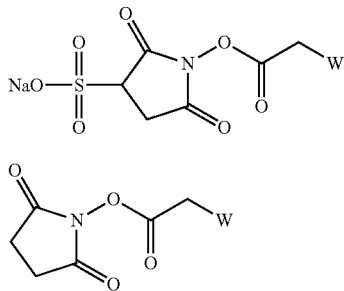

W is selected from the structures defined by the formula (VII) according to claim 1, the formula (VIIa) according to claim 3, the formula (VIIIa) or (VIIIb) according to claim 4, the formula IX according to claim 5, or the formula (IXa), (IXb), (IXc), or (IXd) according to claim 6; said precursor is for attachment of a protein drug to W at the amine moieties of the protein drug.

17. A method for delivery of a drug across biological membranes, the method comprising delivering the drug across biological membranes by utilizing the conjugate according to claim 3.

18. A method for delivery of a drug across biological membranes, the method comprising delivering the drug across biological membranes by utilizing the conjugate according to claim 4.

19. A method for delivery of a drug across biological membranes, the method comprising delivering the drug across biological membranes by utilizing the conjugate according to claim 5.

20. A method for delivery of a drug across biological membranes, the method comprising delivering the drug across biological membranes by utilizing the conjugate according to claim 6.

21. A method for delivery of a drug across biological membranes, the method comprising delivering the drug across biological membranes by utilizing the conjugate according to claim 7.

* * * * *